US011942222B2

(12) United States Patent
Freeman et al.

(10) Patent No.: US 11,942,222 B2
(45) Date of Patent: Mar. 26, 2024

(54) MEDICAL DEVICE FOR ESTIMATING RISK OF PATIENT DETERIORATION

(71) Applicant: ZOLL Medical Corporation, Chelmsford, MA (US)

(72) Inventors: Gary A. Freeman, Waltham, MA (US); Christopher L. Kaufman, Somerville, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 783 days.

(21) Appl. No.: 16/444,601

(22) Filed: Jun. 18, 2019

(65) Prior Publication Data
US 2019/0385744 A1    Dec. 19, 2019

Related U.S. Application Data

(60) Provisional application No. 62/686,330, filed on Jun. 18, 2018.

(51) Int. Cl.
*G16H 50/30* (2018.01)
*A61B 5/00* (2006.01)
(Continued)

(52) U.S. Cl.
CPC ........... *G16H 50/30* (2018.01); *A61B 5/0205* (2013.01); *A61B 5/349* (2021.01); *A61B 5/681* (2013.01);
(Continued)

(58) Field of Classification Search
CPC ........ G16H 10/60; G16H 50/20; G16H 40/63; A61B 5/349; A61B 5/681; A61B 5/316;
(Continued)

(56) References Cited

U.S. PATENT DOCUMENTS 3,862,636 A   1/1975  Bell et al.
3,886,950 A   6/1975  Ukkestad et al.
(Continued)

FOREIGN PATENT DOCUMENTS

EP   0761255 A1   3/1997
JP   H10505515 A   6/1998
(Continued)

OTHER PUBLICATIONS

A Review of Automated Methods for Detection of Myocardial Ischemia and Infarction Using Electrocardiogram and Electronic Health Records, IEEE Reviews in Biomedical Engineering, vol. 10, 2017, Sardar Ansari et al. (Year: 2017).*
(Continued)

*Primary Examiner* — Dilek B Cobanoglu
(74) *Attorney, Agent, or Firm* — Finch & Maloney PLLC

(57) ABSTRACT

A medical device for assessing clinical patient deterioration in an in-patient hospital environment is provided. The medical device includes a processor and sensors that couple externally to a skin of the patient to acquire electrocardiogram (ECG) and other physiologic signals. The processor is configured to receive a medical history of the patient; generate physiologic data, including ECG data, over a period of time based on one or more physiologic signals; and execute a risk assessment process associated with a clinical (Continued)

condition of the patient. The risk assessment process analyzes the physiologic data and the medical history of the patient to generate a risk estimate of deterioration of the patient's clinical condition.

25 Claims, 12 Drawing Sheets

(51) Int. Cl.
    *A61B 5/0205*     (2006.01)
    *A61B 5/349*     (2021.01)
    *A61N 1/39*     (2006.01)
    *G16H 10/60*     (2018.01)
    *A61B 5/316*     (2021.01)
    *G16H 40/63*     (2018.01)
    *G16H 50/20*     (2018.01)

(52) U.S. Cl.
    CPC ........... *A61N 1/3925* (2013.01); *G16H 10/60* (2018.01); *A61B 5/316* (2021.01); *A61B 5/6815* (2013.01); *A61B 5/6822* (2013.01); *A61B 5/683* (2013.01); *G16H 40/63* (2018.01); *G16H 50/20* (2018.01)

(58) Field of Classification Search
    CPC ..... A61B 5/6815; A61B 5/6822; A61B 5/683; A61B 5/14542; A61N 1/3925
    USPC ........................................................ 705/2, 3
    See application file for complete search history.

(56) References Cited

U.S. PATENT DOCUMENTS

| | | | |
|---|---|---|---|
| 4,088,138 A | 5/1978 | Diack et al. |
| 4,576,170 A | 3/1986 | Bradley et al. |
| 4,580,572 A | 4/1986 | Granek et al. |
| 4,583,547 A | 4/1986 | Granek et al. |
| 4,619,265 A | 10/1986 | Morgan et al. |
| 4,729,377 A | 3/1988 | Granek et al. |
| 4,928,690 A | 5/1990 | Heilman et al. |
| 4,991,217 A | 2/1991 | Garrett et al. |
| 5,078,134 A | 1/1992 | Heilman et al. |
| 5,342,404 A | 8/1994 | Alt et al. |
| 5,472,453 A | 12/1995 | Alt |
| 5,607,454 A | 3/1997 | Cameron et al. |
| 5,741,306 A | 4/1998 | Glegyak et al. |
| 5,929,601 A | 7/1999 | Kiab et al. |
| 5,944,669 A | 8/1999 | Kiab |
| 6,065,154 A | 5/2000 | Hulings et al. |
| 6,097,982 A | 8/2000 | Glegyak et al. |
| 6,253,099 B1 | 6/2001 | Oskin et al. |
| 6,280,461 B1 | 8/2001 | Glegyak et al. |
| 6,304,783 B1 | 10/2001 | Lyster et al. |
| 6,336,900 B1 | 1/2002 | Alleckson et al. |
| 6,374,138 B1 | 4/2002 | Owen et al. |
| 6,405,082 B1 | 6/2002 | Borgenicht |
| 6,406,426 B1 | 6/2002 | Reuss et al. |
| 6,546,285 B1 | 4/2003 | Owen et al. |
| 6,681,003 B2 | 1/2004 | Linder et al. |
| 6,690,969 B2 | 2/2004 | Bystrom et al. |
| 6,751,501 B1 | 6/2004 | Schuler |
| 6,889,078 B2 | 5/2005 | Struble et al. |
| 6,889,079 B2 | 5/2005 | Bocek et al. |
| 6,908,437 B2 | 6/2005 | Bardy |
| 6,990,373 B2 | 1/2006 | Jayne et al. |
| 7,149,579 B1 | 12/2006 | Koh et al. |
| 7,340,296 B2 | 3/2008 | Stahmann et al. |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,712,373 B2 | 5/2010 | Nagle et al. |
| 7,831,303 B2 | 11/2010 | Rueter et al. |
| 7,974,689 B2 | 7/2011 | Volpe et al. |
| 7,991,460 B2 | 8/2011 | Fishell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,369,944 B2 | 2/2013 | Macho et al. |
| 8,406,842 B2 | 3/2013 | Kaib et al. |
| 8,644,925 B2 | 2/2014 | Volpe et al. |
| 8,649,861 B2 | 2/2014 | Donnelly et al. |
| 8,676,313 B2 | 3/2014 | Volpe et al. |
| 8,706,215 B2 | 4/2014 | Kaib et al. |
| 8,774,917 B2 | 7/2014 | Macho et al. |
| 8,880,196 B2 | 11/2014 | Kaid |
| 8,897,860 B2 | 11/2014 | Volpe et al. |
| 8,904,214 B2 | 12/2014 | Volpe et al. |
| 9,283,399 B2 | 3/2016 | Donnelly et al. |
| 10,490,309 B1* | 11/2019 | McNair ................. G16H 50/20 |
| 10,932,726 B2* | 3/2021 | Volosin .............. A61B 5/14542 |
| 2001/0031991 A1 | 10/2001 | Russial |
| 2003/0004547 A1 | 1/2003 | Owen et al. |
| 2003/0032988 A1 | 2/2003 | Fincke |
| 2003/0095648 A1 | 5/2003 | Kaib et al. |
| 2005/0131465 A1 | 6/2005 | Freeman et al. |
| 2006/0211934 A1 | 9/2006 | Hassonjee et al. |
| 2007/0118056 A1 | 5/2007 | Wang et al. |
| 2007/0129769 A1 | 6/2007 | Bourget et al. |
| 2007/0169364 A1 | 7/2007 | Townsend et al. |
| 2008/0033495 A1 | 2/2008 | Kumar |
| 2008/0046015 A1 | 2/2008 | Freeman et al. |
| 2008/0167535 A1 | 7/2008 | Stivoric et al. |
| 2008/0177341 A1 | 7/2008 | Bowers |
| 2008/0306560 A1 | 12/2008 | Macho et al. |
| 2008/0306562 A1 | 12/2008 | Donnelly et al. |
| 2008/0312709 A1 | 12/2008 | Volpe et al. |
| 2009/0076344 A1 | 3/2009 | Libbus et al. |
| 2009/0076363 A1 | 3/2009 | Bly et al. |
| 2009/0076559 A1 | 3/2009 | Libbus et al. |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2009/0312650 A1 | 12/2009 | Maile et al. |
| 2010/0052892 A1 | 3/2010 | Allen et al. |
| 2010/0069735 A1 | 3/2010 | Berkner |
| 2010/0076533 A1 | 3/2010 | Dar et al. |
| 2010/0171611 A1 | 7/2010 | Gao et al. |
| 2010/0241181 A1 | 9/2010 | Savage et al. |
| 2010/0298899 A1 | 11/2010 | Donnelly et al. |
| 2010/0312297 A1 | 12/2010 | Volpe et al. |
| 2011/0022105 A9 | 1/2011 | Owen et al. |
| 2011/0170692 A1 | 7/2011 | Konrad et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0095300 A1* | 4/2012 | McNair ................ A61B 5/0022 600/300 |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2012/0302860 A1 | 11/2012 | Volpe et al. |
| 2013/0013014 A1 | 1/2013 | Donnelly et al. |
| 2013/0027411 A1 | 1/2013 | Hebler et al. |
| 2013/0060149 A1 | 3/2013 | Song et al. |
| 2013/0085538 A1 | 4/2013 | Volpe et al. |
| 2013/0144355 A1 | 6/2013 | Macho et al. |
| 2013/0218252 A1 | 8/2013 | Kaib et al. |
| 2013/0231711 A1 | 9/2013 | Kaib |
| 2013/0324868 A1 | 12/2013 | Kaib et al. |
| 2013/0325078 A1 | 12/2013 | Whiting et al. |
| 2013/0325096 A1 | 12/2013 | Dupelle et al. |
| 2014/0163334 A1 | 6/2014 | Volpe et al. |
| 2014/0206974 A1 | 7/2014 | Volpe et al. |
| 2014/0277243 A1 | 9/2014 | Maskara et al. |
| 2014/0303680 A1 | 10/2014 | Donnelly et al. |
| 2014/0324112 A1 | 10/2014 | Macho et al. |

(56) References Cited

U.S. PATENT DOCUMENTS

| | | | |
|---|---|---|---|
| 2015/0006088 A1* | 1/2015 | Eshelman | G16H 50/30 |
| | | | 702/19 |
| 2015/0035654 A1 | 2/2015 | Kaib et al. | |
| 2015/0039042 A1 | 2/2015 | Amsler et al. | |
| 2015/0039053 A1 | 2/2015 | Kaib et al. | |
| 2015/0080699 A1 | 3/2015 | Kaib et al. | |
| 2015/0224330 A1 | 8/2015 | Kaib et al. | |
| 2015/0250428 A1* | 9/2015 | Zhang | A61B 5/7275 |
| | | | 600/301 |
| 2016/0135706 A1 | 5/2016 | Sullivan et al. | |
| 2016/0147959 A1* | 5/2016 | Mariottini | G16H 50/20 |
| | | | 706/46 |
| 2017/0164840 A1* | 6/2017 | Matsumoto | A61B 5/02405 |
| 2017/0281097 A1* | 10/2017 | Thakur | A61N 1/3627 |
| 2017/0290551 A1* | 10/2017 | An | A61B 5/1118 |

FOREIGN PATENT DOCUMENTS

| | | | | |
|---|---|---|---|---|
| JP | 2002-514107 | A | 5/2002 | |
| JP | 2006136707 | A | 6/2006 | |
| JP | 2008-302228 | A | 12/2008 | |
| JP | 2008302225 | A | 12/2008 | |
| JP | 2009510631 | A | 3/2009 | |
| WO | 83/04171 | A1 | 12/1983 | |
| WO | 1998039061 | A2 | 9/1998 | |
| WO | 2004078259 | A1 | 9/2004 | |
| WO | WO-2008042344 | A2 * | 4/2008 | A61B 5/02007 |
| WO | 2009122277 | A2 | 10/2009 | |
| WO | 2010025432 | A1 | 3/2010 | |
| WO | 2010077997 | A2 | 7/2010 | |
| WO | 2013130957 | A2 | 9/2013 | |
| WO | 2014097035 | A1 | 6/2014 | |
| WO | 2012/006524 | A1 | 1/2021 | |

OTHER PUBLICATIONS

Machine Learning and Decision Support in Critical Care, Proceedings of the IEEE | vol. 104, No. 2, Feb. 2016, Alistair E. W. Johnson et al. (Year: 2016).*

American Journal of Respiratory and Critical Care Medical, vol. 166, pp. 111-117 (2002), American Thoracic Society, ATS Statement: Guidelines for the Six-Minute Walk Test, available at http://ajsjournals.org/cgi/content/ull/166/1/111.

http:/web.archive.org/web/20030427001846/http:/www.lifecor.comiimagelib/imageproduct.asp. Published by LifeCor, Inc., 2002, on a webpage owned by LifeCor, Inc.

Association for the Advancement of Medical Instrumentation, ANSI/AAMI DF80:2003 Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

Zoll Medical Corporation, LifeVest Model WCD 3000 Operator's Manual, Pittsburgh, PA.

Wikipedia, Automated External Defibrillator, May 31, 2009, Wikipedia, Section on Mechanism of Operation.

International Preliminary Report on Patentability for Application No. PCT/US2019/037714 dated Dec. 22, 2020, 8 pages.

PCT Search Report and Written Opinion for PCT Application No. PCT/US19/37714 dated Sep. 12, 2019, 10 pages.

Wan et al., "The Unscented Kalman Filter for Nonlinear Estimation", Proceedings of the IEEE 2000 Adaptive Systems for Signal Processing, Communications, and Control Symposium (Cat. No. 00EX373), pp. 153-158, doi:10.1109/ASSPCC.2000.882463 (Feb. 2000).

Wan et al., "Semantic-Geographic Trajectory Pattern Mining Based on a New Similarity Measurement", ISPRS International Journal of Geo-Information, 6, 212, doi:10.3390/ijgi6070212 (Jul. 2017).

* cited by examiner

MEDICAL DEVICE FOR ESTIMATING RISK OF PATIENT DETERIORATION

RELATED APPLICATIONS

This application claims priority under 35 U.S.C. § 119 (e) to U.S. Provisional Application Ser. No. 62/686,330, titled "MEDICAL DEVICE FOR ESTIMATING RISK OF PATIENT DETERIORATION," filed Jun. 18, 2018, which is hereby incorporated herein by reference in its entirety.

BACKGROUND

The present disclosure is directed to medical devices that monitor clinical conditions of hospitalized patients.

A patient may be admitted for an in-hospital stay on presenting a variety of clinical conditions. During the course of the stay, the patient is continuously or periodically assessed for changes in the presentable clinical conditions and for development of new conditions. Rapid response teams, medical emergency response teams or medical emergency teams (variously called RRT, MERT, or MET) were introduced in the care of such patients to respond to unexpected and/or sudden clinical deterioration. Such teams can be a key component of a hospital's rapid response system. Such systems have been put in place in hospitals in view of historical data showing evidence of failure to rescue with available clinical services, often leading to serious adverse events.

There are a wide variety of electronic and mechanical devices for monitoring and treating patients' medical conditions during their hospital stay. In some examples, depending on the underlying medical condition being monitored or treated, such medical devices can include devices such as cardiac monitors or external defibrillators. In some cases, caregivers may use medical devices alone or in combination with drug therapies to treat cardiac conditions such as cardiac arrhythmias. Treatable forms of cardiac conditions include ventricular fibrillation (VF), a deadly form of arrhythmia where normal, regular electrical impulses deteriorate into irregular and rapid impulses that cause the heart muscle to stop normal contractions. Because the victim has no perceptible warning of the impending fibrillation, death often occurs before the necessary medical assistance can arrive, even in a hospital environment. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity) result in the heart providing insufficient levels of blood flow to the brain and other organs vital for the support of life. The sooner resuscitation efforts begin, the better the patient's chances of survival. For example, ventricular fibrillation or ventricular tachycardia can be treated by a defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

Example external cardiac monitoring and/or treatment devices include cardiac monitors, the ZOLL LifeVest® wearable cardioverter defibrillator available from ZOLL Medical Corporation, and the AED Plus also available from ZOLL Medical Corporation.

SUMMARY

In at least one example, a medical device for assessing patient deterioration in an in-patient hospital environment is provided. The medical device includes a memory, a plurality of sensing electrodes, one or more physiologic sensors, and at least one processor coupled to the memory, the plurality of sensing electrodes, and the one or more physiologic sensors. The memory stores data identifying a plurality of presentable clinical conditions, a plurality of risk assessment processes associated with the plurality of presentable clinical conditions, and a corresponding plurality of clinical criteria associated with the plurality of risk assessment processes. The plurality of sensing electrodes is configured to couple externally to a skin of a patient and to acquire electrocardiogram (ECG) signals. The one or more physiologic sensors are configured to couple externally to the patient and configured to acquire one or more physiologic signals. The at least one processor is configured to generate ECG data over a predetermined period of time based on the ECG signals; generate physiologic data over the predetermined period of time based on the one or more physiologic signals; receive at least one of medical history and demographic information of the patient; execute a first risk assessment process associated with a first clinical condition selected from the plurality of presentable clinical conditions based the ECG data, the physiologic data, and the at least one of medical history and demographic information of the patient to generate a first risk estimate of deterioration of the patient; and generate a notification in response to the first risk estimate of deterioration of the patient being outside a first clinical criterion of the plurality of clinical criteria, the first clinical criterion being associated with the first clinical condition.

Implementations of such a medical device may include one or more of the following features.

The medical device may further include a user interface coupled to the at least one processor, wherein the at least one processor may be further configured to receive the at least one of medical history and demographic information via the user interface. In the medical device, the at least one processor may be further configured to receive, via the user interface, an initial patient assessment and identify the first clinical condition based on the initial patient assessment. The medical device may further include a network interface coupled to the at least one processor and the at least one processor may be further configured to receive the at least one of medical history and demographic information via the network interface. The network interface may be configured to communicate with one or more of a personal electronic device using near-field communication and a cloud server using Ethernet communication. In the medical device, the plurality of presentable clinical conditions may include one or more of a heart failure condition, a post syncope condition, a post myocardial infarction condition, and a breathing disorder condition. In the medical device, the at least one processor may be further configured to automatically identify the first clinical condition based on an initial patient assessment of the ECG data, the physiologic data, and the at least one of medical history and demographic information of the patient.

In the medical device, the ECG data, the physiologic data, and the at least one of the medical history and demographic information of the patient may include a plurality of patient parameters that are input to the first risk assessment process associated with the first clinical condition of the patient. In the medical device, the at least one processor may be further configured to execute the first risk assessment process by identifying one or more associations between the first clinical condition and one or more patient parameters of the plurality of patient parameters and analyzing the one or more patient parameters of the plurality of patient parameters to generate the first risk estimate of deterioration of the patient. The first risk assessment process may be configured to analyze the one or more patient parameters of the plurality of patient parameters at least in part by applying distinct weights to respective patient parameters of the one or more patient parameters. The plurality of patient parameters may include one or more of patient ECG metrics, patient lung fluid level parameters, patient heart rate parameters, patient heart rate variability parameters, parameters of one or more arrhythmias experienced by the patient, patient cardio-vibrational parameters, patient respiratory rate parameters, patient pulse oxygen parameters, patient motion parameters, patient pallor parameters, and patient neurological condition parameters. In the medical device, the first risk assessment process may be configured to analyze the one or more patient parameters at least in part by comparing each patient parameter of the one or more patient parameters to one or more of a set of patient baseline parameters and a set of population benchmarks.

In the medical device, the at least one processor may be further configured to prompt the caregiver to input a subsequent patient assessment via the user interface and generate subsequent patient parameters based on the subsequent patient assessment. In the medical device, the subsequent patient assessment identifies a second clinical condition of the plurality of presentable clinical conditions and the at least one processor may be further configured to identify an association between the second clinical condition and a second risk assessment process of the plurality of risk assessment processes; execute the second risk assessment process to generate a second risk estimate of patient deterioration; compare the second risk estimate to a second clinical criterion of the plurality of clinical criteria, the second clinical criterion being associated with the second clinical condition; and generate a notification in response to the second risk estimate being outside the second clinical criterion. In the medical device, the memory may further store a model configured to determine a trajectory of a clinical condition of the patient, and the least one processor may be further configured to generate updated ECG data from ECG signals acquired subsequent to execution of the first risk assessment process; generate updated physiologic data from the one or more physiologic signals acquired subsequent to execution of the first risk assessment process; generate the trajectory of the clinical condition of the patient at least in part by executing a machine learning model using the first clinical condition, the first risk estimate of deterioration of the patient, and the updated ECG data and updated physiologic data; and generate a notification in response to the trajectory of the clinical condition of the patient indicating a risk of deterioration of the clinical condition of the patient.

In the medical device, the plurality of clinical criteria may include one or more of a range, a plurality of discrete elements, and a plurality of threshold values. In the medical device, the at least one processor may be further configured to determine the first clinical criterion at least in part by determining whether a current time falls within an established timeframe associated with reduced frequency of caregiver visits to the patient relative to other timeframes, and adjusting the first clinical criterion in response to determining that the current time falls within the established timeframe. The at least one processor may be further configured to re-execute the first risk assessment process according to a schedule and decrease a span of time between scheduled re-executions of the first risk assessment process in response to the first risk estimate being outside the first clinical criterion and thereby indicating an increased risk of deterioration of the patient. The at least one processor may be further configured to execute a neurologic assessment of the patient in response to the first risk estimate being outside the first clinical criterion.

The medical device may be ambulatory, may be wearable, and may further include a housing including the at least one processor. In the medical device, the first risk estimate may indicate a risk of rapid patient deterioration within a period of time including one or more of less than 1 hour, 1-2 hours, 2-4 hours, 4-6 hours, 6-8 hours, 8-12 hours, and 12-24 hours. The period of time of less than 1 hour can be, for example, 1 minute to 1 hour, 5 minutes to 1 hour, 10 minutes to 1 hour, or 15 minutes to 1 hour. The rapid patient deterioration may include one or more of a continuous decline in patient health spanning the period of time and a steep decline in patient health falling within the period of time.

According to another example, a method of assessing risk of patient deterioration in an in-patient hospital environment using a medical device is provided. The method includes acts of storing data identifying a plurality of presentable clinical conditions, a plurality of risk assessment processes associated with the plurality of presentable clinical conditions, and a corresponding plurality of clinical criteria associated with the plurality of risk assessment processes; acquiring electrocardiogram (ECG) signals from a patient; acquiring one or more physiologic signals from the patient; generating ECG data over a predetermined period of time based on the acquired ECG signals; generating physiologic data over the predetermined period of time based on the acquired one or more physiologic signals; determining at least one of medical history and demographic information of the patient; executing, by the medical device, a first risk assessment process associated with a first clinical condition selected from the plurality of presentable clinical conditions based the ECG data, the physiologic data, and the at least one of medical history and demographic information of the patient to generate a first risk estimate of deterioration of the patient; and generating, by the medical device, a notification in response to the first risk estimate of deterioration of the patient being outside a first clinical criterion of the plurality of clinical criteria, the first clinical criterion being associated with the first clinical condition.

Implementations of such a method may include one or more of the following features.

The method may further include an act of identifying the at least one of medical history and demographic information via an interface. The method may further include acts of determining an initial patient assessment and identifying the first clinical condition based on the initial patient assessment. In the method, the act of storing the data identifying the plurality of presentable clinical conditions may include an act of storing data identifying one or more of a heart failure condition, a post syncope condition, a post myocardial infarction condition, and a breathing disorder condition. The method may further include an act of identifying the first clinical condition based on an initial patient assessment of the ECG data, the physiologic data, and the at least one of medical history and demographic information of the patient.

In the method, the act of executing the first risk assessment process may include an act of receiving a plurality of patient parameters including the ECG data, the physiologic data, and the at least one of the medical history and demographic information of the patient. The act of executing the first risk assessment process may include acts of identifying one or more associations between the first clinical condition and one or more patient parameters of the plurality of patient parameters and analyzing the one or more patient parameters of the plurality of patient parameters to generate the first risk estimate of deterioration of the patient. The act of analyzing the one or more patient parameters of the plurality of patient parameters may include an act of applying distinct weights to respective patient parameters of the one or more patient parameters. The act of receiving the plurality of patient parameters may include an act of receiving one or more of patient ECG metrics, patient lung fluid level parameters, patient heart rate parameters, patient heart rate variability parameters, parameters of one or more arrhythmias experienced by the patient, patient cardio-vibrational parameters, patient respiratory rate parameters, patient pulse oxygen parameters, patient motion parameters, patient pallor parameters, and patient neurological condition parameters. The act of analyzing the one or more patient parameters may include an act of comparing each patient parameter of the one or more patient parameters to one or more of a set of patient baseline parameters and a set of population benchmarks.

The method may further include acts of determining a subsequent patient assessment and identifying subsequent patient parameters based on the subsequent patient assessment. In the method, the act of determining the subsequent patient assessment may include an act of identifying a second clinical condition of the plurality of presentable clinical conditions, and the method may further include acts of executing a second risk assessment process associated with the second clinical condition to generate a second risk estimate of patient deterioration; comparing the second risk estimate to a second clinical criterion of the plurality of clinical criteria, the second clinical criterion being associated with the second clinical condition; and generating a notification in response to the second risk estimate being outside the second clinical criterion.

The method may further include acts of storing a model configured to determine a trajectory of the clinical condition of the patient; generating updated ECG data from ECG signals acquired subsequent to execution of the first risk assessment process; generating updated physiologic data from the one or more physiologic signals acquired subsequent to execution of the first risk assessment process; generating a trajectory of a clinical condition of the patient at least in part by executing a machine learning model using the first clinical condition, the first risk estimate of deterioration of the patient, and the updated ECG data and updated physiologic data; and generating a notification in response to the trajectory of the clinical condition of the patient indicating a risk of deterioration of the clinical condition of the patient.

In the method, the act of storing the data identifying the plurality of clinical criteria may include an act of storing data identifying one or more of a range, a plurality of discrete elements, and a plurality of threshold values. In the method, the act of determining the first clinical criterion may include acts of determining whether a current time falls within an established timeframe associated with reduced frequency of caregiver visits to the patient relative to other timeframes and adjusting the first clinical criterion in response to determining that the current time falls within the established timeframe. The method may further include acts of re-executing the first risk assessment process according to a schedule and decreasing a span of time between scheduled re-executions of the first risk assessment process in response to the first risk estimate being outside the first clinical criterion and thereby indicating an increased risk of deterioration of the clinical condition of the patient.

The method may further include an act of performing a neurologic assessment of the patient in response to the first risk estimate being outside the first clinical criterion. In the method, the act of executing the first risk assessment process may include an act of executing a first risk assessment process that indicates a risk of rapid patient deterioration within a period of time including one or more of less than 1 hour, 1-2 hours, 2-4 hours, 4-6 hours, 6-8 hours, 8-12 hours, and 12-24 hours. The period of time of less than 1 hour can be, for example, 1 minute to 1 hour, 5 minutes to 1 hour, 10 minutes to 1 hour, or 15 minutes to 1 hour. The act of executing the first risk assessment process may further include an act of executing a first risk assessment process that indicates a risk of rapid patient deterioration including one or more of a continuous decline in patient health spanning the period of time and a steep decline in patient health falling within the period of time.

In another example, a medical system for assessing patient deterioration in an in-patient hospital environment is provided. The system includes an in-hospital medical device, a server located remotely from the in-hospital medical device. The in-hospital medical device includes a memory, a network interface coupled to a network, a plurality of sensing electrodes, one or more physiologic sensors, and at least one processor coupled to the memory, the network interface, the plurality of sensing electrodes, and the one or more physiologic sensors. The plurality of sensing electrodes is configured to couple externally to a skin of a patient and to acquire electrocardiogram (ECG) signals. The one or more physiologic sensors are configured to couple externally to the patient and configured to acquire one or more physiologic signals. The at least one processor is configured to generate ECG data over a predetermined period of time based on the ECG signals; generate physiologic data over the predetermined period of time based on the one or more physiologic signals; and transmit the ECG data and the physiologic data via the network interface. The server includes server memory, a server network interface coupled to the network, and one or more processors coupled to the server memory and the server network interface. The server memory stores data identifying a plurality of presentable clinical conditions, a plurality of risk assessment processes associated with the plurality of presentable clinical conditions, and a corresponding plurality of clinical criteria associated with the plurality of risk assessment processes. The one or more processors coupled to the server memory and the server network interface are configured to receive the ECG data and the physiologic data via the server network interface and the network; receive at least one of medical history and demographic information of the patient; execute a first risk assessment process associated with a first clinical condition based the ECG data, the physiologic data, and the at least one of medical history and demographic information of the patient to generate a first risk estimate of deterioration of the patient; and generate a notification in response to the first risk estimate of deterioration of the patient being outside a first clinical criterion of the plurality of clinical criteria, the first clinical criterion being associated with the first clinical condition.

Implementations of such a medical system may include one or more of the following features.

The system may further include a user interface coupled to the one or more processors, wherein the one or more processors may be further configured to receive the at least one of medical history and demographic information via the user interface. In the system, the one or more processors may be configured to receive, via the user interface, an initial patient assessment and identify the first clinical condition based on the initial patient assessment. The one or more processors may be further configured to receive the at least one of medical history and demographic information via the server network interface. In the system, the plurality of presentable clinical conditions may include one or more of a heart failure condition, a post syncope condition, a post myocardial infarction condition, and a breathing disorder condition. In the system, the one or more processors may be configured to automatically identify the first clinical condition based on initial patient assessment of the ECG data, the physiologic data, and the at least one of medical history and demographic information of the patient.

In the system, the ECG data, the physiologic data, and the at least one of the medical history and demographic information of the patient may include a plurality of patient parameters that are input to the first risk assessment process associated with the first clinical condition of the patient. In the system, the one or more processors may be configured to execute the first risk assessment process by identifying one or more associations between the first clinical condition and one or more patient parameters of the plurality of patient parameters, and analyzing the one or more patient parameters of the plurality of patient parameters to generate the first risk estimate of the clinical condition of the patient. The first risk assessment process may be configured to analyze the one or more patient parameters of the plurality of patient parameters at least in part by applying distinct weights to respective patient parameters of the one or more patient parameters. The plurality of patient parameters may include one or more of patient ECG metrics, patient lung fluid level parameters, patient heart rate parameters, patient heart rate variability parameters, parameters of one or more arrhythmias experienced by the patient, patient cardio-vibrational parameters, patient respiratory rate parameters, patient pulse oxygen parameters, patient motion parameters, patient pallor parameters, and patient neurological condition parameters. The first risk assessment process may be configured to analyze the one or more patient parameters at least in part by comparing each patient parameter of the one or more patient parameters to one or more of a set of patient baseline parameters and a set of population benchmarks.

The system may further include a user interface coupled to the one or more processors and the one or more processors may be further configured to prompt the caregiver to input a subsequent patient assessment via the user interface and generate subsequent patient parameters based on the subsequent patient assessment. The subsequent patient assessment may identify a second clinical condition of the plurality of presentable clinical conditions and the one or more processors may be further configured to identify an association between the second clinical condition and a second risk assessment process of the plurality of risk assessment processes; execute the second risk assessment process to generate a second risk estimate of patient deterioration; compare the second risk estimate to a second clinical criterion of the plurality of clinical criteria, the second clinical criterion being associated with the second clinical condition; and generate a notification in response to the second risk estimate being outside the second clinical criterion.

In the system, the server memory may further store a model configured to determine a trajectory of the clinical condition of the patient, and the one or more processors may be further configured to generate updated ECG data from ECG signals acquired subsequent to execution of the first risk assessment process; generate updated physiologic data from the one or more physiologic signals acquired subsequent to execution of the first risk assessment process; generate the trajectory of the clinical condition of the patient at least in part by executing the machine learning model using the first clinical condition, the first risk estimate of the clinical condition of the patient, and the updated ECG data and updated physiologic data; and generate a notification in response to the trajectory of the clinical condition of the patient indicating a risk of deterioration of the clinical condition of the patient.

In the system, the plurality of clinical criteria may include one or more of a range, a plurality of discrete elements, and a plurality of threshold values. In the system, the one or more processors may be configured to determine the first clinical criterion at least in part by determining whether a current time falls within an established timeframe associated with reduced frequency of caregiver visits to the patient relative to other timeframes, and adjusting the first clinical criterion in response to determining that the current time falls within the established timeframe. The one or more processors may be further configured to re-execute the first risk assessment process according to a schedule and to decrease a span of time between scheduled re-executions of the first risk assessment process in response to the first risk estimate being outside the first clinical criterion and thereby indicating an increased risk of deterioration of the clinical condition of the patient. The one or more processors may be further configured to execute a neurologic assessment of the patient in response to the first risk estimate being outside the first clinical criterion. In the system, the medical device may be ambulatory, may be wearable and may further include a housing including the at least one processor.

In another example, a medical device for assessing risk of patient deterioration in an in-patient hospital environment is provided. The medical device includes a memory, a plurality of sensing electrodes, one or more physiologic sensors, and at least one processor coupled to the memory, the plurality of sensing electrodes, and the one or more physiologic sensors. The memory stores data identifying a plurality of presentable clinical conditions, a plurality of risk assessment processes associated with the plurality of presentable clinical conditions, and a corresponding plurality of clinical criteria associated with the plurality of risk assessment processes. The plurality of sensing electrodes is configured to couple externally to a skin of a patient and to acquire electrocardiogram (ECG) signals. The one or more physiologic sensors are configured to couple externally to the patient and configured to acquire one or more physiologic signals. The at least one processor is configured to automatically determine and receive initial patient assessment data identifying a first clinical condition of the patient from the plurality of presentable clinical conditions; generate a robust set of patient parameters using the ECG signals, the physiologic signals and the initial patient assessment data, the robust set of patient parameters including a) continuously monitored patient parameters, b) periodically monitored patient parameters, and c) irregularly monitored patient parameters; execute a first risk assessment process associated with the first clinical condition of the patient using the data descriptive of the robust set of patient parameters to generate a first risk estimate of the clinical condition of the patient; re-execute the first risk assessment process associated with the first clinical condition using a subset of the robust set of patient parameters to update the first risk estimate to a second risk estimate of the clinical condition of the patient; and/or generate a notification in response to either the first risk estimate or the second risk estimate being outside a clinical criterion of the plurality of clinical criteria, the clinical criterion being associated with the first clinical condition.

Implementations of such a medical device may include one or more of the following features.

The medical device may further include a user interface coupled to the at least one processor, wherein the at least one processor may be further configured to receive at least one of medical history and demographic information via the user interface. In the medical device, the at least one processor may be configured to receive, via the user interface, an initial patient assessment and identify the first clinical condition based on the initial patient assessment. The medical device may further include a network interface coupled to the at least one processor and the at least one processor may be further configured to receive at least one of medical history and demographic information via the network interface. The network interface may be configured to communicate with one or more of a personal electronic device using near-field communication and a cloud server using Ethernet communication.

In the medical device, the plurality of presentable clinical conditions may include one or more of a heart failure condition, a post syncope condition, a post myocardial infarction condition, and a breathing disorder condition. In the medical device, the at least one processor may be configured to automatically identify the first clinical condition based on initial patient assessment of the ECG data, the physiologic data, and at least one of medical history and demographic information of the patient. In the medical device, the ECG data, the physiologic data, and at least one of medical history and demographic information of the patient may include a plurality of patient parameters that are input to the first risk assessment process associated with the first clinical condition of the patient.

In the medical device, the at least one processor may be configured to execute the first risk assessment process by identifying one or more associations between the first clinical condition and one or more patient parameters of the plurality of patient parameters, and analyzing the one or more patient parameters of the plurality of patient parameters to generate the first risk estimate of the clinical condition of the patient. The first risk assessment process may be configured to analyze the one or more patient parameters of the plurality of patient parameters at least in part by applying distinct weights to respective patient parameters of the one or more patient parameters.

In the medical device, the plurality of patient parameters may include one or more of patient ECG metrics, patient lung fluid level parameters, patient heart rate parameters, patient heart rate variability parameters, parameters of one or more arrhythmias experienced by the patient, patient cardio-vibrational parameters, patient respiratory rate parameters, patient pulse oxygen parameters, patient motion parameters, patient pallor parameters, and patient neurological condition parameters. In the medical device, the first risk assessment process may be configured to analyze the one or more patient parameters at least in part by comparing each patient parameter of the one or more patient parameters to one or more of a set of patient baseline parameters and a set of population benchmarks.

The medical device may include a user interface coupled to the at least one processor and the at least one processor may be further configured to prompt the caregiver to input a subsequent patient assessment via the user interface and generate subsequent patient parameters based on the subsequent patient assessment. The subsequent patient assessment may identify a second clinical condition of the plurality of presentable clinical conditions and the at least one processor may be further configured to identify an association between the second clinical condition and a second risk assessment process of the plurality of risk assessment processes; execute the second risk assessment process to generate a second risk estimate of patient deterioration; compare the second risk estimate to a second clinical criterion of the plurality of clinical criteria, the second clinical criterion being associated with the second clinical condition; and generate a notification in response to the second risk estimate being outside the second clinical criterion. The memory may further store a model configured to determine a trajectory of the clinical condition of the patient, and the least one processor may be further configured to generate updated ECG data from ECG signals acquired subsequent to execution of the first risk assessment process; generate updated physiologic data from the one or more physiologic signals acquired subsequent to execution of the first risk assessment process; generate the trajectory of the clinical condition of the patient at least in part by executing the machine learning model using the first clinical condition, the first risk estimate of the clinical condition of the patient, and the updated ECG data and updated physiologic data; and generate a notification in response to the trajectory of the clinical condition of the patient indicating a risk of deterioration of the clinical condition of the patient.

In the medical device, the plurality of clinical criteria may include one or more of a range, a plurality of discrete elements, and a plurality of threshold values. In the medical device, the at least one processor may be configured to determine the first clinical criterion at least in part by determining whether a current time falls within an established timeframe associated with reduced frequency of caregiver visits to the patient relative to other timeframes, and adjusting the first clinical criterion in response to determining that the current time falls within the established timeframe. In the medical device, the at least one processor may be further configured to re-execute the first risk assessment process according to a schedule, and decrease a span of time between scheduled re-executions of the first risk assessment process in response to the first risk estimate being outside the first clinical criterion and thereby indicating an increased risk of deterioration of the clinical condition of the patient.

In the medical device, the at least one processor may be further configured to execute a neurologic assessment of the patient in response to the first risk estimate being outside the first clinical criterion. The medical device may be ambulatory, may be wearable, and may further include a housing including the at least one processor. In the medical device, the irregularly monitored patient parameters may include one or more of medical history of the patient, demographic information about the patient, and discrete events regarding the patient. In the medical device, the at least one processor may be configured to re-execute the first risk assessment process subsequent to generation of the first risk estimate. In the medical device, the subset may include continuously monitored patient parameters, periodically monitored patient parameters, irregularly monitored patient parameters or combinations of continuously monitored patient parameters, periodically monitored patient parameters, and irregularly monitored patient parameters.

In another example, a method of assessing risk of patient deterioration in an in-patient hospital environment using a medical device is provided. The method includes acts of storing data identifying a plurality of presentable clinical conditions, a plurality of risk assessment processes associated with the plurality of presentable clinical conditions, and a corresponding plurality of clinical criteria associated with the plurality of risk assessment processes; acquiring electrocardiogram (ECG) signals from a patient; acquiring one or more physiologic signals from the patient; determining initial patient assessment data identifying a first clinical condition of the patient from the plurality of presentable clinical conditions; creating a robust set of patient parameters using the ECG signals, the physiologic signals and the initial patient assessment data, the robust set of patient parameters comprising a) continuously monitored patient parameters, b) periodically monitored patient parameters, and c) irregularly monitored patient parameters; executing, by the medical device, a first risk assessment process associated with the first clinical condition of the patient using the data descriptive of the robust set of patient parameters to generate a first risk estimate of the clinical condition of the patient; re-executing, by the medical device, the first risk assessment process associated with the first clinical condition using a subset of the robust set of patient parameters to update the first risk estimate to a second risk estimate of the clinical condition of the patient; and generating, by the medical device, a notification in response to either the first risk estimate or the second risk estimate being outside a clinical criterion of the plurality of clinical criteria, the clinical criterion being associated with the first clinical condition.

Implementations of such a method may include one or more of the following features.

The method may further include an act of identifying at least one of medical history and demographic information. The method may further include acts of determining an initial patient assessment and identifying the first clinical condition based on the initial patient assessment.

In the method, the act of storing the data identifying the plurality of presentable clinical conditions may include an act of storing data identifying one or more of a heart failure condition, a post syncope condition, a post myocardial infarction condition, and a breathing disorder condition.

The method may further include an act of identifying the first clinical condition based on an initial patient assessment of the ECG data, the physiologic data, and at least one of medical history and demographic information of the patient.

In the method, the act of executing the first risk assessment process may include an act of receiving a plurality of patient parameters comprising the ECG data, the physiologic data, and at least one of medical history and demographic information of the patient. The act of executing the first risk assessment process may include acts of identifying one or more associations between the first clinical condition and one or more patient parameters of the plurality of patient parameters; and analyzing the one or more patient parameters of the plurality of patient parameters to generate the first risk estimate of the clinical condition of the patient. The act of analyzing the one or more patient parameters of the plurality of patient parameters may include an act of applying distinct weights to respective patient parameters of the one or more patient parameters. The act of receiving the plurality of patient parameters may include an act of receiving one or more of patient ECG metrics, patient lung fluid level parameters, patient heart rate parameters, patient heart rate variability parameters, parameters of one or more arrhythmias experienced by the patient, patient cardio-vibrational parameters, patient respiratory rate parameters, patient pulse oxygen parameters, patient motion parameters, patient pallor parameters, and patient neurological condition parameters. The act of analyzing the one or more patient parameters may include an act of comparing each patient parameter of the one or more patient parameters to one or more of a set of patient baseline parameters and a set of population benchmarks.

The method may further include acts of determining a subsequent patient assessment; and identifying subsequent patient parameters based on the subsequent patient assessment.

In the method, the act of determining the subsequent patient assessment may include an act of identifying a second clinical condition of the plurality of presentable clinical conditions.

The method may further include acts of executing a second risk assessment process associated with the second clinical condition to generate a second risk estimate of patient deterioration; comparing the second risk estimate to a second clinical criterion of the plurality of clinical criteria, the second clinical criterion being associated with the second clinical condition; and generating a notification in response to the second risk estimate being outside the second clinical criterion. The method may further include acts of storing a model configured to determine a trajectory of the clinical condition of the patient; generating updated ECG data from ECG signals acquired subsequent to execution of the first risk assessment process; generating updated physiologic data from the one or more physiologic signals acquired subsequent to execution of the first risk assessment process; generating a trajectory of a clinical condition of the patient at least in part by executing a machine learning model using the first clinical condition, the first risk estimate of the clinical condition of the patient, and the updated ECG data and updated physiologic data; and generating a notification in response to the trajectory of the clinical condition of the patient indicating a risk of deterioration of the clinical condition of the patient.

In the method, the act of storing the data identifying the plurality of clinical criteria may include an act of storing data identifying one or more of a range, a plurality of discrete elements, and a plurality of threshold values. In the method, determining the first clinical criterion may include acts of determining whether a current time falls within an established timeframe associated with reduced frequency of caregiver visits to the patient relative to other timeframes and adjusting the first clinical criterion in response to determining that the current time falls within the established timeframe.

The method may further include acts of re-executing the first risk assessment process according to a schedule; and decreasing a span of time between scheduled re-executions of the first risk assessment process in response to the first risk estimate being outside the first clinical criterion and thereby indicating an increased risk of deterioration of the clinical condition of the patient. The method may further include an act of performing a neurologic assessment of the patient in response to the first risk estimate being outside the first clinical criterion.

In the method, the act of creating a robust set of patient parameters may include an act of creating a robust set of patient parameters comprising a) continuously monitored patient parameters, b) periodically monitored patient parameters, and c) irregularly monitored patient parameters comprising one or more of medical history of the patient, demographic information about the patient, and discrete events regarding the patient.

The method may further include acts of re-executing the first risk assessment process subsequent to generation of the first risk estimate.

In the method, the act of re-executing the first risk assessment process associated with the first clinical condition may include an act of re-executing the first risk assessment process associated with the first clinical condition using a subset of the robust set of patient parameters, consisting of continuously monitored patient parameters, periodically monitored patient parameters, irregularly monitored patient parameters or combinations of continuously monitored patient parameters, periodically monitored patient parameters, and irregularly monitored patient parameters, to update the first risk estimate to a second risk estimate of the clinical condition of the patient.

In another example, a medical device for assessing patient deterioration in an in-patient hospital environment is provided. The medical device includes a memory, a plurality of sensing electrodes, one or more physiologic sensors, and at least one processor coupled to the memory, the plurality of sensing electrodes, and the one or more physiologic sensors. The memory stores data identifying a plurality of presentable clinical conditions, a plurality of risk assessment processes associated with the plurality of presentable clinical conditions, and a corresponding plurality of clinical criteria associated with the plurality of risk assessment processes. The plurality of sensing electrodes is configured to couple externally to a skin of a patient and to acquire electrocardiogram (ECG) signals. The one or more physiologic sensors are configured to couple externally to the patient and configured to acquire one or more physiologic signals. The at least one processor is configured to at least one of automatically determine and receive initial patient assessment data identifying a first clinical condition of the patient from the plurality of presentable clinical conditions; execute a first risk assessment process associated with the first clinical condition at predetermined intervals of time based on the ECG data, the physiologic data, and the initial patient assessment data to generate a first plurality of risk estimates of the first clinical condition of the patient; establish a first trajectory of the first clinical condition of the patient over time based on all or a portion of the ECG data, the physiologic data, and the initial patient assessment data; and execute an action based on a deviation from the established first trajectory of the first clinical condition of the patient.

Implementations of such a medical device may include one or more of the following features.

In the medical device, the action may include issuing a notification to a caregiver. The action may include setting a flag stored in memory that indicates the deviation.

The medical device may further include a user interface coupled to the at least one processor. The action may include prompting a user to input data descriptive of at least one patient parameter.

In the medical device, the at least one processor may be configured to establish the first trajectory of the first clinical condition of the patient based on the first plurality of risk estimates of the first clinical condition of the patient. The ECG data, the physiologic data, and the at least one of the medical history and demographic information of the patient may include a plurality of patient parameters that are input to the first risk assessment process associated with the first clinical condition of the patient. The at least one processor may be configured to execute the first risk assessment process by identifying one or more associations between the first clinical condition and one or more patient parameters of the plurality of patient parameters and analyzing the one or more patient parameters of the plurality of patient parameters to generate the first risk estimate of the clinical condition of the patient. The first risk assessment process may be configured to analyze the one or more patient parameters of the plurality of patient parameters at least in part by applying distinct weights to respective patient parameters of the one or more patient parameters. The plurality of patient parameters may include one or more of patient ECG metrics, patient lung fluid level parameters, patient heart rate parameters, patient heart rate variability parameters, parameters of one or more arrhythmias experienced by the patient, patient cardio-vibrational parameters, patient respiratory rate parameters, patient pulse oxygen parameters, patient motion parameters, patient pallor parameters, and patient neurological condition parameters.

In the medical device, the at least one processor may be further configured to at least one of automatically determine and receive second patient assessment data identifying a second clinical condition different from the first clinical condition of the patient; execute a second risk assessment process associated with the second clinical condition of the patient at other predetermined intervals of time based on the on the ECG data, the physiologic data, and the second patient assessment data to generate a second plurality of risk estimates of the second clinical condition of the patient; and establish a second trajectory of the second clinical condition of the patient over time based on the second plurality of risk estimates of the second clinical condition of the patient. The plurality of presentable clinical conditions may include one or more of a heart failure condition, a post syncope condition, a post myocardial infarction condition, and a breathing disorder condition. The at least one processor may be further configured to execute the first risk assessment process at least in part by executing an enhanced Kalman filter. The enhanced Kalman filter may implement a plurality of loops, each loop of the plurality of loops tracking and generating actual and predicted values of a distinct set of patient parameters according to a different update period. The at least one processor may be configured to calculate the trajectory using actual and predicted values of patient parameters. The first trajectory may include an ensemble trajectory. The at least one processor may be further configured to store the ECG data, the physiologic data, and the initial patient assessment data in a vector. The vector may include a first portion, a second portion, and a third portion and the at least one processor may be further configured to update the first portion of the vector continuously; update the second portion of the vector is updated periodically; and update the third portion of the vector is update irregularly.

In another example, a method for assessing risk of patient deterioration in an in-patient hospital environment using a medical device is provided. The method includes acts of storing data identifying a plurality of presentable clinical conditions, a plurality of risk assessment processes associated with the plurality of presentable clinical conditions, and a corresponding plurality of clinical criteria associated with the plurality of risk assessment processes; acquiring electrocardiogram (ECG) signals from a patient; acquiring one or more physiologic signals from the patient; generating ECG data over a predetermined period of time based on the acquired ECG signals; generating physiologic data over the predetermined period of time based on the acquired one or more physiologic signals; determining initial patient assessment data identifying a first clinical condition of the patient from the plurality of presentable clinical conditions; executing, by the medical device, a first risk assessment process associated with the first clinical condition at predetermined intervals of time based on the ECG data, the physiologic data, and the initial patient assessment data to generate a first plurality of risk estimates of the first clinical condition of the patient; establishing, by the medical device, a first trajectory of the first clinical condition of the patient over time based on all or a portion of the ECG data, the physiologic data, and the initial patient assessment data; and executing an action based on a deviation from the established first trajectory of the first clinical condition of the patient.

Implementations of such a method may include one or more of the following features.

In the method, the act of executing the action may include an act of notifying to a caregiver. The act of executing the action may include an act of recording the deviation. The act of executing the action may include an act of determining at least one patient parameter. The act of establishing the first trajectory of the first clinical condition of the patient may include act of establishing the first trajectory based on the first plurality of risk estimates of the first clinical condition of the patient. The act of executing the first risk assessment process may include an act of receiving a plurality of patient parameters comprising the ECG data, the physiologic data, and the at least one of the medical history and demographic information of the patient. The act of executing the first risk assessment process may include acts of identifying one or more associations between the first clinical condition and one or more patient parameters of the plurality of patient parameters; and analyzing the one or more patient parameters of the plurality of patient parameters to generate the first risk estimate of the clinical condition of the patient. The act of analyzing the one or more patient parameters of the plurality of patient parameters may include an act of applying distinct weights to respective patient parameters of the one or more patient parameters. The act of receiving the plurality of patient parameters may include an act of receiving one or more of patient ECG metrics, patient lung fluid level parameters, patient heart rate parameters, patient heart rate variability parameters, parameters of one or more arrhythmias experienced by the patient, patient cardio-vibrational parameters, patient respiratory rate parameters, patient pulse oxygen parameters, patient motion parameters, patient pallor parameters, and patient neurological condition parameters.

The method may further include acts of determining second patient assessment data identifying a second clinical condition different from the first clinical condition of the patient; executing a second risk assessment process associated with the second clinical condition of the patient at other predetermined intervals of time based on the ECG data, the physiologic data, and the second patient assessment data to generate a second plurality of risk estimates of the second clinical condition of the patient; and establishing a second trajectory of the second clinical condition of the patient over time based on the second plurality of risk estimates of the second clinical condition of the patient.

In the method, the act of storing the data identifying the plurality of presentable clinical conditions may include an act of storing data identifying one or more of a heart failure condition, a post syncope condition, a post myocardial infarction condition, and a breathing disorder condition. The act of executing the first risk assessment process may include an act of executing an enhanced Kalman filter. The act of executing the enhanced Kalman filter may include an act of executing a plurality of loops, each loop of the plurality of loops tracking and generating actual and predicted values of a distinct set of patient parameters according to a different update period. The act of establishing the first trajectory may include an act of calculating a first trajectory using actual and predicted values of patient parameters. The act of calculating the first trajectory may include an act of calculating an ensemble trajectory.

The method may further include an act of storing the ECG data, the physiologic data, and the initial patient assessment data in a vector. The method may further include acts of updating a first portion of the vector continuously; updating a second portion of the vector is updated periodically; and updating a third portion of the vector is update irregularly.

In another example, a medical device for assessing risk of patient deterioration in an in-patient hospital environment is provided. The medical device includes a memory, a plurality of sensing electrodes, one or more physiologic sensors distinct from the sending electrodes, and at least one processor coupled to the memory the plurality of sensing electrodes, and the one or more physiologic sensors. The memory stores data identifying a plurality of presentable clinical conditions, an indication, for each presentable clinical condition of the plurality of presentable clinical conditions, of whether the presentable clinical condition was presented at admission to the in-patient hospital environment or during transfer between departments in the in-patient hospital environment, a plurality of risk assessment processes associated with the plurality of presentable clinical conditions, and a corresponding plurality of clinical criteria associated with the plurality of risk assessment processes. The plurality of sensing electrodes is configured to couple externally to a skin of an in-hospital patient and to acquire electrocardiogram (ECG) signals. The one or more physiologic sensors are configured to couple externally to the in-hospital patient and to acquire one or more physiologic signals distinct from the ECG signals. The at least one processor is configured to generate ECG data over a predetermined period of time based on the ECG signals, generate physiologic data over the predetermined period of time based on the one or more physiologic signals, receive at least one of medical history and demographic information of the in-hospital patient, select a first clinical condition from the plurality of presentable clinical conditions based on the ECG data, the physiologic data, and the at least one of medical history and demographic information of the in-hospital patient, identify a first risk assessment process from the plurality of risk assessment processes, the first risk assessment process being associated with the first clinical condition selected from the plurality of presentable clinical conditions, execute the first risk assessment process to generate a first risk estimate of a rapid deterioration of the in-hospital patient within an upcoming time period, generate a notification comprising a likelihood that the in-hospital patient will require emergency medical intervention within the upcoming time period, the notification being generated in response to the first risk estimate of the rapid deterioration of the in-hospital patient being outside a first clinical criterion associated with the first clinical condition, and transmit the notification to at least one emergency responder within the in-patient hospital environment indicating that the in-hospital patient will require emergency medical intervention within the upcoming time period.

Implementations of such a medical device may include one or more of the following features.

In the medical device, the upcoming time period can include at least one of within less than 1 hour, within 1-2 hours, within 2-4 hours, within 4-6 hours, within 6-8 hours, within 8-12 hours, and within 12-24 hours. The at least one emergency responder can include at least one of an in-hospital medical emergency team (MET), a medical emergency response team (MERT), and an in-hospital rapid response team (RRT). The least one processor can be further configured to generate updated ECG data from ECG signals acquired subsequent to execution of the first risk assessment process; generate updated physiologic data from one or more physiologic signals acquired subsequent to execution of the first risk assessment process; generate a trajectory of the clinical condition of the in-hospital patient at least in part by analyzing the first clinical condition, the first risk estimate of the rapid deterioration of the in-hospital patient, and the updated ECG data and updated physiologic data; and generate an updated notification in response to the trajectory of the clinical condition of the in-hospital patient indicating an updated risk of rapid deterioration of the clinical condition of the in-hospital patient.

In the medical device, the at least one processor can be further configured to receive an initial patient assessment and identify the first clinical condition based on the initial patient assessment. The plurality of presentable clinical conditions can include one or more of a heart failure condition, a post syncope condition, a post myocardial infarction condition, and a breathing disorder condition. The at least one processor can be configured to automatically identify the first clinical condition based on an initial patient assessment of the ECG data, the physiologic data, and the at least one of medical history and demographic information of the in-hospital patient. The ECG data, the physiologic data, and the at least one of medical history and demographic information of the in-hospital patient can include a plurality of patient parameters that are input to the first risk assessment process associated with the first clinical condition of the in-hospital patient. The at least one processor can be further configured to execute the first risk assessment process by identifying one or more associations between the first clinical condition and one or more patient parameters of the plurality of patient parameters; and analyzing the one or more patient parameters of the plurality of patient parameters to generate the first risk estimate of the rapid deterioration of the in-hospital patient. The plurality of patient parameters can include one or more of patient ECG metrics, patient lung fluid level parameters, patient heart rate parameters, patient heart rate variability parameters, parameters of one or more arrhythmias experienced by the in-hospital patient, patient cardio-vibrational parameters, patient respiratory rate parameters, patient pulse oxygen parameters, patient motion parameters, patient pallor parameters, and patient neurological condition parameters.

In the medical device, the at least one processor can be further configured to re-execute the first risk assessment process according to a schedule; and decrease a span of time between scheduled re-executions of the first risk assessment process in response to the first risk estimate being outside the first clinical criterion and thereby indicating an increased risk of rapid deterioration of the in-hospital patient. The first risk estimate of a rapid deterioration of the in-hospital patient comprises one or more of a continuous decline in patient health spanning the upcoming time period and a steep decline in patient health falling within the upcoming time period. The medical device can be ambulatory, wearable and can further include a housing comprising the at least one processor.

In another example, a medical device for assessing patient deterioration in an in-patient hospital environment is provided. The medical device includes a memory, a plurality of sensing electrodes, one or more physiological sensors distinct from the plurality of sensing electrodes, and at least one processor coupled to the memory, the plurality of sensing electrodes, and the one or more physiologic sensors. The memory stores data identifying a plurality of presentable clinical conditions, an indication, for each presentable clinical condition of the plurality of presentable clinical conditions, of whether the presentable clinical condition was presented at admission to the in-patient hospital environment or during transfer between departments in the in-patient hospital environment, a plurality of risk assessment processes associated with the plurality of presentable clinical conditions, and a corresponding plurality of clinical criteria associated with the plurality of risk assessment processes. The plurality of sensing electrodes is configured to couple externally to a skin of an in-hospital patient and to acquire electrocardiogram (ECG) signals. The one or more physiologic sensors are distinct from the plurality of sensing electrodes, configured to couple externally to the in-hospital patient, and configured to acquire one or more physiologic signals distinct from the ECG signals. The at least one processor is configured to at least one of automatically determine and receive initial patient assessment data identifying a first clinical condition of the in-hospital patient from the plurality of presentable clinical conditions, execute a first risk assessment process associated with the first clinical condition at predetermined intervals of time based on ECG data generated from the ECG signals, physiologic data generated from the physiologic signals, and the initial patient assessment data to generate a first plurality of risk estimates of the first clinical condition of the in-hospital patient, establish a first trajectory of the first clinical condition of the in-hospital patient over an upcoming time period based on all or a portion of the ECG data, the physiologic data, and the initial patient assessment data, at least one of automatically determine and receive second patient assessment data identifying a second clinical condition of the plurality of presentable clinical conditions different from the first clinical condition of the in-hospital patient, execute a second risk assessment process associated with the second clinical condition of the in-hospital patient at other predetermined intervals of time based on the ECG data, the physiologic data, and the second patient assessment data to generate a second plurality of risk estimates of the second clinical condition of the in-hospital patient, and change from the first trajectory to a second trajectory of the second clinical condition of the in-hospital patient over the upcoming time period based on or a portion of the ECG data, the physiologic data, and the initial patient assessment data, determine whether the in-hospital patient is likely to require emergency medical intervention within the upcoming time period based on one of the first trajectory and the second trajectory, and if the in-hospital patient is likely to require emergency medical intervention generate a notification indicating a likelihood that the in-hospital patient will require emergency medical intervention within the upcoming time period, and transmit the notification to at least one emergency responder.

Implementations of such a medical device may include one or more of the following features.

In the medical device, the at least one emergency responder can include at least one of an in-hospital medical emergency team (MET), a medical emergency response team (MERT), and an in-hospital rapid response team (RRT). The at least one processor can be further configured to set a flag stored in memory that indicates the in-hospital patient is likely to require emergency medical intervention within the upcoming time period. The at least one processor can be configured to establish the first trajectory of the first clinical condition of the in-hospital patient based on the first plurality of risk estimates of the first clinical condition of the in-hospital patient. The ECG data, the physiologic data, and the at least one of a medical history and demographic information of the in-hospital patient can include a plurality of patient parameters that are input to the first risk assessment process associated with the first clinical condition of the in-hospital patient. The at least one processor can be further configured to execute the first risk assessment process by identifying one or more associations between the first clinical condition and one or more patient parameters of the plurality of patient parameters; and analyzing the one or more patient parameters of the plurality of patient parameters to generate the first risk estimate of the clinical condition of the in-hospital patient. The first risk assessment process can be configured to analyze the one or more patient parameters of the plurality of patient parameters at least in part by applying distinct weights to respective patient parameters of the one or more patient parameters. The plurality of patient parameters comprises one or more of patient ECG metrics, patient lung fluid level parameters, patient heart rate parameters, patient heart rate variability parameters, parameters of one or more arrhythmias experienced by the in-hospital patient, patient cardio-vibrational parameters, patient respiratory rate parameters, patient pulse oxygen parameters, patient motion parameters, patient pallor parameters, and patient neurological condition parameters. The plurality of presentable clinical conditions comprises one or more of a heart failure condition, a post syncope condition, a post myocardial infarction condition, and a breathing disorder condition. The upcoming time period comprises within less than 1 hour, within 1-2 hours, within 2-4 hours, within 4-6 hours, within 6-8 hours, within 8-12 hours, and within 12-24 hours.

In another example, a medical device for assessing patient deterioration in an in-patient hospital environment is provided. The medical device includes a memory and at least one processor operably coupled to the memory. The memory stores data identifying a plurality of presentable clinical conditions, an indication, for each presentable clinical condition of the plurality of presentable clinical conditions, of whether the presentable clinical condition was presented at admission to the in-patient hospital environment or during transfer between departments in the in-patient hospital environment, a plurality of risk assessment processes associated with the plurality of presentable clinical conditions, and a corresponding plurality of clinical criteria associated with the plurality of risk assessment processes. The at least one processor is configured to at least one of automatically determine and receive initial patient assessment data identifying a first clinical condition of an in-hospital patient from the plurality of presentable clinical conditions, receive electrocardiogram (ECG) signals for the in-hospital patient, receive physiological signals distinct from the ECG signals for the in-hospital patient, execute a first risk assessment process associated with the first clinical condition at predetermined intervals of time based on ECG data generated from the ECG signals, physiologic data generated from the physiologic signals, and the initial patient assessment data to generate a first plurality of risk estimates of the first clinical condition of the in-hospital patient, establish a first trajectory of the first clinical condition of the in-hospital patient over an upcoming time period based on all or a portion of the ECG data, the physiologic data, and the initial patient assessment data, the upcoming time period comprising at least one of within less than 1 hour, within 1-2 hours, within 2-4 hours, within 4-6 hours, within 6-8 hours, within 8-12 hours, and within 12-24 hours, determine whether the in-hospital patient is likely to require emergency medical intervention within the upcoming time period, and if the in-hospital patient is likely to require emergency medical intervention generate a notification indicating a likelihood that the in-hospital patient will require emergency medical intervention within the upcoming time period, and transmit the notification to at least one emergency responder.

In the medical device, the at least one emergency responder can include at least one of an in-hospital medical emergency team (MET), a medical emergency response team (MERT), and an in-hospital rapid response team (RRT).

Still other aspects, examples, and advantages of these aspects and examples, are discussed in detail below. Moreover, it is to be understood that both the foregoing summary and the following detailed description are merely illustrations of various aspects and examples and are intended to provide an overview or framework for understanding the nature and character of the claimed aspects and examples. Any example disclosed herein may be combined with any other example. References to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1:
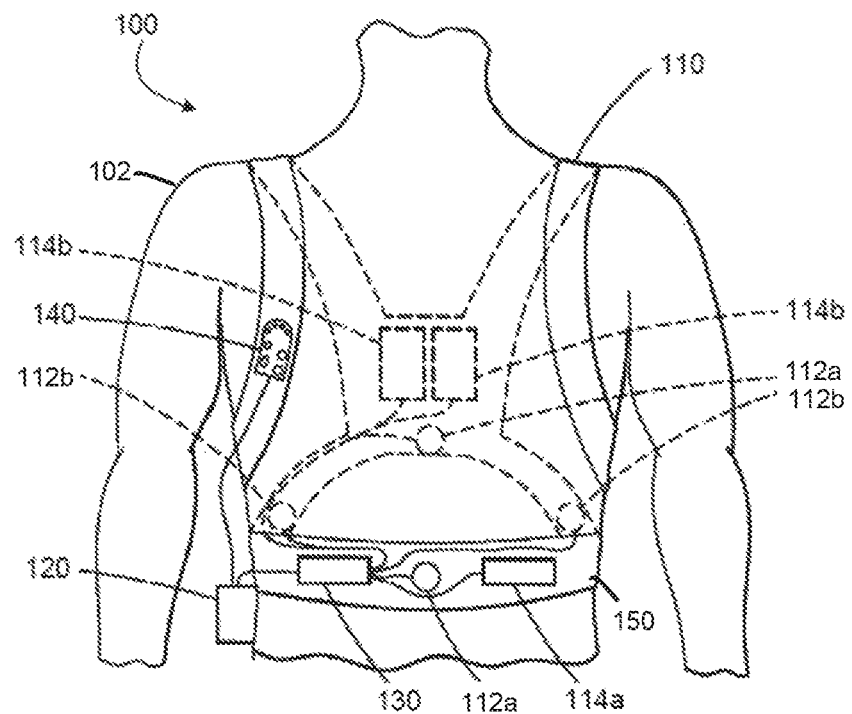
FIG. 1 depicts a wearable, ambulatory, external medical device in accordance with at least one example disclosed herein.

Patients presenting at hospitals with serious clinical conditions require substantial monitoring and care. To help guard against adverse events that may lead to fatal outcomes for these patients, early warning monitoring regimens can be implemented to generate an early warning score to alert caregivers to signs of deterioration. For example, such an early warning score may be a modified early warning score (MEWS) based on an array of observable patient parameters (such as the patient's blood pressure, heart rate, and temperature). The MEWS can be a periodic and easily determinable indicator of the patient's wellness that can be tracked over time. Where the MEWS trends unfavorably (indicating a deterioration of a patient's clinical condition), caregivers may take additional actions prescribed within the monitoring regimen. These actions may include observing the patient parameters more frequently and/or calling for assistance from other caregivers. In extremely unfavorable cases, actions taken by a monitoring caregiver may include summoning an emergency response medical team (MERT) made up of caregivers who are specially trained to treat a patient's clinical condition. For example, patients who go into cardiogenic shock may receive immediate triage and intervention with the development of protocols that stipulate that such patients be taken to a cardiac intensive care unit within the hospital. For example, a cardiac intensivist may rapidly evaluate the patient based on information from the various monitoring devices prior to activating a paging system calling into action a critical care cardiologist, an advanced heart disease specialist, a cardiac surgeon with expertise in extra-corporeal life support (ECLS) and ventricular assist device (VAD) implantation, and an interventional cardiologist who can provide short-term catheter-based interventions and mechanical circulatory support. In this manner, MERTs can reduce the risk of overt cardiopulmonary arrest and improve outcomes in patients who progressively and rapidly deteriorate or exhibiting clinical instability in the non-emergency department (non-ED) or non-ICU areas of the hospital by facilitating rapid, multi-disciplinary assessment and intervention.

Medical devices disclosed herein are designed to support the in-hospital monitoring regimens while, in some implementations, providing continuous protection against an adverse event such as sudden cardiac arrest. More specifically, these medical devices are configured to monitor in-hospital patients for deteriorating clinical conditions and to take any of a variety of actions in response to predicting and/or detecting a deteriorating clinical condition in a patient. In some applications, the medical devices herein can implement and present a MEWS to assist with triage. The clinical conditions monitored and the responsive actions taken by these medical devices based on a MEWS and/or other factors described herein can vary between examples. For instance, in some examples, the clinical conditions presentable by a patient and monitored by a medical device include heart failure conditions, post syncope conditions, post myocardial infarction conditions, and/or breathing disorder conditions. Also, in some examples, the actions taken by a medical device include alerting the patient or a caregiver, stimulating the patient, and/or otherwise treating the patient. In some instances, the caregiver alerted by the medical device may be a nurse or a member of a MERT, depending on the identity of the clinical condition and/or the magnitude and likelihood of the deterioration. Example benefits of such devices as disclosed herein include automated diagnostics minimizing human intervention, early warning for when a patient's risk of a serious adverse event rises that allows for closer monitoring of the patient, reduction of human error during medical examinations, and application of consistent caregiver standards and processes.

In some examples, prior to monitoring a patient for deteriorating clinical conditions, the medical device receives (e.g., manually entered via a user interface or in an automated manner from another device or system) patient parameters descriptive of the patient and the patient's medical history. These patient parameters may include irregularly generated or monitored parameters. For example, such irregularly generated or monitored parameters include patient medical history information, demographic information, family medical history information, past illnesses suffered, prior cardiac illnesses, prior arrhythmias, medications, height, and weight, among other information. Irregularly monitored parameters may further include a context in which the patient is being assessed. Examples of these patient assessment contexts include at admission, during transfers between locations/departments (e.g., emergency room, surgical room, recovery room, intensive care unit, etc.), during transfers between procedures (cardiac catheterization, surgery, etc.), during transfers between healthcare facilities, and/or other geographic or procedural contexts.

The patient parameters may include periodically generated or monitored parameters. For example, such periodically generated or monitored parameters include patient current clinical condition, awareness level, neurologic state parameters, patient pallor parameters, or patient parameters that rely on a periodic acquisition by a caregiver. The patient parameters may include continuously generated or monitored patient parameters such as body temperature, blood pressure, heart rate, or other patient parameter that can be automatically acquired by the medical device via one or more corresponding sensors disposed on the patient's body.

Examples of patient parameters descriptive of the patient's medical history may include identifiers of ongoing conditions (e.g., ischemic heart disease, diabetes, or chronic renal failure) and/or discrete episodes (angina, atrial tachycardia, ventricular tachycardia, myocardial infarction, etc.). Examples of patient parameters descriptive of the patient's demographics may include identifiers of age, gender, race, familial history, and the like. Patient parameters may be collected, for example, by a caregiver as part of the patient being admitted to a hospital or other healthcare facility. In some examples, the patient information includes an identifier, input by the caregiver, of a clinical condition presented by the patient. After receiving the patient parameters and being fitted to the patient, the medical device monitors the patient's clinical condition for predicted and/or actual deterioration.

In some examples, the medical device includes one or more sensors configured to acquire physiologic signals from the patient and uses these signals to monitor for predicted and/or actual deterioration. The sensors included and physiologic signals acquired vary between examples. For instance, in some examples, the sensors include electrodes, accelerometers, and photodetectors, among other sensors. Also, in some examples, the signals acquired include ECG signals, cardio-vibrational signals, and blood oxygenation signals, among other signals. In some instances, the medical device monitors for predicted and/or actual deterioration by continuously generating or monitoring patient parameters using the acquired signals. The patient parameters that may be continuously generated or monitored include ECG metrics, heart rate parameters, heart rate variability parameters, ectopic activation or contraction parameters, respiration rate parameters, blood oxygenation parameters, cardio-vibrational parameters, patient pallor parameters, muscle oxygenation parameters, cerebral oxygenation parameters, and lung fluid level parameters. For example, the ECG information may be combined with other non-ECG information as described herein to provide additional insight about the patient's condition. For instance, where the patient parameters include ectopy contraction parameters, information from an ultrasound sensor coupled to the patient can be considered for analyzing heart wall motion. Additionally or alternatively, cardio-vibrational analysis from one or more cardio-vibration sensors can be used to provide information regarding such parameters.

In some examples, the medical device is configured to execute periodic neurologic examinations of the patient and to generate at least one patient parameter based on the patient's performance. Subtle changes in neurologic function can be indicative of poor cerebral perfusion and/or early stage neurologic injury. If detected early, these transient decrements in function can be easily reversed. If not detected, decrements in perfusion can lead to permanent brain damage leading to incremental health-care costs within and outside of the hospital. As such, automated neurologic examinations by a wearable medical device are advantageous.

In some examples, to predict and/or detect deterioration, the medical device executes a risk assessment process that is initially tailored to the patient's current clinical condition. In these examples, the risk assessment process accesses a data structure that specifies an argument set of patient parameters, weights, and scoring criteria that the risk assessment process uses to generate a risk estimate of patient deterioration. The set of patient parameters may include one or more of the continuously generated or monitored parameters listed above, or other patient parameters.

In some examples, to predict and/or detect deterioration the medical device first executes a risk assessment process using a robust set of patient parameters. This robust set of patient parameters may include all or a majority of the patient parameters described above. For instance, the robust set of patient parameters may include irregularly updated parameters, periodically updated parameters, and/or continuously monitored parameters. In these examples, the medical device iteratively executes subsequent risk assessment processes using a subset of the robust set of patient parameters. This subset may include, for example, only patient parameters with values that have been updated since the previous iteration of the risk assessment process. Alternatively or additionally, the subset may include, for example, only patient parameters that fall within a specific frequency update (e.g., only the continuously monitored parameters, the periodically updated parameters, and/or the irregularly updated parameters).

In some examples, to predict and/or detect deterioration the medical device executes a risk assessment process that identifies a trajectory of a patient's clinical condition. Such a device can be advantageous in monitoring and/or treating in-hospital patients. For example, a busy emergency room hospital staff may initially assess a patient presenting with a syncope event as potentially having a cardiac-related condition that may have caused the syncope event. Such an initial assessment may be made at patient admission to the hospital. In some examples, the initial assessment may be made during transfer between hospital departments. For instance, the assessment can be made after surgery and prior to transfer of the patient to a post-surgical monitoring ward. For instance, the assessment may be made when the patient is moved from an intensive care unit (ICU) to a step down unit.

In implementations, the systems, device, and methods herein can prompt the caregiver to indicate the patient assessment context of the initial assessment of the patient. For example, the caregiver may be prompted to indicate, via a user interface on the device, when/where the assessment is being done: "When is this assessment being performed?" The caregiver may then be asked to select one of the following options via a user interface of the medical device: a) at admission, b) transfer from surgical ward, c) transfer from intensive care unit, d) other. After the caregiver enters this information, the device can prompt the patient to input other initial assessment information as described in further detail below. The response to such queries can be stored in a memory of the device.

Based on such an initial assessment, a caregiver can cause the medical device to assess a trajectory of the patient. For example, such trajectory includes an expected change in the patient's condition during an upcoming time period (e.g., over the next 8 hours). For example, the trajectory can be based on a plurality of predicted values of patient parameters that are updated when actual values of patient parameters are calculated at predetermined intervals over the duration of the upcoming time period. Thus, in some examples, the trajectory can be a plurality of predicted risk estimates based on the predicted values of the patient parameters. In addition, the trajectory can be updated as actual values of patient parameters become available to calculate actual risk estimates. In an example, a caregiver can cause the medical device to execute a risk assessment of the patient experiencing another syncope event in an upcoming time period. In certain implementations, the trajectory of the patient's clinical condition can include an analysis of the risk of a sudden or rapid patient deterioration that may require emergency medical intervention over an upcoming time period. For example, the trajectory can provide an indication of a rapid deterioration of the patient's condition within the next hour or within the next two hours. For example, the determination of the rapid deterioration can be made based on identifying that that trajectory of the patient is outside the clinical criteria associated with the initial clinical condition (in this example, syncope). Upon such an indication, the medical device can alert one or more emergency medical responders of the likelihood of the patient experiencing a rapid deterioration.

In some examples, the deviation from an expected trajectory may be due to a second, different underlying clinical condition and/or a misdiagnosis of the patient's initial condition at admission. For example, the patient admitted after experiencing a syncope event as described above can further experience respiratory distress six hours after being admitted. This respiratory distress can be directly input by a caregiver or can be detected by the device as a significant change in respiration rate (e.g., greater than 50% increase in respiration rate). In such an example, the medical device can automatically switch the patient to being monitored based on a different and/or updated set of parameters, e.g. parameters designed to assess the risk of rapid deterioration of the patient in regard to the respiratory distress. In some implementations, the device can provide an alert to a caregiver that the patient should also be monitored and assessed using the different set of parameters. Once approved by the caregiver, the device can begin to monitor the patient for potential deterioration in accordance with a second trajectory of the patient associated with respiratory distress. In examples, in response to such an alert, the caregiver may also cause the medical device to execute a risk assessment for the patient experiencing more severe respiratory distress in addition to executing the risk assessment for another syncope event as described above. In both assessments, trajectories for the patient's clinical conditions can be identified and analyzed to determine the likelihood that the patient will experience a rapid deterioration and require emergency medical intervention for either an adverse cardiac event or for respiratory distress.

Such devices, systems, and methods can be clinically advantageous by providing further support to a busy hospital staff in an automated manner. With minimal to no human intervention, such devices, systems, and methods can quickly update based on the latest available physiological and medical history information to provide life-critical notifications, alerts, and plans of action to caregivers and emergency teams. For example, the techniques, devices and systems disclosed herein can cut down the time it takes for an emergency team or caregiver to respond to rapid patient deterioration. In certain example scenarios, patients who are expected to rapidly deteriorate based on their current trajectories may be moved to specialized area(s) of the hospital. Rapid response teams or emergency personnel may be in a better position to rapidly respond within such area(s). In other example scenarios, hospital administration may assess the deployment of their personnel and resources to better provide care for patients who are already admitted, and further, determine where newly admitted patients may be located. Hospital administration can use the concepts herein to assess how many of their patients' conditions are at a higher level of criticality compared to those that are relatively stable. When a patient's condition changes rapidly and/or their trajectory is updated to indicate worsening condition, hospital staff can quickly respond by deploying additional personnel and resources as appropriate in order to allow for timely intervention before the patient's condition deteriorates further. In some cases, hospital administrators may use such information to assess a level of use of its personnel capacity and resources in deciding whether to admit new patients based on their initial clinical condition and associated trajectory.

In at least some of these prediction examples, the risk assessment process executes a tracking and prediction process that uses previous predictions and observations of patient parameters to increase its accuracy in predicting future observations. Further, these future observations are used to generate a risk estimate of patient deterioration in the future. For instance, in one example, the tracking and prediction process is based on an enhanced Kalman filter that corrects predictions of patient parameters in a manner that accounts for differences between previous predictions and actual observations corresponding to the previous predictions. Over several iterations, the risk assessment process generates a trajectory of a patient's clinical condition that includes past, present, and future risk estimates of patient deterioration. In some instances, the medical device may adjust the clinical condition of the patient based on this trajectory, and thereby alter the underlying set of patient parameters, weights, and scoring criteria used to generate the risk estimates of patient deterioration.

Examples of the medical device and processes discussed herein are not limited in application to the details of construction and the arrangement of components set forth in the following description or illustrated in the accompanying drawings. The medical device and processes are capable of implementation in other examples and of being practiced or of being carried out in various ways. Examples of specific implementations are provided herein for illustrative purposes only and are not intended to be limiting. In particular, acts, components, elements, and features discussed in connection with any one or more examples are not intended to be excluded from a similar role in any other examples.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated references is supplementary to that of this document; for irreconcilable inconsistencies, the term usage in this document controls.

The teachings of the present disclosure can be generally applied to external medical monitoring and/or treatment devices (e.g., devices that are not completely implanted within the patient's body). External medical devices can include, for example, ambulatory medical devices that are capable of and designed for moving with the patient as the patient goes about his or her daily routine. An example ambulatory medical device can be a wearable medical device (WMD) such as a wearable cardioverter defibrillator (WCD) or a wearable cardiac monitoring device configured for an in-patient hospital use. For example, such an in-hospital device may be an in-hospital wearable defibrillator, a short-term wearable cardiac monitoring and/or therapeutic device, mobile telemetry devices, and other similar wearable medical devices adapted for in-patient hospital use.

The wearable medical device is capable of continuous (e.g., substantially or nearly continuous) use by the patient. In some implementations, the continuous use may be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. For example, the wearable medical device can be configured to be worn by a patient for as many as 24 hours a day. In some implementations, the patient may remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, cardio-vibrational information, etc.) and/or non-cardiac information (e.g., blood oxygen, the patient's temperature, glucose levels, tissue fluid levels, and/or lung sounds). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, lung sounds (e.g., using microphones and/or accelerometers), breath sounds, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiologic function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

In some implementations, the medical device may be a patient monitoring device with no treatment or therapy functions. For example, such a patient monitoring device can include a cardiac monitoring device or a cardiac monitor that is configured to monitor one or more cardiac physiologic parameters of a patient, e.g., for remotely monitoring and/or diagnosing a condition of the patient. For example, such cardiac physiologic parameters may include a patient's electrocardiogram (ECG) information, cardio-vibrational (e.g., using accelerometers or microphones), and other related cardiac information. A cardiac monitoring device is a portable device that the patient can carry around as he or she goes about their routine within the hospital. The cardiac monitor may be configured to detect the patient's ECG through a plurality of cardiac sensing electrodes. For example, a cardiac monitor may be attached to a patient via at least three adhesive cardiac sensing electrodes disposed about the patient's torso. Such cardiac monitors are used in mobile cardiac telemetry (MCT) and/or continuous cardiac event monitoring applications, e.g., in patient populations reporting irregular cardiac symptoms and/or conditions. Example cardiac conditions can include atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. For example, such patients may be prescribed a cardiac monitor for an extended period of time, e.g., 10 to 30 days, or more. In some mobile cardiac telemetry applications, a portable cardiac monitor can be configured to substantially continuously monitor the patient for a cardiac anomaly, and when such an anomaly is detected, the monitor may automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom). The cardiac monitor can be configured to monitor physiologic parameters of the patient other than cardiac related parameters. For example, the cardiac monitor can be configured to monitor, for example, cardio-vibrational (e.g., using accelerometers or microphones), lung sounds, breath sounds, sleep related parameters (e.g., snoring, sleep apnea), tissue fluids, among others.

FIG. 1 illustrates an example medical device 100 that is external, ambulatory, and wearable by a patient 102 and configured to monitor the patient for indications of rapid deterioration. For example, the medical device 100 can be a non-invasive medical device configured to be located substantially external to the patient. Such a medical device 100 can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic stimulation pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., anterior/posterior ECG electrodes 112a and side/side ECG electrodes 112b), one or more therapy electrodes 114 (e.g. anterior therapy electrode 114a and posterior electrodes 114b), a medical device controller 120, a connection pod 130, a patient interface pod 140, a belt 150, or any combination of these. In some examples, at least some of the components of the medical device 100 can be configured to be affixed to the garment 110 (or in some examples, permanently integrated into the garment 110), which can be worn about the patient's torso.

The medical device controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The medical device controller 120 can be operatively coupled to the therapy electrodes 114. For example, the therapy electrodes 114 can also be assembled into the garment 110, or, in some implementations, the therapy electrodes 114 can be permanently integrated into the garment 110.

Component configurations other than those shown in FIG. 1 are possible. For example, the sensing electrodes 112 can be configured to be attached at various positions about the body of the patient 102. The sensing electrodes 112 can be operatively coupled to the medical device controller 120 through the connection pod 130. In some implementations, the sensing electrodes 112 can be adhesively attached to the patient 102. In some implementations, the sensing electrodes 112 and therapy electrodes 114 can be included on a single integrated patch and adhesively applied to the patient's body.

Example sensing electrodes 112 can include dry electrodes or conductive electrodes as described in further detail below. In some examples, the therapy electrodes 114 can also be configured to include sensors configured to detect ECG signals as well as other physiologic signals of the patient. The connection pod 130 can, in some examples, include a signal processor configured to amplify, filter, and digitize these cardiac signals prior to transmitting the cardiac signals to the medical device controller 120. One or more therapy electrodes 114 can be configured to deliver one or more therapeutic defibrillating shocks to the body of the patient 102 when the medical device 100 determines that such treatment is warranted based on the signals detected by the sensing electrodes 112 and processed by the medical device controller 120. Example therapy electrodes 114 can include conductive metal electrodes such as stainless-steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient.

Alternatively, the optional therapeutic elements can be deactivated (e.g., by means of a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device 100.

Figure 2:
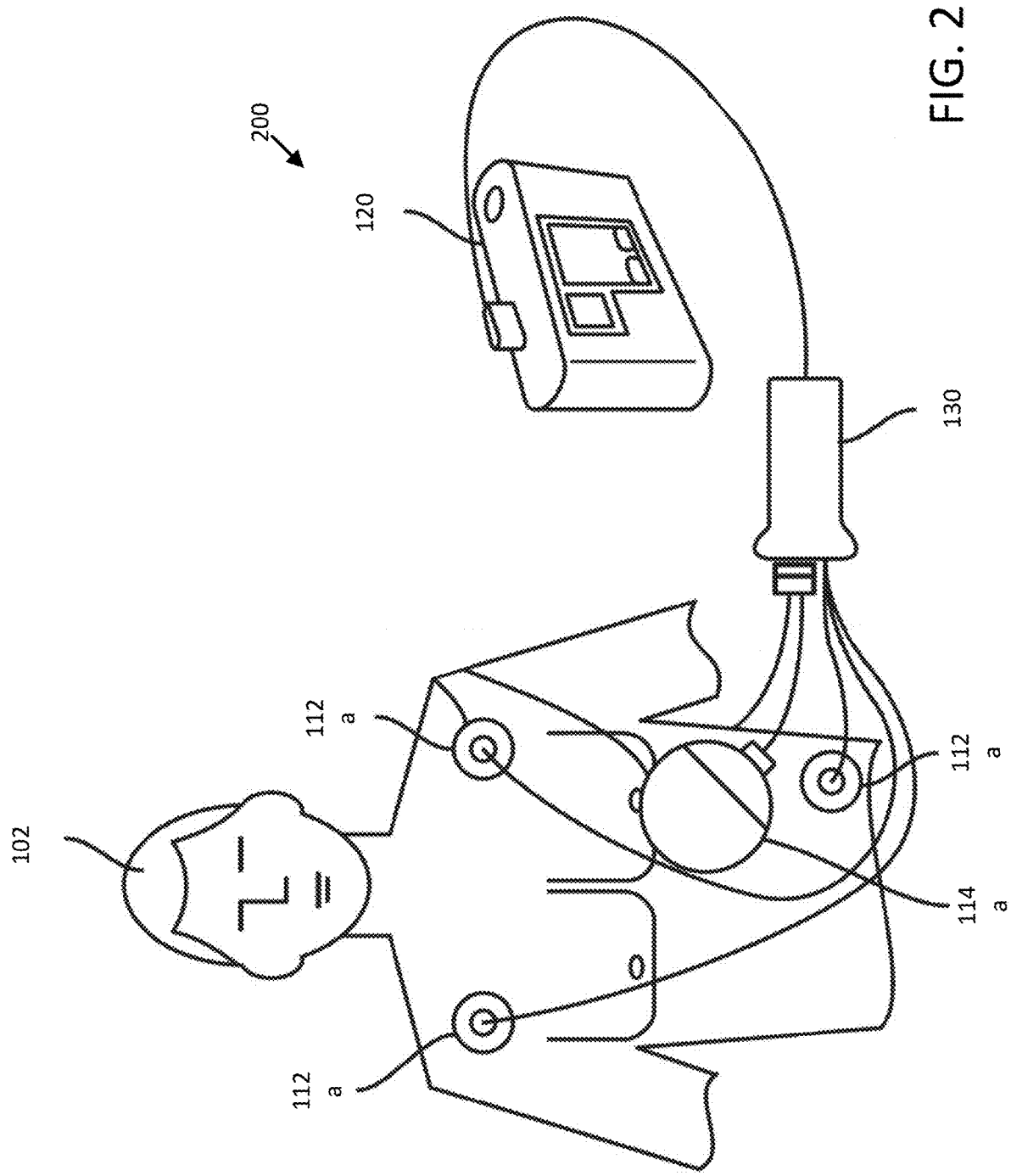
FIG. 2 depicts another wearable, ambulatory, external medical device in accordance with at least one example disclosed herein.

FIG. 2 illustrates an example medical device 200 that is external, ambulatory, and wearable by a patient 102 and configured to monitor the patient for indications of rapid deterioration. For example, the medical device 200 can be a non-invasive medical device configured to be located substantially external to the patient. Such a medical device 200 can be, for example, an ambulatory medical device that is capable of and designed for moving with the patient. For example, the medical device 200 as described herein can be bodily-attached to the patient such as a hospital wearable defibrillator (HWD) available from ZOLL® Medical Corporation. Such HWDs typically are worn nearly continuously or substantially continuously for during a patient's stay in a hospital. During the period of time in which they are worn by the patient, the HWD can be configured to continuously or substantially continuously monitor the vital signs of the patient and, upon determination that treatment is required, can be configured to deliver one or more therapeutic stimulation pulses to the patient. For example, such therapeutic shocks can be pacing, defibrillation, or transcutaneous electrical nerve stimulation (TENS) pulses.

The medical device 200 can include one or more of the following: one or more sensing electrodes 112 (e.g., anterior/posterior ECG electrodes 112a and side/side ECG electrodes), one or more therapy electrodes 114 (e.g. anterior therapy electrode 114a and posterior electrodes), a medical device controller 120 and a connection pod 130. Each of these components are structured and function as do the like number components of the medical device 100.

Figure 3:
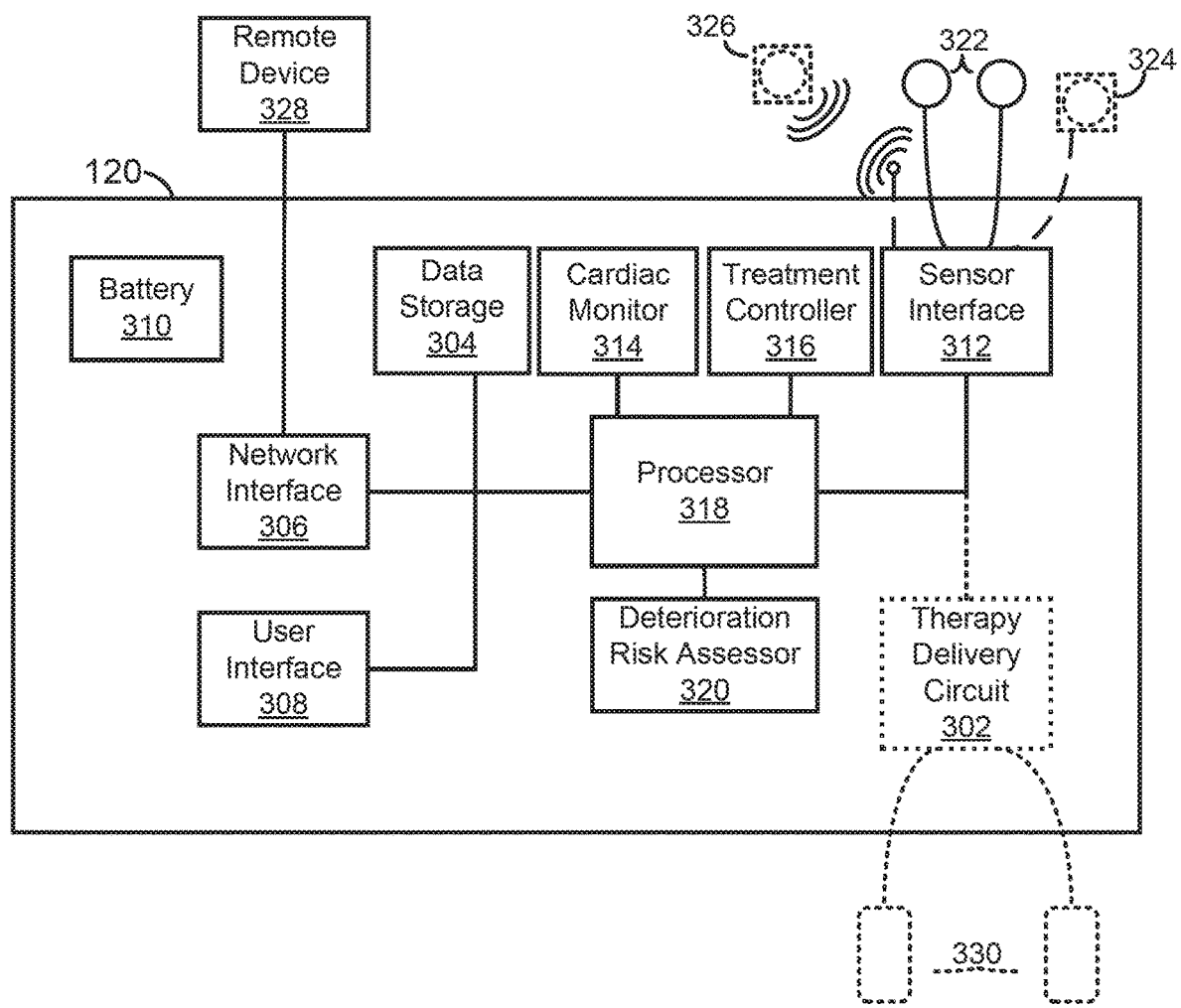
FIG. 3 depicts an arrangement of components of a medical device controller in accordance with at least one example disclosed herein.

FIG. 3 illustrates a sample component-level view of the medical device controller 120. As shown in FIG. 3, the medical device controller 120 can include a therapy delivery circuit 302, a data storage 304, a network interface 306, a user interface 308, at least one battery 310, a sensor interface 312, a cardiac monitor 314, a treatment controller 316, a deterioration risk assessor 320 and least one processor 318. A patient monitoring medical device can include a medical device controller 120 that includes like components as those described above but does not include the therapy delivery circuit 302 (shown in dotted lines).

The therapy delivery circuit 302 can be coupled to one or more therapy electrodes 330 configured to provide therapy to the patient (e.g., similar to therapy electrodes 114a-b as described above in connection with FIG. 1). For example, the therapy delivery circuit 302 can include, or be operably connected to, circuitry components that are configured to generate and provide the therapeutic electrical pulse or shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuit and under control of one or more processors (e.g., processor 318) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). These capacitors can be switched into a series connection during discharge for a defibrillation pulse. For example, four capacitors of approximately 650 uF can be used. The capacitors can have between 350 to 500-volt surge rating and can be charged in approximately 15 to 30 seconds from a battery pack, such as the at least one battery 310.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuit 302 can be configured to perform the switching and pulse delivery operations, e.g., under control of the processor 318. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 304 can include one or more of non-transitory computer readable media, such as flash memory, solid state memory, magnetic memory, optical memory, cache memory, combinations thereof, and others. The data storage 304 can be configured to store executable instructions and data used for operation of the medical device controller 120. In certain implementations, the data storage can include executable instructions that, when executed, are configured to cause the processor 318 to perform one or more functions.

In some examples, the network interface 306 can facilitate the communication of information between the medical device controller 120 and one or more other devices or entities over a communications network. For example, where the medical device controller 120 is included in an ambulatory medical device (such as medical device 100), the network interface 306 can be configured to communicate with a remote computing device such as a remote server or other similar computing device. As shown in FIG. 3, the network interface 306 is configured to communicate with a remote device 328, such as a personal electronic device (via near-field communication) or a cloud server (via Ethernet communication). Example personal electronic devices that may be implemented as the remote device 328 can include hand-held devices, tablets, smartphones, watches, electronic bracelet devices, earpieces, and/or electronic pendants worn about the patient's neck.

In examples, the remote device 328 is implemented as a computer server. In some examples, the network interface 306 can facilitate the communication of information between the medical device controller 120 and the remote device 328 over a communications network. For example, where the medical device controller 120 is included in an ambulatory medical device, the network interface 306 can be configured to communicate with a remote computing device such as a remote computer server or other similar networked computing device. The network interface 306 can include communications circuitry for transmitting data in accordance with a Bluetooth® wireless standard for exchanging such data over short distances to an intermediary device(s), e.g., a base station, a "hotspot" device, a smartphone, tablet, a portable computing device, and/or other devices in proximity of the wearable medical device. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In some examples, the remote device 328 exposes an interface (e.g., an application program interface) to an electronic health records (EHR) system, such as any of the HER systems provided by Epic Systems, AthenaHealth, Allscripts, and Cerner. In these examples, the medical device controller 120 is configured to exchange information regarding a patient's medical history with the remote device 328 via the network interface 306. In these examples, the medical device controller 120 can request a patient's medical history from the remote device 328, receive the patient's medical history from the device 328, and store the patient's medical history in the data storage 304. Subsequently, a clinician can review and/or confirm the patient's medical history prior to its use in additional processing executed by the medical device controller 120.

In certain implementations, the user interface 308 can include one or more physical interface devices such as input devices, output devices, and combination input/output devices and a software stack configured to drive operation of the devices. These user interface elements may render visual, audio, and/or tactile content. Thus, the user interface 308 may receive input or provide output, thereby enabling a user to interact with the medical device controller 120.

In certain implementations, the user interface 308 can include one or more physical interface devices such as input devices, output devices, and combination input/output devices and a software stack configured to drive operation of the devices. These user interface elements may render visual, audio, and/or tactile content, including content relating to location-specific processing. Thus, the user interface 308 may receive input or provide output, thereby enabling a user to interact with the medical device controller 120.

The medical device controller 120 can also include at least one battery 310 configured to provide power to one or more components integrated in the medical device controller 120. The battery 310 can include a rechargeable multi-cell battery pack. In one example implementation, the battery 310 can include three or more 2200 mAh lithium ion cells that provide electrical power to the other device components within the medical device controller 120. For example, the battery 310 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 120.

The sensor interface 312 can be coupled to one or more sensors configured to monitor one or more physiologic parameters of the patient. As shown, the sensors may be coupled to the medical device controller 120 via a wired or wireless connection. The sensors can include one or more electrocardiogram (ECG) electrodes 322 (e.g., similar to sensing electrodes 112 as described above in connection with FIG. 1), cardio-vibrational sensors 324, and tissue fluid monitors 326 (e.g., based on ultra-wide band radiofrequency devices). As such, the sensor interface 312 may include amplifiers and analog to digital converters to condition and digitize signals acquired by the sensors.

The ECG electrodes 322 can monitor a patient's ECG information. For example, the ECG electrodes 322 can be conductive and/or dry electrodes configured to measure changes in a patient's electrophysiology to measure the patient's ECG information. The ECG electrodes 322 can transmit information descriptive of the ECG signals to the sensor interface 312 for subsequent analysis.

The cardio-vibrational sensors 324 can detect a patient's heart sound information. For example, the cardio-vibrational sensors 324 can be configured to detect heart sound values including any one or all of S1, S2, S3, and S4. From these heart sound values, certain cardio-vibrational information may be calculated, including any one or more of electro-mechanical activation time (EMAT), percentage of EMAT (% EMAT), systolic dysfunction index (SDI), and left ventricular systolic time (LVST). The cardio-vibrational sensors 324 can include an acoustic sensor configured to detect sounds from a subject's cardiac system and provide an output signal responsive to the detected cardio-vibrational signals. The cardio-vibrational sensors 324 can also include a multi-channel accelerometer, for example, a three-channel accelerometer configured to sense movement in each of three orthogonal axes such that patient movement/body position can be detected and correlated to detected cardio-vibrational information. The cardio-vibrational sensors 324 can transmit information descriptive of the cardio-vibrational information to the sensor interface 312 for subsequent analysis.

The tissue fluid monitors 326 can use radio frequency (RF) based techniques to assess fluid levels and accumulation in a patient's body tissue. For example, the tissue fluid monitors 326 can be configured to measure fluid content in the lungs, typically for diagnosis and follow-up of pulmonary edema or lung congestion in heart failure patients. The tissue fluid monitors 326 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 326 can transmit information descriptive of the tissue fluid levels to the sensor interface 312 for subsequent analysis.

The sensor interface 312 can be coupled to any one or combination of sensing electrodes/other sensors to receive other patient data indicative of patient parameters. Once data from the sensors has been received by the sensor interface 312, the data can be directed by the processor 318 to an appropriate component within the medical device controller 120. For example, if heart data is acquired by cardio-vibrational sensor 324 and transmitted to the sensor interface 312, the sensor interface 312 can transmit the data to the processor 318 which, in turn, relays the data to the cardiac monitor 314 and/or the treatment controller 316. This data can also be stored on the data storage 304.

In some implementations, the processor 318 includes one or more processors (or one or more processor cores) that each are configured to perform a series of instructions that result in manipulated data and/or control the operation of the other components of the medical device controller 120. In some implementations, when executing a specific process (e.g., patient monitoring, treatment, deterioration risk assessment, etc.), the processor 318 can be configured to make specific logic-based determinations based on input data received, and be further configured to provide one or more outputs that can be used to control or otherwise inform subsequent processing to be carried out by the processor 318 and/or other processors or circuitry with which processor 318 is communicatively coupled. Thus, the processor 318 reacts to specific input stimulus in a specific way and generates a corresponding output based on that input stimulus. In some example cases, the processor 318 can proceed through a sequence of logical transitions in which various internal register states and/or other bit cell states internal or external to the processor 318 may be set to logic high or logic low. As referred to herein, the processor 318 can be configured to execute a function where software is stored in a data store coupled to the processor 318, the software being configured to cause the processor 318 to proceed through a sequence of various logic decisions that result in the function being executed. The various components that are described herein as being executable by the processor 318 can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor. The processor can execute an embedded operating system, and include services provided by the operating system that can be used for file system manipulation, display & audio generation, basic networking, firewalling, data encryption, and communications.

In an implementation, the processor 318 can implement the deterioration risk assessor 320 in the form of a series of instructions that operate on patient physiological data retrieved from the patient and stored in the data storage 304. In some implementations, the deterioration risk assessor 320 may be implemented by a second processor separate from the main processor 318 of the controller 120. The processor 318 can implement the steps shown in FIGS. 5, 6, 8, and 10.

According to some examples illustrated by FIG. 3, the cardiac monitor 314 is configured to initiate and control monitoring of a patient's cardiac function and identification of arrhythmias experienced by the patient. When executing according to this configuration, in some examples, the cardiac monitor 314 detects arrhythmias by scanning ECG data received from the sensor interface 312 for patterns (e.g. heart rates) indicative of arrhythmias. Responsive to identifying a data pattern indicative of an arrhythmia, the cardiac monitor 314 initiates the treatment controller 316.

According to some examples illustrated by FIG. 3, the treatment controller 316 is configured to initiate and control treatment of an arrhythmia identified by the cardiac monitor 314. When executing according to this configuration, in some examples, the treatment controller 316 executes a treatment protocol specific to the particular identified arrhythmia. For instance, the treatment controller 316 may pace a patient experiencing bradycardia or ventricular tachycardia or may defibrillate a patient experiencing atrial or ventricular fibrillation. In some examples, the treatment controller 316 initiates deployment of electrically conductive gel as part of the treatment protocol. Also, in some examples, the treatment controller 316 monitors the reaction of the patient's heart to the treatment protocol and takes further action based on the reaction of the patient's heart. This further action may include altering the treatment protocol and/or escalating notifications to external parties.

A MERT may be implemented within a hospital environment in a variety of ways. For example, a MERT may be implemented to respond to all emergencies occurring within a hospital. In some implementations, the MERT may be employed as a critical care outreach team to respond to emergencies and also follow-up on a patient's post-ICU discharge, or a rapid response team to proactively evaluate high-risk patients. Table 1 shows example compositions of an MERT within a hospital environment. The device and system embodiments described herein may be used by any level of MERT implementation to assist in the execution of their responsibilities.

TABLE 1

| Example MERT team staffing | Example actions and/or MERT responsibilities |
|---|---|
| Critical care nurse, respiratory therapist, and physician (critical care physicians or hospitalists), anesthesiologists, and backup specialists | Respond to all emergencies to perform one or more of: assess the situation, stabilize the patient, assist with communication of physiological status and information with patient, ward staff, and relatives as appropriate, and assist with transfer to a different wing or region of hospital. |
| Critical care physicians and nurses | Respond to emergencies as described above Follow up on patients discharged from ICU Educate staff |
| Physicians (critical care physicians or hospitalists), nurses, and/or other specialists | Respond to emergencies as described above Follow up on patients discharged from ICU Proactively evaluate high-risk ward patients, and educate andact as liaison to ward staff |

Example criteria for involving a MERT may be predetermined and configured in advance. In some examples, the criteria may be determined on a patient-by-patient basis. For example, such criteria may be set during admission to the hospital. Each hospital organization may determine criteria to be used to escalate a call to a MERT and educate the staff accordingly. Example criteria may include the following:

Acute change in heart rate 130 bpm
Acute change in systolic blood pressure, 28 per min
Acute change in saturation, <90% despite $O_2$
Acute change in conscious state and/or neurological state
Acute change in urinary output to <50 ml in 4 hours According to some examples illustrated by FIG. 3, the deterioration risk assessor 320 (e.g., as implemented by processor 318 or a stand-alone processor separate from processor 318) is configured to collect and monitor patient parameters, to generate a risk estimate of patient deterioration, and to take further action where warranted by the risk estimate. When executing according to this configuration in some examples, the deterioration risk assessor 320 executes a deterioration risk assessment process. The specific actions executed as part of the deterioration risk assessment process vary between examples, some of which are described further below with reference to FIGS. 5, 6, 8, and 10-12. In some examples, the deterioration risk assessment process is a part of an overall patient monitoring and treatment process executed by the medical device, such as the monitoring and treatment process described further below with reference to FIG. 9.

In some examples, the deterioration risk assessor 320 is configured to interoperate with other components of the medical device controller 120 to implement particular features. For instance, in at least one example, the deterioration risk assessor 320 is configured to source patient parameters from the sensor interface 312, the user interface 308, the network interface 306, and/or the data storage 304. In this example, the deterioration risk assessor 320 is configured to interoperate with the sensor interface 312 to receive sensor data descriptive of patient parameters. This sensor data may be generated, by one or more processors, from physiologic signals acquired from the patient. In this situation, the deterioration risk assessor 320 generates the patient parameters from the sensor data. In some examples, the deterioration risk assessor 320 is configured to interoperate with the user interface 308 to receive patient parameters collected and entered by a user (e.g., the patient 102 or a caregiver). In these examples, the deterioration risk assessor 320 is configured to display, via the user interface 308, prompts for the patient parameters to the user. In some examples, the deterioration risk assessor 320 is configured to receive patient parameters from another device via the network interface 306. For instance, in at least one example, the deterioration risk assessor 320 is configured to receive patient parameters via a near field communication connection with another device. Devices from which the deterioration risk assessor 320 may receive patient parameters include electronic medical records systems, other medical devices, personal electronics, remotely located cloud servers, and the like. In some examples, the deterioration risk assessor 320 may store patient parameters received via these various sources in the data storage 304 for subsequent retrieval and processing. For example, patient parameters can include vital signs data such as temperature, pulse, respiratory rate, and blood pressure. The patient parameters can include ECG metrics, such as PR interval (PR), P-wave duration, QRS duration, RR interval (RR), QT interval (QT), T-wave complexity (T Complex), ST segment levels for different leads, such as leads I, II, V (ST I, ST II, ST V), and a plurality of different heart rate variability (HRV) parameters. The patient parameters can include cardio-vibrational parameters such as cardio-vibrational S1, S2, S3, and S4 intensities, EMAT, % EMAT, LUST, % LVST, and the like. The parameters can include pulmonary-vibrational parameters such as vibrations of the patient's lungs and chest.

In some examples, the deterioration risk assessor 320 is configured to periodically interoperate with the user interface 308 to execute a neurologic examination or assessment of the patient. This neurologic examination may generate a patient parameter that indicates whether the patient is alert, not alert but reacting to voice, not alert and not reacting to voice but reacting to pain, or none of the above/unresponsive. For instance, this patient neurological parameter may be a score on the Glascow Coma scale parameter.

The content of the neurologic examination may vary between examples and may include prompts, survey questions, and/or games. For instance, in some examples, the deterioration risk assessor 320 is configured conduct the neurologic examination by prompting the patient via, for example, a vibration or audio signal to respond by pressing a physical or soft button that is a part of the user interface 308. When executing according to this configuration, where the deterioration risk assessor 320 detects a patient response via actuation of the button within a target time frame (e.g., 0-1 second, 0-2 seconds, or 0-3 seconds), the deterioration risk assessor 320 generates a patient parameter that indicates that patient is alert and fully responsive. For example, the patient parameter may include a score of 16 on the Glascow Coma Scale (GCS). A GCS score of 16 indicates no brain injury. In contrast, where the deterioration risk assessor 320 fails to detect a patient response within the target time frame, the deterioration risk assessor 320 escalates the prompt by, for example, issuing a human language audio prompt, such as "Are you awake?" or "Are you ok?". Where the deterioration risk assessor 320 detects a patient response (e.g., by detecting physical movement or a verbal response via cardiography sensors and/or accelerometers within the user interface 308) within a target time frame (e.g., 0-6 seconds), the deterioration risk assessor 320 generates a patient parameter that indicates that patient is semi-responsive. For example, the patient parameter may include a GCS score of 13-15 (indicating mild brain injury) where the patient response is received before a first target time frame (e.g., 0-1 second, 0-2 seconds, or 0-3 seconds) or a GGS score of 9-12 (indicating moderate brain injury) where the patient is received before a second target time frame (e.g., 1-6 seconds, 2-6 seconds, or 3-6 seconds). In contrast, where the deterioration risk assessor 320 fails to detect a patient response within the target time frame, the deterioration risk assessor 320 escalates the prompt by, for example, providing noxious stimulation to the patient in the form of a low-level shock delivered to the patient via the therapy delivery circuit 302. Where the deterioration risk assessor 320 detects a patient response (e.g., by detecting physical movement or a verbal response via cardiography sensors and/or accelerometers within the user interface 308) within a target time frame (e.g., 0-1 second, 0-2 seconds, or 0-3 seconds), the deterioration risk assessor 320 generates a patient parameter that indicates that patient is nominally responsive. For example, the patient parameter may include a GCS score of less than 8 (indicating severe brain injury). In contrast, where the deterioration risk assessor 320 fails to detect a patient response within the target time frame, the deterioration risk assessor 320 generates a patient parameter that indicates that patient is non-responsive. For example, the patient parameter may include a GCS score of 1.

In some examples, the deterioration risk assessor 320 is configured conduct the neurologic examination to assess various types of patient memory. For instance, in some examples, the deterioration risk assessor 320 is configured to assess immediate memory of the patient by displaying (e.g., via a screen that is a part of the user interface 308) a first set of words having a predefined, configurable cardinality (e.g., 3) to the patient. This first set of words may include, for example, "apple," "car," and "tree." In these examples, the deterioration risk assessor 320 is configured to wait a predefined, configurable time period (e.g., 5 minutes) before prompting the patient to identify the words in the first set from a second set of words having a cardinality (e.g., 6) greater than the first set.

In some examples, the deterioration risk assessor 320 is configured conduct the neurologic examination to assess response time (combination of motor and neurologic function). For instance, in some examples, the deterioration risk assessor 320 is configured to prompt the patient to press a button that is a part of the user interface 308 when a circle appears on a screen that is also part of the user interface 308. In these examples, the deterioration risk assessor 320 is configured record the amount of time between display of the circle and actuation of the button and to generate a patient parameter that indicates the amount of time. In some examples, the deterioration risk assessor 320 is configured to store patient parameters generated by neurologic examination along with other patient parameters in the data storage 304 for subsequent processing.

With respect to patient pallor parameters, a clinician such as nurse or other caregiver can provide input via the user interface 308 indicating their assessment of the patient's pallor. For example, the clinician may assess the patient's pallor based on the patient's appearance. For example, appearance of skin cyanosis, e.g., a blue or purplish discoloration of the patient's skin or mucous membranes due to tissues near the skin having low oxygen saturation. In implementations, the patient's appearance can be graded, for example, using a numerical scale. For example, a pallor parameter scale may range from zero (0) to five (5). As an illustration, a pallor parameter value of zero (0) may indicate that the patient's skin does not exhibit any signs of abnormal discoloration or change. A pallor parameter of one (1) may indicate apparent mild pallor, three (3) may indicate apparent moderate pallor, and five (5) may indicate apparent severe pallor. For example, visible bluish or purplish coloration of the fingers or other limbs may be graded as a four (4) or a five (5).

As stated above, in some examples, the deterioration risk assessor 320 is configured to take further action where warranted by a risk estimate of patient deterioration. This further action may include notifying a caregiver or the patient of the risk estimate, prompting the caregiver or the patient for information, and/or adjusting the frequency with which the deterioration risk assessor 320 updates risk estimates. The criterion or criteria used by the deterioration risk assessor 320 to determine whether further action is warranted varies between examples. For instance, in some examples, the deterioration risk assessor is configured to determine that further action is warranted by comparing a risk estimate or a series of risk estimates to benchmark criteria established at the time of patient admission (or a subsequent re-assessment of the patient). For instance, in some examples, the deterioration risk assessor 320 is configured to determine that further action is warranted where a risk estimate transgresses a configurable, predefined threshold value. Alternatively or additionally, in some examples, the deterioration risk assessor 320 is configured to determine that further action is warranted where a series of risk estimates is trending downward with a slope that transgresses a configurable, predefined threshold value. Either of these transgressions could indicate, for example, a lack of patient responsiveness to pain or a progressively worsening patient memory. In some examples, the deterioration risk assessor 320 is configured to adjust the criteria to increase the likelihood of taking further action where, for example, caregiver visits to the patient are less likely (e.g., during night hours). In these examples, the deterioration risk assessor 320 is configured to determine whether the current time falls within a time period associated with a reduced frequency of caregiver visits to the patient. If so, the deterioration risk assessor 320 adjusts the criteria appropriately (e.g., decreases the risk estimate of patient deterioration score required to initiate further action). Additional examples of criteria used to determine whether additional action is warranted are described further below.

In some examples, the deterioration risk assessor 320 is configured to interoperate with the user interface 308 and the data storage 304 to implement elements that allow a user (e.g., the patient, a caregiver, etc.) to adjust a schedule stored in the data storage 304 according to which the deterioration risk assessor 320 executes is various monitoring and assessment processes. For instance, in some examples, the patient may adjust a frequency with which the monitoring and assessment processes are executed before sleeping, or a caregiver may adjust this frequency based on a recent patient assessment. In some examples, the deterioration risk assessor 320 is configured to determine a default frequency that is dependent upon an assessment of the patient by the caregiver. For example, if the clinician enters, (e.g., during a neurologic assessment) neurologic parameters such as level of consciousness, pupillary reactions, Glasgow Coma Scale values, etc. and those values indicated a lower level of consciousness, the device might be configured to test more frequently to ensure that there wasn't further negative progression. Likewise, if the clinician enters values for pallor parameters and those values indicated moderate to severe pallor (and, optionally, other abnormal parameters) the device might be configured to test more frequently. In some examples, the deterioration risk assessor 320 is configured to adjust the frequency of monitoring and assessment processes where, for example, caregiver visits to the patient are less likely (e.g., during night hours). In these examples, the deterioration risk assessor 320 is configured to determine whether the current time falls within a time period associated with a reduced frequency of caregiver visits to the patient. If so, the deterioration risk assessor 320 adjusts the criteria appropriately (e.g., decreases a span of time between re-executions/iteration of the monitoring and assessment processes).

The cardiac monitor 314, the treatment controller 316, and the deterioration risk assessor 320 can be implemented using hardware or a combination of hardware and software. For instance, in some examples, the cardiac monitor 314, the treatment controller 316, and/or the deterioration risk assessor 320 are implemented as software components that are stored within the data storage 304 and executed by the processor 318. In these examples, the instructions included in the cardiac monitor 314, the treatment controller 316, and/or the deterioration risk assessor 320 can cause the processor 318 to monitor for, detect, and treat arrhythmias, as well as detect and/or predict deterioration of a patient's clinical condition. In other examples, the cardiac monitor 314, the treatment controller 316, and/or the deterioration risk assessor 320 are application-specific integrated circuits (ASICs) that are coupled to the processor 318 and configured to monitor for, detect, and treat arrhythmias as well as detect and/or predict deterioration of a patient's clinical condition. In at least one example, the deterioration risk assessor 320 (and/or its components as described further below) is implemented as a cloud service (e.g., a Web Service) that securely receives patient parameters and responds with a risk estimate of patient deterioration. Thus, examples of the cardiac monitor 314, the treatment controller 316, and the deterioration risk assessor 320 are not limited to a particular hardware or software implementation.

While examples illustrated in FIG. 3 include the deterioration risk assessor 320 as a component of the medical device controller 120, the examples disclosed herein are not limited to this architecture. For instance, in some examples directed to distributed architectures, the deterioration risk assessor 320, or portions thereof (e.g., the various risk assessment engines described below) reside on the remote device 328. In these examples, signals and/or data descriptive of patient parameters (e.g., continuously monitored patient parameters) are transmitted to the remote device 328 where these signals and/or data are processed by the deterioration risk assessor 320.

Figure 4:
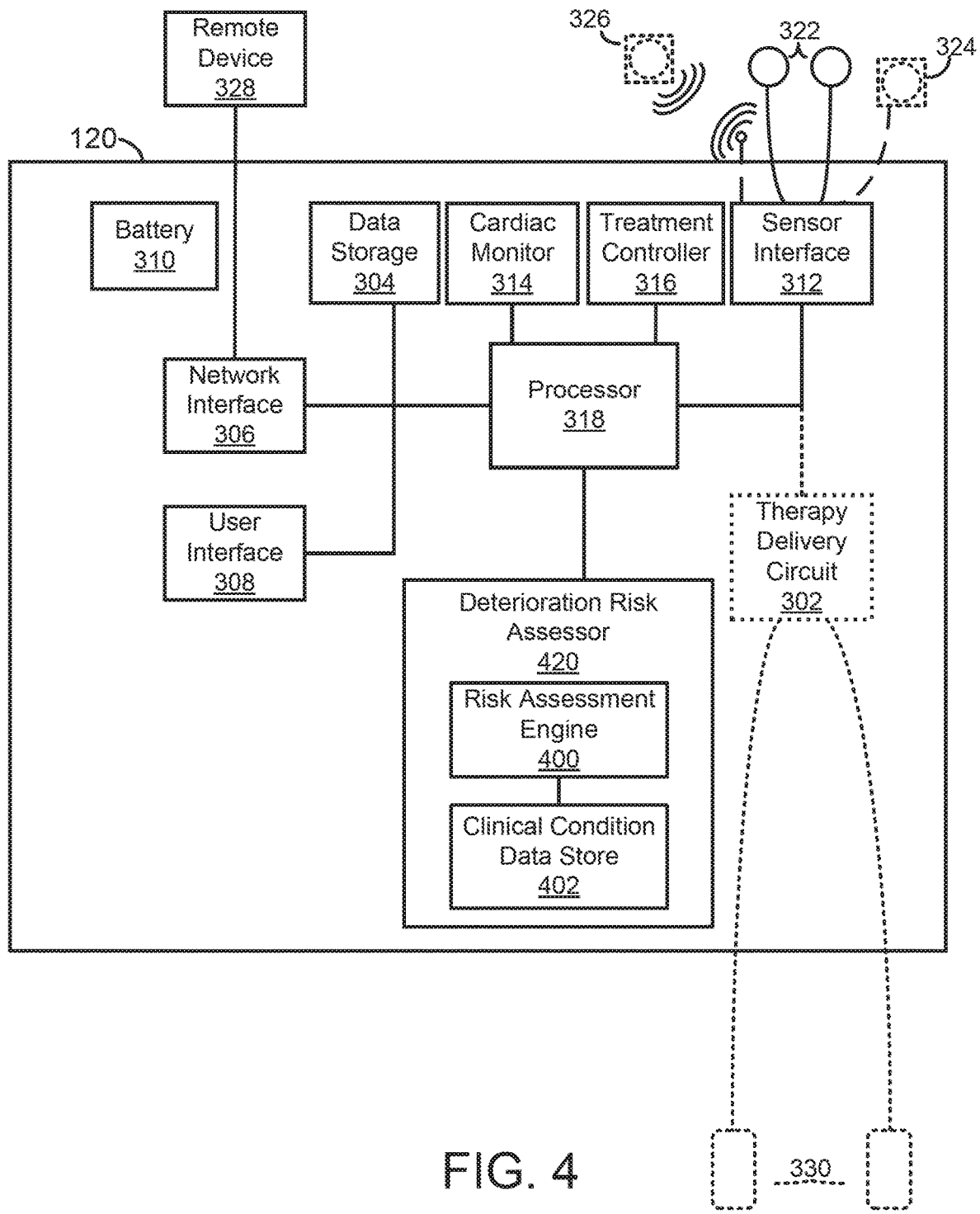
FIG. 4 depicts a first example of a deterioration risk assessor within the context of the medical device controller illustrated in FIG. 3 in accordance with at least one example disclosed herein.

Some example medical devices disclosed herein include a deterioration risk assessor that incorporates and further refines the deterioration risk assessor 320. In these examples, the deterioration risk assessor 320 is further configured to execute deterioration risk assessment processes tailored to a clinical condition presented by a patient, a presentable clinical condition of the patient (e.g., the patient 102, FIGS. 1-2). Initially, data identifying a plurality of presentable clinical conditions, a plurality of risk assessment processes associated with the plurality of presentable clinical conditions, and a corresponding plurality of clinical criteria associated with the plurality of risk assessment processes are stored in a memory of the device, e.g., data storage 304 of FIG. 3. When executing according to this configuration, the deterioration risk assessor 320 generates a risk estimate of patient deterioration via execution of these deterioration risk assessment processes. In some examples, the deterioration risk assessor 320 is also further configured to compare the risk estimate to one or more clinical criterion associated with the clinical condition to determine whether further action is warranted. This further action may include notifying a user (e.g., a caregiver and/or the patient) of the risk estimate and/or prompting the patient to respond, for example via a neurologic test. FIG. 4 illustrates an example medical device controller (e.g., the medical device controller 120) that includes a deterioration risk assessor 420 configured in accord with these examples. As shown, the deterioration risk assessor 420 includes a risk assessment engine 400 and a clinical condition data store 402. For example, clinical condition data store 402 can be implemented within the data storage 304 of the device or be implemented as a separate physical memory device. For example, the clinical condition data store 402 may be implemented as a removable or unremovable memory device such as a solid-state memory, flash memory, a secure digital non-volatile memory card, magnetic memory, optical memory, cache memory, or combinations thereof.

In some examples, the deterioration risk assessor 420 illustrated in FIG. 4 is configured to identify a presentable clinical condition of the patient prior to executing the deterioration risk assessment process. To identify the presentable clinical condition of the patient in some examples, the deterioration risk assessor 420 is configured to retrieve (e.g., from the data store 304 or elsewhere) an identifier of the clinical condition of the patient based on an initial assessment of the patient at admission to the hospital. In these examples, the deterioration risk assessor 420 is also configured to generate (e.g., calculate and/or predict, as will be described further below with reference to FIGS. 5 and 6) patient parameters other than the identifier. In some examples, the deterioration risk assessor 420 is configured to provide the patient parameters, including the identifier, to the risk assessment engine 400. The risk assessment engine 400 is configured to determine a risk estimate of patient deterioration based on the patient parameters as described further below with reference to FIG. 6. Further, in these examples, the deterioration risk assessor 420 is configured to receive, from the risk assessment engine 400, the risk estimate of patient deterioration.

In some examples, the deterioration risk assessor 420 is configured to determine whether the risk estimate of patient deterioration received from the risk assessment engine 400 falls outside one or more clinical criterion associated with the clinical condition of the patient. For instance, in some examples, the deterioration risk assessor 420 is configured to access a cross-reference data structure (e.g., a look-up table, array, or a similar data structure) stored in the clinical condition data store 402 that includes associations between a presentable clinical condition, a deterioration risk assessment process, and the one or more clinical criterion. These one or more clinical criterion may include ranges, threshold values, and/or a plurality of discrete elements. In some examples, the deterioration risk assessor 420 is configured to identify the one or more clinical criterion via the cross-reference and to compare the one or more clinical criterion to the risk estimate of patient deterioration received from the risk assessment engine 400. Where this comparison indicates that the risk estimate of patient deterioration falls outside the one or more clinical criterion, the deterioration risk assessor 420 is configured to take additional action (e.g., notify the patient or a caregiver of the risk).

In some examples, to execute a deterioration risk assessment process specific to a clinical condition, the deterioration risk assessor 420 is configured to initiate the risk assessment engine 400 and provide the risk assessment engine 400 with patient parameters. In these examples, the risk assessment engine 400 is configured to receive the patient parameters from the deterioration risk assessor 420 and/or the clinical data store 402 and to retrieve, from the clinical condition data store 402, an argument set of patient parameters, weights, and scoring criteria associated with the identified clinical condition. For instance, in some examples, the risk assessment engine 400 is configured to access a cross-reference data structure stored in the clinical condition data store 402. This cross-reference data structure includes associations between a presentable clinical condition and an argument set. In these examples, the risk assessment engine 400 is configured to identify an argument set associated with the clinical condition and to process the argument set to tailor a deterioration risk assessment process to the clinical condition identified in the patient parameters.

Tables 2-5 illustrate arguments sets that are associated with various clinical conditions that may be stored within the clinical condition data store 402. As shown in Tables 2-5, the argument sets specify that a common set of patient parameters to be monitored. This common set of patient parameters includes heart rate, heart rate variability, ectopic activation or contractions (e.g., premature ventricular complexes), respiration rate, SpO2, blood pressure, neurological state, SMO2, and cerebral oxygenation parameters. As further shown in Tables 2-5, each patient parameter is associated with a weight and a scoring scale. The scoring scale maps particular values of each parameter to a score between 0 and 5. The scoring scales may be based on population benchmark values or baseline values specific to the patient that are established during the initial fitting of the medical device. The weight specifies an importance of each patient parameter to an overall score and is used by the deterioration risk assessor 320 to weight the score of each parameter value. As shown, Table 2 illustrates an argument set associated with a heart failure clinical condition. Table 3 illustrates an argument set associated with a post-syncope clinical condition. Table 4 illustrates an argument set associated with a post-myocardial infarction (MI) clinical condition. Table 5 illustrates an argument set associated with a breathing disorders clinical condition.

TABLE 2

Heart Failure Argument Set

| Parameter | Weight | 5 | 4 | 3 | 2 | 1 | 0 | 1 | 2 | 3 | 4 | 5 |
|---|---|---|---|---|---|---|---|---|---|---|---|---|
| Heart Rate (beats per minute) | 1.0 | <40 | 40-50 | 50-55 | 55-60 | 60-70 | 70-80 | 80-90 | 90-100 | 100-120 | 120-140 | >140 |
| Heart Rate Variability (deviation from baseline) | 1.0 | >40% | | 10%-20% | | | <10% | | | 10%-20% | | >40% |
| Ectopic Contractions (deviation from baseline) | 1.0 | >40% | | 10%-20% | | | <10% | | | 10%-20% | | >40% |
| Respiration (breaths per minute) | 0.5 | <5 BPM | | 5-6 | | 6-8 | 9-14 | 14-20 | | 20-25 | 25-29 | >29 |
| SpO2 (oxygenation) | 0.5 | 85% | | 85%-90% | | | 95%-100% | | | | | |
| Blood pressure (systolic/diastolic) | 0.25 | 70-80/ 50-60 | 80-90/ 60-70 | 100-120/ 70-80 | | | 120/80 | | | 150-180/ 95-100 | 180-200/ 100-120 | >200/>120 |
| Neurological State (Glasgow Coma score) | 0.25 | <8 | | 8-12 | | | 12-15 | | | | | |
| Electromechanical parameters (deviation from baseline) | 0.5 | >40% | | 10%-20% | | | <10% | | | 10%-20% | | >40% |
| SMO2 (deviation from baseline) | 0.5 | >40% | | 10%-20% | | | <10% | | | 10%-20% | | >40% |
| Cerebral oxygenation (deviation from baseline) | 0.5 | >40% | | 10%-20% | | | <10% | | | 10%-20% | | >40% |

TABLE 3

Post-Syncope Argument Set

| Parameter | Weight | 5 | 4 | 3 | 2 | 1 | 0 | 1 | 2 | 3 | 4 | 5 |
|---|---|---|---|---|---|---|---|---|---|---|---|---|
| Heart Rate (beats per minute) | 1.0 | <40 | 40-50 | 50-55 | 55-60 | 60-70 | 70-80 | 80-90 | 90-100 | 100-120 | 120-140 | >140 |
| Heart Rate Variability (deviation from baseline) | 1.0 | >40% | | 10%-20% | | | <10% | | | 10%-20% | | >40% |
| Ectopic Contractions (deviation from baseline) | 1.0 | >40% | | 10%-20% | | | <10% | | | 10%-20% | | >40% |
| Respiration (breaths per minute) | 1.0 | <5 BPM | | 5-6 | | 6-8 | 9-14 | 14-20 | | 20-25 | 25-29 | >29 |
| SpO2 (oxygenation) | 1.0 | 85% | | 85%-90% | | | 95%-100% | | | | | |
| Blood pressure (systolic/diastolic) | 1.0 | 70-80/ 50-60 | 80-90/ 60-70 | 100-120/ 70-80 | | | 120/80 | | | 150-180/ 95-100 | 180-200/ 100-120 | >200/>120 |
| Neurological State (Glasgow Coma score) | 1.0 | <8 | | 8-12 | | | 12-15 | | | | | |
| Electromechanical parameters (deviation from baseline) | 1.0 | >40% | | 10%-20% | | | <10% | | | 10%-20% | | >40% |
| SMO2 (deviation from baseline) | 1.0 | >40% | | 10%-20% | | | <10% | | | 10%-20% | | >40% |
| Cerebral oxygenation (deviation from baseline) | 1.0 | >40% | | 10%-20% | | | <10% | | | 10%-20% | | >40% |

TABLE 4

Post-MI Argument Set

| Parameter | Weight | 5 | 4 | 3 | 2 | 1 | 0 | 1 | 2 | 3 | 4 | 5 |
|---|---|---|---|---|---|---|---|---|---|---|---|---|
| Heart Rate (beats per minute) | 1.0 | <40 | 40-50 | 50-55 | 55-60 | 60-70 | 70-80 | 80-90 | 90-100 | 100-120 | 120-140 | >140 |
| Heart Rate Variability (deviation from baseline) | 1.0 | >40% | | 10%-20% | | | <10% | | | 10%-20% | | >40% |
| Ectopic Contractions (deviation from baseline) | 1.0 | >40% | | 10%-20% | | | <10% | | | 10%-20% | | >40% |
| Respiration (breaths per minute) | 0.5 | <5 BPM | | 5-6 | | 6-8 | 9-14 | 14-20 | | 20-25 | 25-29 | >29 |
| SpO2 (oxygenation) | 1.0 | 85% | | 85%-90% | | | 95%-100% | | | | | |
| Blood pressure (systolic/diastolic) | 1.0 | 70-80/ 50-60 | 80-90/ 60-70 | 100-120/ 70-80 | | | 120/80 | | | 150-180/ 95-100 | 180-200/ 100-120 | >200/>120 |

TABLE 4-continued

Post-MI Argument Set

| Parameter | Weight | 5 | 4 | 3 | 2 | 1 | 0 | 1 | 2 | 3 | 4 | 5 |
|---|---|---|---|---|---|---|---|---|---|---|---|---|
| Neurological State (Glascow Coma score) | 0.8 | <8 | | 8-12 | | | 12-15 | | | | | |
| Electromechanical parameters (deviation from baseline) | 1.0 | >40% | | 10%-20% | | | <10% | | | 10%-20% | | >40% |
| SMO2 (deviation from baseline) | 0.5 | >40% | | 10%-20% | | | <10% | | | 10%-20% | | >40% |
| Cerebral oxygenation (deviation from baseline) | 0.5 | >40% | | 10%-20% | | | <10% | | | 10%-20% | | >40% |

TABLE 5

Breathing Disorders Argument Set

| Parameter | Weight | 5 | 4 | 3 | 2 | 1 | 0 | 1 | 2 | 3 | 4 | 5 |
|---|---|---|---|---|---|---|---|---|---|---|---|---|
| Heart Rate (beats per minute) | 0.5 | <40 | 40-50 | 50-55 | 55-60 | 60-70 | 70-80 | 80-90 | 90-100 | 100-120 | 120-140 | >140 |
| Heart Rate Variability (deviation from baseline) | 0.5 | >40% | | 10%-20% | | | <10% | | | 10%-20% | | >40% |
| Ectopic Contractions (deviation from baseline) | 0.5 | >40% | | 10%-20% | | | <10% | | | 10%-20% | | >40% |
| Respiration (breaths per minute) | 1.0 | <5 BPM | | 5-6 | | 6-8 | 9-14 | 14-20 | | 20-25 | 25-29 | >29 |
| SpO2 (oxygenation) | 1.0 | 85% | | 85%-90% | | | 95%-100% | | | | | |
| Blood pressure (systolic/diastolic) | 0.8 | 70-80/ 50-60 | 80-90/ 60-70 | 100-120/ 70-80 | | | 120/80 | | | 150-180/ 95-100 | 180-200/ 100-120 | >200/>120 |
| Neurological State (Glascow Coma score) | 0.25 | <8 | | 8-12 | | | 12-15 | | | | | |
| Electromechanical parameters (deviation from baseline) | 0.5 | >40% | | 10%-20% | | | <10% | | | 10%-20% | | >40% |
| SMO2 (deviation from baseline) | 1.0 | >40% | | 10%-20% | | | <10% | | | 10%-20% | | >40% |
| Cerebral oxygenation | 1.0 | >40% | | 10%-20% | | | <10% | | | 10%-20% | | >40% |

In one example illustrated by Table 2, the heart rate patient parameter has a weight of 1. Also, in this example, the risk assessment engine 400 is configured (via the argument set) to map a heart rate value of less than 40 beats per minute to a score of 5. In this example, the risk assessment engine 400 is also configured to map a heart rate value between 40 and 50 beats per minute to a score of 4. In this example, the risk assessment engine 400 is also configured to map a heart rate value between 50 and 55 beats per minute to a score of 3. In this example, the risk assessment engine 400 is also configured to map a heart rate value between 55 and 60 beats per minute to a score of 2. In this example, the risk assessment engine 400 is also configured to map a heart rate value between 60 and 70 beats per minute to a score of 1. In this example, the risk assessment engine 400 is also configured to map a heart rate value between 70 and 80 beats per minute to a score of 0. In this example, the risk assessment engine 400 is also configured to map a heart rate value between 80 and 90 beats per minute to a score of 1. In this example, the risk assessment engine 400 is also configured to map a heart rate value between 90 and 100 beats per minute to a score of 2. In this example, the risk assessment engine 400 is also configured to map a heart rate value between 100 and 120 beats per minute to a score of 3. In this example, the risk assessment engine 400 is also configured to map a heart rate value between 120 and 140 beats per minute to a score of 4. In this example, the risk assessment engine 400 is also configured to map a heart rate value greater than 140 beats per minute to a score of 5.

While Tables 2-5 illustrate particular clinical conditions, parameter values, weights, and scoring scales, the examples disclosed herein are not limited to these particularities. For instance, in some examples, one or more of the argument sets includes patient parameters different from the patient parameters of other argument sets. In addition, some examples include argument sets associated with clinical conditions other than those specified in Tables 2-5. Moreover, some examples use different weight mechanisms, such as individual and non-uniform scoring scales per parameter. Other variations will be apparent to one of ordinary skill in view of the teachings of this specification.

In some examples, after identifying the argument set associated with the clinical condition of the patient, the risk assessment engine 400 is configured to execute the remainder of the deterioration risk assessment process using the argument set. In some examples, in executing the deterioration risk assessment process, the risk assessment engine iterates through each patient parameter specified in the argument set, determines a score (e.g., 0-5) and a weight for the patient parameter, multiplies the score by the weight to generate a weighted score, and adds the weighted score to previously calculated weighted scores of other parameters to generate a total weighted score.

In some examples, the risk assessment engine 400 is configurable (e.g., via configuration information stored in the data storage 304) to operate in either a predictive total mode or a non-predictive total mode. When operating in the predictive total mode, the risk assessment engine 400 generates a risk estimate of patient deterioration by predicting a future value of the total weighted score based on previously calculated weighted total scores (e.g., via extrapolation, regression, time series methods, etc.). When operating in a non-predictive total mode, the risk assessment engine 400 generates a risk estimate of patient deterioration by simply returning the currently calculated total weighted score. The non-predictive total mode may be particularly useful where the patient parameter values used to determine a score for the patient parameters are predictions rather than actual observations.

Figure 5:
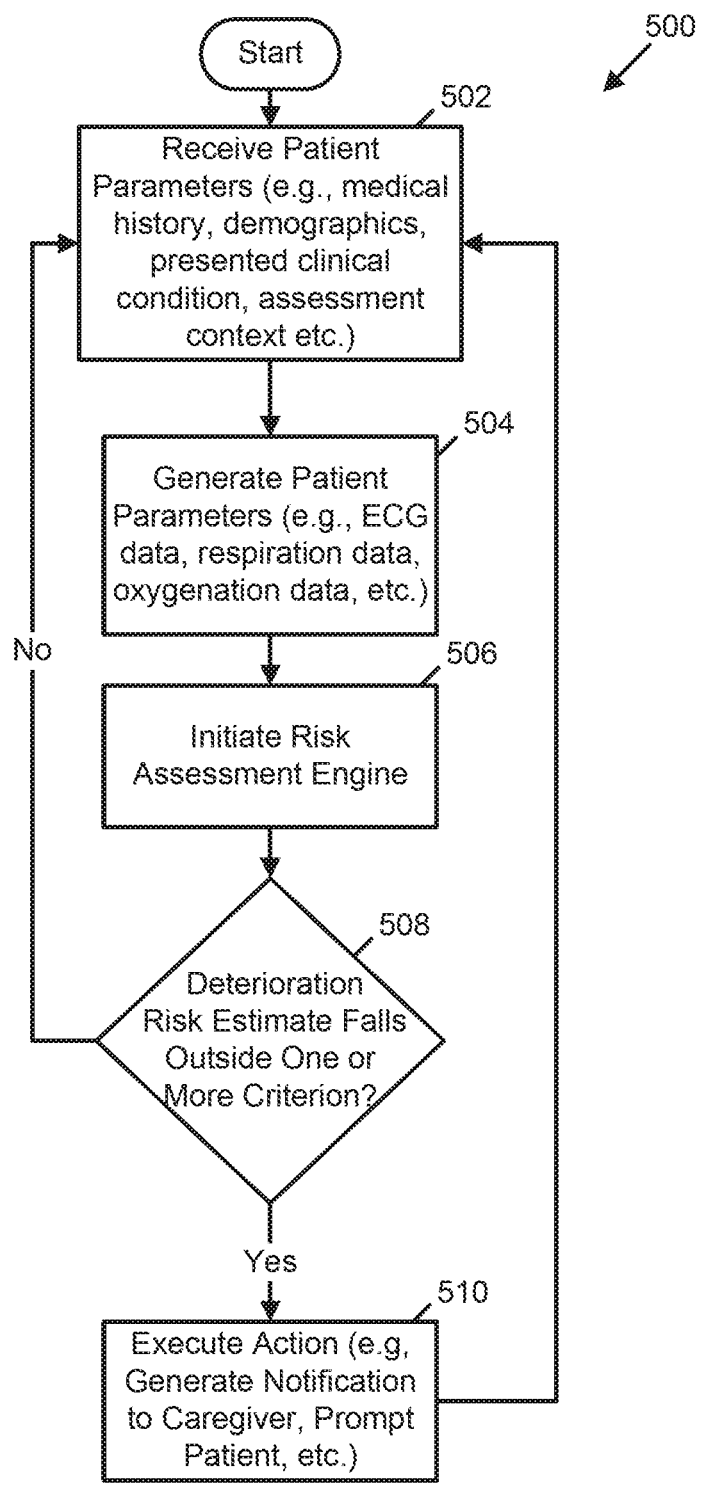
FIG. 5 depicts a monitoring and treatment process executed by a medical device in accordance with at least one example disclosed herein.

FIG. 5 illustrates a monitoring and treatment process 500 that medical devices including the deterioration risk assessor 420, the risk assessment engine 400, and the clinical condition data store 402 are configured to execute, in some examples. As shown, the monitoring and treatment process 500 starts in act 502 with a deterioration risk assessor (e.g., the deterioration risk assessor 420) receiving patient parameters. Within the act 502, the deterioration risk assessor receives patient parameters from, for example, a user interface (e.g., the user interface 308), although any of the sources described above may provide the patient parameters to the deterioration risk assessor in the act 502. The patient parameters received in the act 502 may include any of the irregularly monitored parameters and the periodically monitored parameters described above, although the continuously monitored parameters may be received in the act 502 in some examples. For instance, the deterioration risk assessor may prompt a caregiver for the patient's medical history, demographic information, and the patient assessment context (at admission, during transfers, etc.). In some examples of the act 502 directed to distributed architectures, the patient parameters are received by a user interface provided by the remote device 328 and stored in a memory local to the remote device 328. In some examples, the deterioration risk assessor further stores received patient parameters in a clinical condition data store (e.g., the clinical data store 402).

In act 504, the deterioration risk assessor generates patient parameters from data (e.g., sensor data) descriptive of the patient parameters. Within the act 504, the deterioration risk assessor receives patient parameters from, for example, a sensor interface (e.g., the sensor interface 312), although any of the sources described above may provide the patient parameters to the deterioration risk assessor in the act 504. The patient parameters received in the act 504 may include any of the continuously monitored parameters described above, although the irregularly monitored parameters and the periodically monitored parameters may be received in the act 504 in some examples. In some examples, the acts 502 and 504 are combined during an initial patient assessment or a subsequent patient assessment in which all of the patient parameters described in the acts 502 and 504 are received and/or generated. In some examples, the deterioration risk assessor further stores generated patient parameters in the clinical data store.

Further, in some examples of the act 504, in generating the patient parameters, the deterioration risk assessor executes a prediction process that generates predicted values for the patient parameters that are based on the observations reported in the sensor data and observations reported in previously received sensor data. The prediction process executed by the deterioration risk assessor may vary between examples. For instance, in some examples, the prediction process is a simple extrapolation or linear regression process designed to identify an overall time trend latent within the sensor data. In some examples, more sophisticated time series analysis of the past and current sensor data may be employed within the prediction process. In some examples, the deterioration risk assessor further stores the predicted values for the patient parameters in the clinical data store.

In act 506, the deterioration risk assessor initiates a risk assessment engine (e.g., the risk assessment engine 400) and passes the patient parameters received and generated in the acts 502 and 504 to the risk assessment engine. Within the act 506, the risk assessment engine identifies and executes a deterioration risk assessment process. The particular deterioration risk assessment process executed by the risk assessment engine may vary between examples. Some examples of deterioration risk assessment processes identified and executed by the risk assessment engine within the act 506 are illustrated in FIG. 6.

Figure 6:
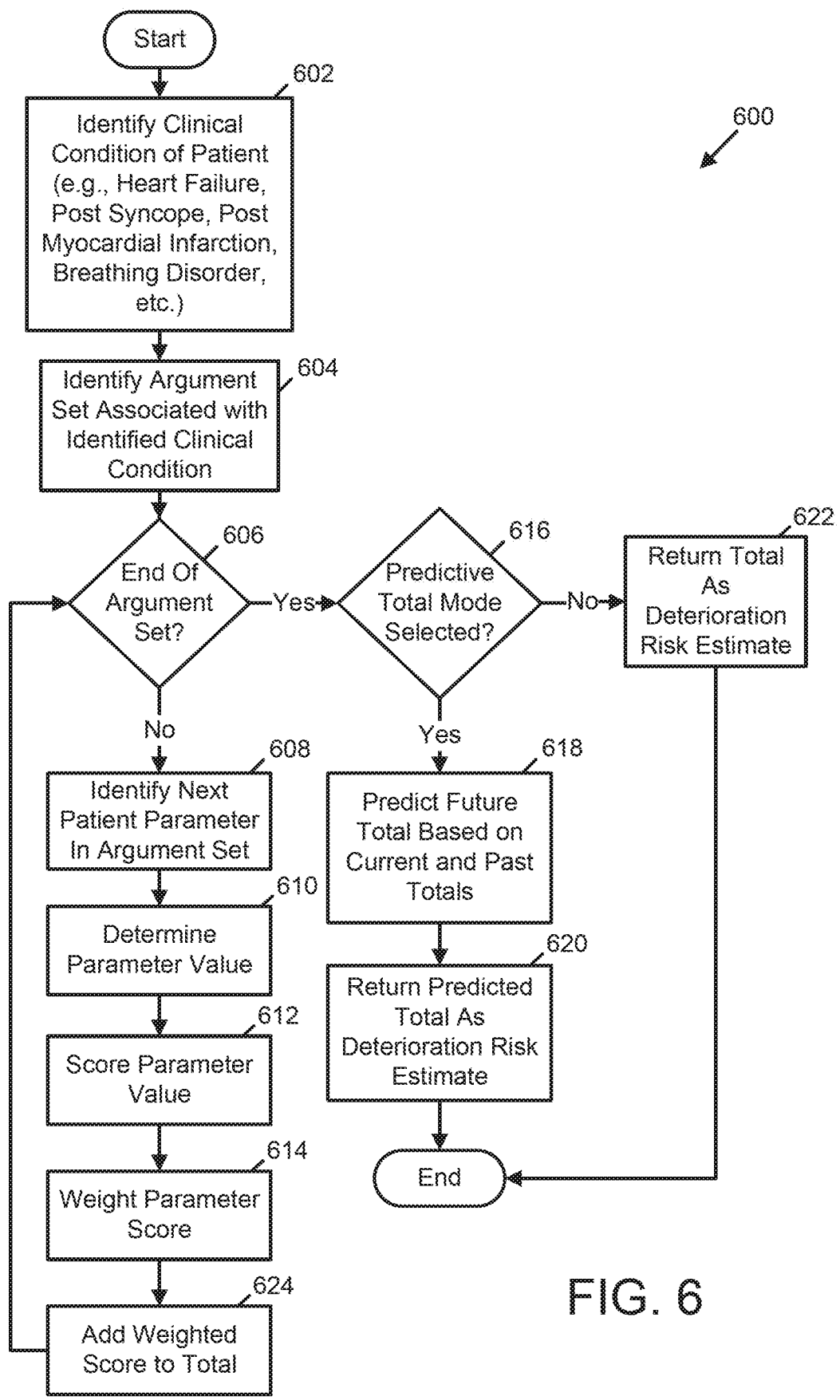
FIG. 6 depicts a deterioration risk assessment process executed by the deterioration risk assessor illustrated in FIG. 4 in accordance with at least one example disclosed herein.

As shown in FIG. 6, a deterioration risk assessment process 600 starts in act 602 with the risk assessment engine identifying the clinical condition of the patient. In some examples, the clinical condition of the patient is identified via manual entry by a caregiver via the user interface and received by the deterioration risk assessor in the act 502. In some examples, the risk assessment engine automatically determines the clinical condition of the patient by analyzing the patient parameters. The patient parameters analyzed may include sensor data (e.g., ECG data), additional physiologic data (e.g., respiration rate), medical history data, and/or demographic data.

For instance, in some examples, the risk assessment engine analyzes the common set of patient parameters listed in the argument sets illustrated in Tables 2 through 5. In these examples, the risk assessment engine identifies any abnormal patient parameters. These abnormal patient parameters may include any patient parameter that has a value falling outside a predefined range of values corresponding to the patient parameter and indicative of a patient at low risk of deterioration. Thus, abnormal patient parameters may include any patient parameter with a value that maps to a non-zero score as shown in Tables 2 through 5.

Continuing with this example, the risk assessment engine next identifies a clinical condition of the patient by identifying a clinical condition to which the abnormal patient parameters are important. For instance, the risk assessment engine may match the abnormal patient parameters to an argument set that weighs the abnormal patient parameters more heavily. For example, where the abnormal patient parameters include heart rate, heart rate variability, and ectopic activation or contractions, the risk assessment engine may identify the clinical condition of the patient as heart failure. In another example, where the abnormal patient parameters include all of the common patient parameters, the risk assessment engine may identify the clinical condition of the patient as post-syncope. In another example, where the abnormal patient parameters include heart rate, heart rate variability, ectopic activation or contractions, oxygenation, blood pressure, and electromechanical parameters, the risk assessment engine may identify the clinical condition of the patient as post-MI. In another example, where the abnormal patient parameters include respiration, oxygenation, SMO2, and cerebral oxygenation, the risk assessment engine may identify the clinical condition of the patient as breathing disorders. In some examples, after automatically identifying the clinical condition of the patient, within the act 602 the risk assessment engine prompts the caregiver to confirm the clinical condition of the patient via the user interface.

In certain implementations, for patients identified as heart failure patients, the device may further identify a heart failure classification. For example, a heart failure parameter may be used to indicate a category or classification of the patient's heart failure status. Table 6 below provides an example set of heart failure patient categories, threshold ranges, and current patient condition information.

TABLE 6

| Heart failure category | Heart failure parameter | Sample patient current condition |
|---|---|---|
| Category 1 | 1 | Stable, good condition - No concerns about patient condition. Patients at risk for heart failure who have not yet developed structural heart changes (e.g., those with diabetes and/or coronary disease) |
| Category 2 | 2 | Stable but certain metrics appear elevated - patient under observation; Patients with structural heart disease (e.g., reduced ejection fraction or chamber enlargement) |
| Category 3 | 3 | Patient condition is concerning - close/more frequent observations and response to treatment plan warranted |
| Category 4 | 4 | Overnight hospital stay in non-ED has been recommended to bring certain parameters under control; Patients who have developed clinical heart failure. Close/more frequent observations and response to treatment plan warranted |
| Category 5 | 5 | Admit to hospital ED; Patients with refractory heart failure requiring e.g., biventricular pacemakers, left ventricular assist device, transplantation |

In some implementations, the above heart failure parameters may be based on a proprietary scoring scheme for implementation in a proprietary device in accordance with the embodiments described herein. In certain other implementations, processes may automatically classify or score patients in accordance with heart failure classifications adopted by a physician's or hospital group, association, or other regulatory authority. For instance, based on the patient's medical history and current physiological parameters, the device may automatically classify the patient as a category 2 or a category 3 in accordance with predetermined criteria stored in clinical condition data store 402. For example, the device may implement heart failure classification standards prescribed by authorities such as the American College of Cardiology (ACC), the American Heart Association (AHA), and the New York heart Association (NYHA). In this regard, the device may automatically classify the patients based on similar scoring schemes as noted above into the appropriate classes and/or stages of heart failure. In some implementations, a user may configure in advance via a user set parameter which classification scheme the device is to implement. For example, a user may be prompted at set up to indicate a classification scheme in accordance with one or more the below options. The user may indicate their option via a user interface (e.g., either locally, on the device, or via a remote configuration parameter on a server that is then transmitted to the device).

1. Proprietary scoring scheme (as described above)
2. ACC/AHA scheme
3. NYHA scheme ACC/AHA scheme can be implemented as follows:

Stage A: Patients at risk for heart failure who have not yet developed structural heart changes (i.e. those with diabetes, those with coronary disease without prior infarct)

Stage B: Patients with structural heart disease (i.e. reduced ejection fraction, left ventricular hypertrophy, chamber enlargement) who have not yet developed symptoms of heart failure Stage C: Patients who have developed clinical heart failure Stage D: Patients with refractory heart failure requiring advanced intervention (i.e. biventricular pacemakers, left ventricular assist device, transplantation)

In act 604, the risk assessment engine identifies an argument set associated with the clinical condition identified in the act 602 for implanting a risk assessment process related to the clinical condition. For instance, in some examples, the risk assessment engine finds an identifier of the clinical condition within a cross-reference data structure stored within a clinical condition data store (e.g., the clinical condition data store 402) and retrieves an identifier of the argument set stored in association with the identifier of the clinical condition within the cross-reference data structure. This argument set identified may be any of the argument sets described above with reference to Tables 2 through 5. Also, within the act 604, the risk assessment engine parses the argument set to identify the patient parameters, weights, and scoring criteria referenced therein.

In act 606, the risk assessment engine determines whether its processing has reached the end of the identifiers of the patient parameters listed in the argument set identified and parsed in the act 604. If so, no listed parameter identifier remains unprocessed, and the risk assessment engine executes act 616. Otherwise, at least one listed parameter identifier remains unprocessed, and the risk assessment engine executes act 608.

In the act 608, the risk assessment engine identifies the next, unprocessed parameter identifier in the argument set. In act 610, the risk assessment engine determines a value of the patient parameter identified by the unprocessed parameter identifier. In some examples, the risk assessment engine determines this value by accessing the patient parameters provided to the risk assessment engine by the deterioration risk assessor. In act 612, the risk assessment engine scores the value with reference to the scoring criteria associated with the unprocessed parameter identifier in the argument set. For instance, the risk assessment engine may determine a score associated with the value within a scoring scale listed within the scoring criteria.

In act 614, the risk assessment engine weights the score generated in the act 612 by, for example, multiplying the score by a weight associated with the unprocessed parameter identifier in the argument set. In act 624, the risk assessment engine adds the weighted score to a running total of scores determined for each patient parameter identifier listed in the argument set and returns to the act 606.

In act 616, the risk assessment engine determines whether it has been configured to execute in predictive total mode. If so, the risk assessment engine executes act 618. If the risk assessment engine has been configured to execute in non-predictive total mode, the risk assessment engine executes act 622.

In the act 618, the risk assessment engine predicts a future total based on the total calculated on the last iteration of the act 616 and previously calculated totals for the patient. The prediction process executed by the risk assessment engine may vary between examples. For instance, in some examples, the prediction process is a simple extrapolation or linear regression process designed to surface an overall time trend evident within the totals. In some examples, more sophisticated time series analysis of the past and current totals may be employed within the prediction process.

In act 620, the risk assessment engine returns the predicted total as a deterioration risk estimate, and the deterioration risk assessment process 600 ends. The predictive total mode of operation and acts 618 and 620 may be particularly useful, for example, where the underlying patient parameters received by the risk assessment engine include actual observations rather than predicted values.

In act 622, the risk assessment engine returns the total calculated on the last iteration of the act 616 as a deterioration risk estimate, and the deterioration risk assessment process 600 ends. The non-predictive total mode of operation and act 622 may be particularly useful, for example, where the underlying patient parameters received by the risk assessment engine include predicted values rather than actual observations.

In some examples, prior to returning a deterioration risk assessment, the risk assessment engine further adjusts the risk estimate based on patient medical history and demographic data. In these examples, the risk assessment engine increases (e.g., 5%, 10%, or 15%) the deterioration risk estimate in the presence of advanced age (e.g. 70 years) and other information (e.g., patient reports shortness of breath) and/or a history of heart ailments (MI's, fibrillation, etc.).

In certain examples, the deterioration risk estimate generated by the risk assessment engine indicates a risk of rapid patient deterioration. For instance, patient deterioration may be rapid where intervention by a MERT will be required within a specified upcoming period of time. The specified upcoming period of time may include, for example, less than 1 hour, 1-2 hours, 2-4 hours, 4-6 hours, 6-8 hours, 8-12 hours, and/or 12-24 hours. The period of time of less than 1 hour can be, for example, 1 minute to 1 hour, 5 minutes to 1 hour, 10 minutes to 1 hour, or 15 minutes to 1 hour. Alternatively or additionally, patient deterioration may be rapid where the overall health of the patient (as reflected in one or more patient parameters) is in continuous decline during one of the periods of time specified above or where the overall health of the patient declines steeply (e.g., 5%-10% decline, 10%-20% decline, etc.) within one of the periods of time specified above.

While the deterioration risk assessment process 600 described with reference to FIG. 6 returns a risk estimate of patient deterioration in the form of a numerical value, not all deterioration risk assessment processes in accordance with this disclosure are formed of a numerical value. For instance, some deterioration risk assessments processes may return name value pairs, ranges of numerical values, vectors, or other data indicative of a patient's risk of deterioration.

Returning to the monitoring and treatment process 500 illustrated in FIG. 5, in act 508 the deterioration risk assessor determines whether the risk estimate of patient deterioration returned by the risk assessment engine falls outside one or more clinical criterion associated with the clinical condition of the patient. Within the act 508, the deterioration risk assessor may identify the one or more clinical criterion via a cross-reference data structure stored in the clinical condition data store that includes associations between a presentable clinical condition, a deterioration risk assessment process, and one or more clinical criterion. In some examples of the act 508, the deterioration risk assessor compares the one or more clinical criterion to the risk estimate of patient deterioration. For instance, the deterioration risk assessor may compare a threshold value to the risk estimate of patient deterioration and determine that the risk estimate falls outside the one or more clinical criterion where a value in the risk estimate exceeds the threshold value. In another example, the deterioration risk assessor may compare a range of values to a slope calculated for a series of risk estimates and determine that the risk estimate falls outside the one or more clinical criterion where the slope falls outside the range of values. In another example, the deterioration risk assessor may compare a set of elements to the risk estimate and determine that a value in the risk estimate is not present within the set of elements. Regardless of the comparison made, where the comparison indicates that the risk estimate falls outside the one or more clinical criterion, the deterioration risk assessor executes act 510. Where the comparison indicates that the risk estimate does not fall outside the one or more clinical criterion, the deterioration risk assessor returns to the act 502.

In act 510, the deterioration risk assessor executes a predefined, configurable action such as notifying a caregiver, prompting the patient for information and/or to conduct a neurologic test of the patient. Subsequent to the act 510, the monitoring and treatment process 500 returns to the act 502 and continues to monitor the patient's parameters.

The monitoring and treatment process 500 enables medical devices to monitor in-hospital patients at risk for deterioration including rapid deterioration and, in at least some instances, take preventive measures before an adverse event occurs and/or when the risk becomes unacceptable according to an appropriate standard of care. While the monitoring and treatment process 500 is illustrated in FIG. 5 as starting with the act 502, in some examples, subsequent iterations of the monitoring and treatment process 500 start with the act 504. Further, in some examples, the deterioration risk assessor 420 is configured to initiate these subsequent iterations according to a schedule that may be modified via the user interface 308. Additionally or alternatively, in some examples. The deterioration risk assessor 420 is configured to initiate a complete iteration of the monitoring and treatment process 500 "on demand" upon receiving an express request to do so via the user interface 308 or in response to receiving an update to patient parameters via the user interface 308. It is appreciated that the clinical condition of the patient may change between the first iteration and subsequent iterations, in which case the deterioration risk assessment process executed by the risk assessment process would change as well.

Figure 7:
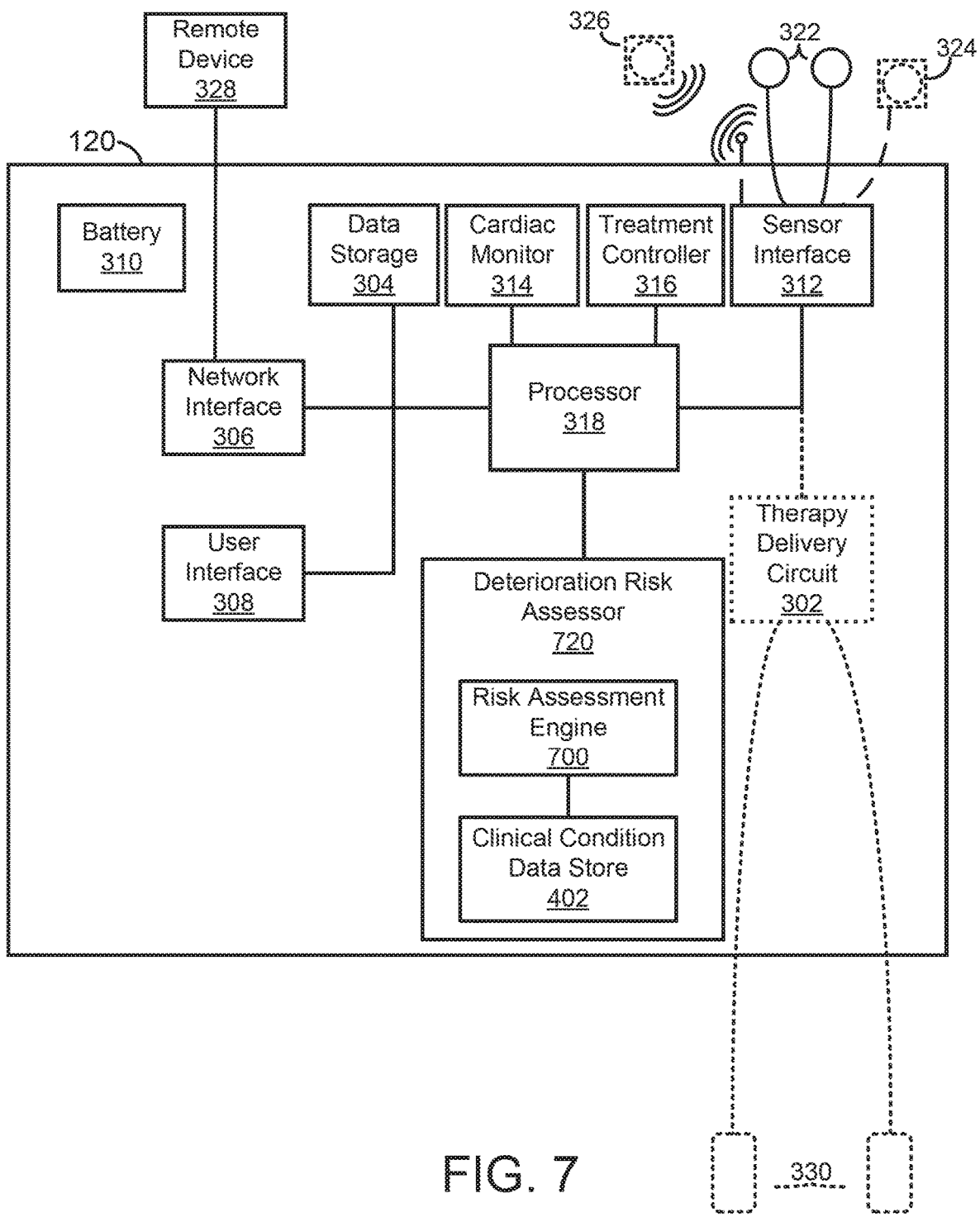
FIG. 7 depicts a second example of a deterioration risk assessor within the context of the medical device controller illustrated in FIG. 3 in accordance with at least one example disclosed herein.

Some example medical devices disclosed herein include a deterioration risk assessor that incorporates and further refines the deterioration risk assessor 420. In these examples, the deterioration risk assessor is further configured to receive and/or generate a robust initial set of patient parameters, use the robust initial set to execute an initial iteration of a deterioration risk assessment process, receive and/or generate a subset of the robust initial set, and use the subset to execute subsequent iterations of the deterioration risk assessment process. FIG. 7 illustrates an example medical device controller (e.g., the medical device controller 120) that includes a deterioration risk assessor 720 configured in accord with these examples. As shown, the deterioration risk assessor 720 includes a risk assessment engine 700, and the clinical condition data store 402. In at least some embodiments, the risk assessment engine 700 incorporates and further refines the risk assessment engine 400.

In some examples, to execute a deterioration risk assessment process, the deterioration risk assessor 720 is configured to initiate the risk assessment engine 700 and provide the risk assessment engine 700 with a set of patient parameters. The patient parameters included in the set may vary from a robust set to some subset of the robust set. For instance, a robust set of patient parameters may include continuously monitored patient parameters, periodically monitored patient parameters, and irregularly monitored patient parameters. A subset of the robust set may be a proper subset and may include parameters from any one of these groups and/or individual parameters from one or more of these groups. In some examples, the deterioration risk assessor 720 is configured to initiate the risk assessment engine 700 and provide the risk assessment engine 700 with a robust set of patient parameters and to subsequently re-initiate the risk assessment engine 700 with a subset of the robust set. Subsequent re-initiations may be in response to a predefined, configurable schedule (e.g., every 4-8 hours) or in response to an event (e.g. availability of new values of patient parameters).

Figure 8:
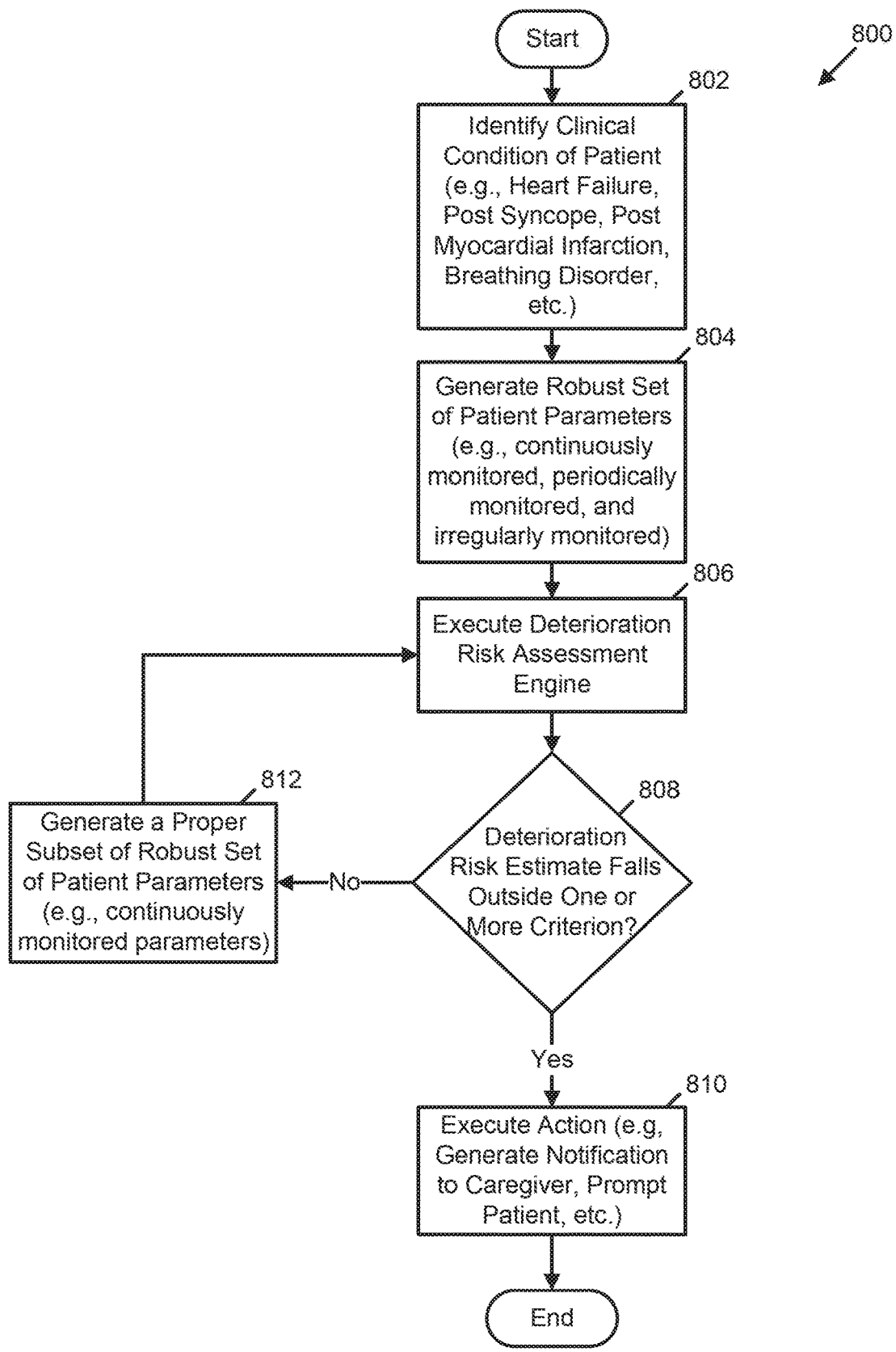
FIG. 8 depicts a monitoring and treatment process executed by the deterioration risk assessor illustrated in FIG. 7 in accordance with at least one example disclosed herein.

In some examples, medical devices including a deterioration risk assessor (e.g., the deterioration risk assessor 720) may execute the processes illustrated above with reference to FIGS. 5 and 6. Alternatively or additionally, some example medical devices including the deterioration risk assessor are configured to execute a monitoring and treatment process 800 illustrated in FIG. 8. As shown in FIG. 8, the monitoring and treatment process 800 starts in act 802 with the deterioration risk assessor identifying a clinical condition of a patient. This clinical condition may be, for example, heart failure condition, a post syncope condition, a post myocardial infarction condition, or a breathing disorder condition, among the clinical conditions. In some examples of the act 802, the deterioration risk assessor identifies the clinical condition of the patient by analyzing a set of patient parameters provided within initial patient assessment data. This initial patient assessment data may be received via a user interface (e.g., the user interface 308) and/or automatically determined from other sources (e.g., the sensor interface 312). The analysis performed by the deterioration risk assessor may range from simply parsing the initial patient assessment data to locate an identifier of the clinical condition of the patient (e.g., as input by a caregiver via the user interface) to processing other patient parameters within the initial assessment data to classify the clinical condition of the patient (e.g., as described above with reference to the act 602).

In act 804, the deterioration risk assessor generates a robust set of patient parameters from the initial assessment data and other data (e.g., sensor data) descriptive of the patient parameters. In some examples, within the act 804, the robust set is generated by parsing and processing the initial assessment and other data. The patient parameters generated within the act 804 include continuously monitored, periodically monitored, and continuously monitored parameters described above.

In some examples, the patient parameters are collected from a caregiver and/or a variety of specialized medical devices as part of triaging a patient at a healthcare facility. For instance, some parameters (neurologic state, pallor, etc.) of the robust set of patient parameters generated in the act 804 may originate from a scripted patient assessment conducted by a caregiver. Other parameters (resting heart rate, blood pressure, respiration rate, body temperature, etc.) of the robust set of patient parameters generated in the act 804 may originate from specialized and dedicated ECG monitors, blood pressure monitors, and the like. Many of these specialized devices may be unattached and withdrawn over time, eventually being replaced by a single wearable, ambulatory, external medical device as monitoring of the patient progresses.

Further, in some examples of the act 804, in generating the patient parameters, the deterioration risk assessor executes a prediction process that generates predicted values for the patient parameters that are based on the observations reported in the sensor data and observations reported in previously received sensor data. The prediction process executed by the deterioration risk assessor may vary between examples. For instance, in some examples, the prediction process is a simple extrapolation or linear regression process designed to identify an overall time trend latent within the sensor data. In some examples, more sophisticated time series analysis of the past and current sensor data may be employed within the prediction process.

In act 806, the deterioration risk assessor initiates a risk assessment engine (e.g., the risk assessment engine 700) and passes the patient parameters generated in the acts 804 to the risk assessment engine. Within the act 806, the risk assessment engine executes a deterioration risk assessment process. The particular deterioration risk assessment process executed by the risk assessment engine may vary between examples. Some examples of deterioration risk assessment processes executed by the risk assessment engine within the act 806 are illustrated in FIG. 6.

In act 808 the deterioration risk assessor determines whether the risk estimate of patient deterioration returned by the risk assessment engine falls outside one or more clinical criterion associated with the clinical condition of the patient. If the risk estimate does not fall outside the one or more clinical criterion, the deterioration risk assessor executes act 812. If the risk estimate falls outside the one or more clinical criterion, the deterioration risk assessor executes act 810.

In act 810, the deterioration risk assessor executes a predefined, configurable action such as notifying a caregiver, prompting the patient for information and/or to conduct a neurologic test of the patient. Subsequent to the act 810, the monitoring and treatment process 800 ends.

In act 812, the deterioration risk assessor generates a subset of the robust set of patient parameters. This subset of the robust set may be a proper subset and may include parameters from any of the continuously monitored, periodically monitored, and continuously monitored parameters described above. This subset of the robust set may be generated by a single wearable, ambulatory, external medical device such as that illustrated in FIG. 2 above. In some examples of the act 812, the deterioration risk assessor delays generation of the subset according to a predefined, configurable schedule (e.g., every 4-8 hours) or until detection of an event (e.g. availability of new values of patient parameters).

The monitoring and treatment process 800 enables medical devices to monitor in-hospital patients at risk for deterioration and, in at least some instances, take preventive measures when the risk becomes unacceptable according to an appropriate standard of care.

Figure 9:
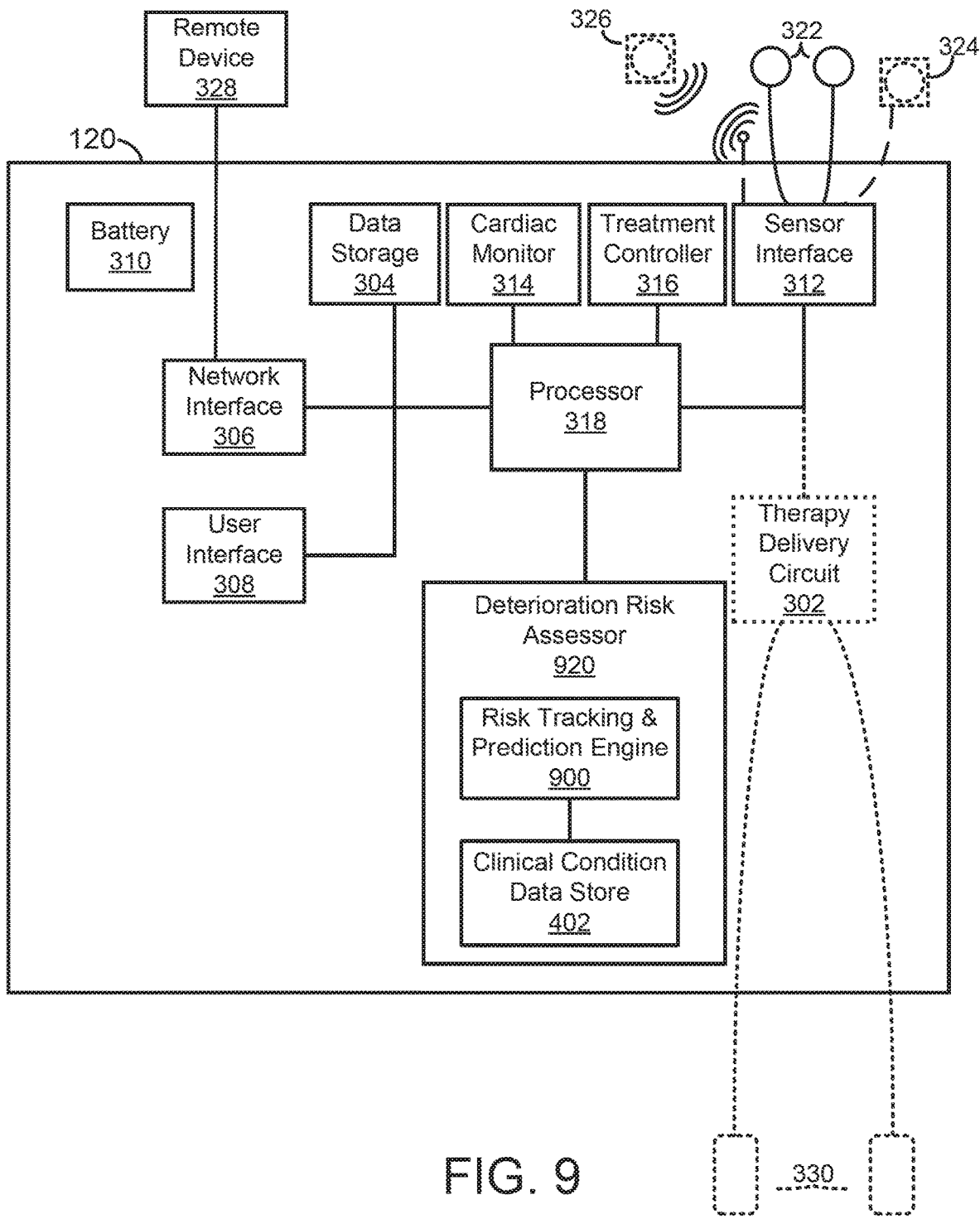
FIG. 9 depicts a third example of a deterioration risk assessor within the context of the medical device controller illustrated in FIG. 3 in accordance with at least one example disclosed herein.

Some example medical devices disclosed herein include a deterioration risk assessor that incorporates and further refines the deterioration risk assessor 420 to generate a trajectory of a patient's clinical condition. In these examples, the deterioration risk assessor is further configured to construct (e.g., receive and/or generate) an initial set of patient parameters and to use the initial set to execute a patient deterioration risk tracking and prediction process that generates a risk estimate of patient deterioration that includes the trajectory of the patient's clinical condition. In these examples, the criterion or criteria used by the deterioration risk assessor to determine whether further action is warranted includes one or more benchmark trajectories. In these examples, the deterioration risk assessor compares the trajectory of the patient's clinical condition to the one or more benchmark trajectories to determine a degree of similarity (e.g., cosine similarity) between them. These benchmark trajectories may include trajectories having an unacceptable level of risk of patient deterioration. The deterioration risk assessor is also further configured to execute an action associated with the benchmark trajectory (e.g., within a cross-reference data structure) where the degree of similarity is sufficient (e.g., transgresses a threshold value). The actions associated with the benchmark trajectories may be any of the further actions described herein. FIG. 9 illustrates an example medical device controller (e.g., the medical device controller 120) that includes a deterioration risk assessor 920 configured in accord with these examples. As shown, the deterioration risk assessor 920 includes a risk tracking and prediction engine 900, and the clinical condition data store 402.

In some examples, to execute a patient deterioration risk tracking and prediction process, the deterioration risk assessor 920 is configured to initiate the risk tracking and prediction engine 900 and provide the risk tracking and prediction engine 900 with a set of patient parameters. The set of parameters may be provided in the form of a multidimensional vector. The patient parameters included in the set may vary between initiations of the risk tracking and prediction engine 900. For instance, an initial set may include continuously monitored patient parameters, periodically monitored patient parameters, and irregularly monitored patient parameters. A subsequent set may include a subset of the initial set. In some examples, the deterioration risk assessor 920 is configured to initiate the risk tracking and prediction engine 900 as new values of patient parameters become available.

Figure 10:
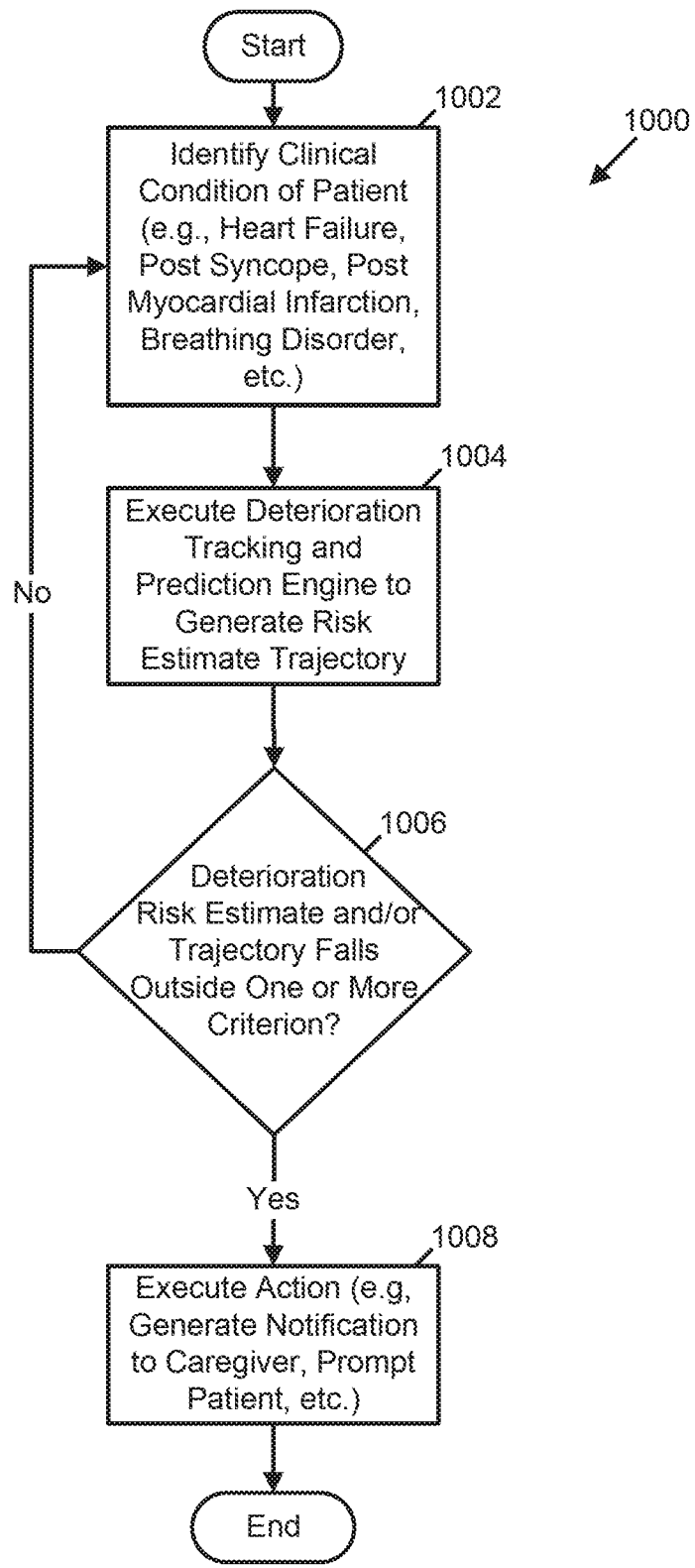
FIG. 10 depicts a monitoring and treatment process executed by the deterioration risk assessor illustrated in FIG. 9 in accordance with at least one example disclosed herein.

In some examples, medical devices including a deterioration risk assessor (e.g., the deterioration risk assessor 920) may execute the processes illustrated above with reference to FIGS. 5 and 6. Alternatively or additionally, some example medical devices including the deterioration risk assessor are configured to execute a monitoring and treatment process 1000 illustrated in FIG. 10. As shown in FIG. 10, the monitoring and treatment process 1000 starts in act 1002 with the deterioration risk assessor identifying a clinical condition of a patient. This clinical condition may be, for example, heart failure condition, a post syncope condition, a post myocardial infarction condition, or a breathing disorder condition, among the clinical conditions. In some examples of the act 1002, the deterioration risk assessor identifies the clinical condition of the patient by analyzing a set of patient parameters provided within initial patient assessment data. This initial patient assessment data may be received via a user interface (e.g., the user interface 308) and/or automatically determined from other sources (e.g., the sensor interface 312). The analysis performed by the deterioration risk assessor may range from simply parsing the initial patient assessment data to locate an identifier of the clinical condition of the patient (e.g., as input by a caregiver via the user interface) to processing other patient parameters within the initial assessment data to classify the clinical condition of the patient (e.g., as described above with reference to the act 602).

In some examples of the act 1002, the deterioration risk assessor receives a previously generated risk estimate of patient deterioration that includes a trajectory of the patient's clinical condition. This trajectory may be expressed as an ensemble of trajectories, as will be described further below. In these examples of the act 1002, the deterioration risk assessor processes the received trajectory to determine whether a change to the clinical condition of the patient is warranted. For instance, in some examples, the received trajectory is compared to one or more benchmark trajectories to determine a degree of similarity (e.g., cosine similarity) between them. These benchmark trajectories may include trajectories representative of various clinical conditions. Where the degree of similarity between the received trajectory and a benchmark trajectory (e.g., associated with a clinical condition different from the recorded clinical condition of the patient) is sufficient (e.g., 0.4, 0.5, 0.6, 0.7, or 0.8 in some examples), the deterioration risk assessor is also further configured to change the recorded clinical condition of the patient to the clinical condition associated with the benchmark trajectory. Alternatively or additionally, the deterioration risk assessor may prompt a caregiver to confirm this change via the user interface.

Figure 11:
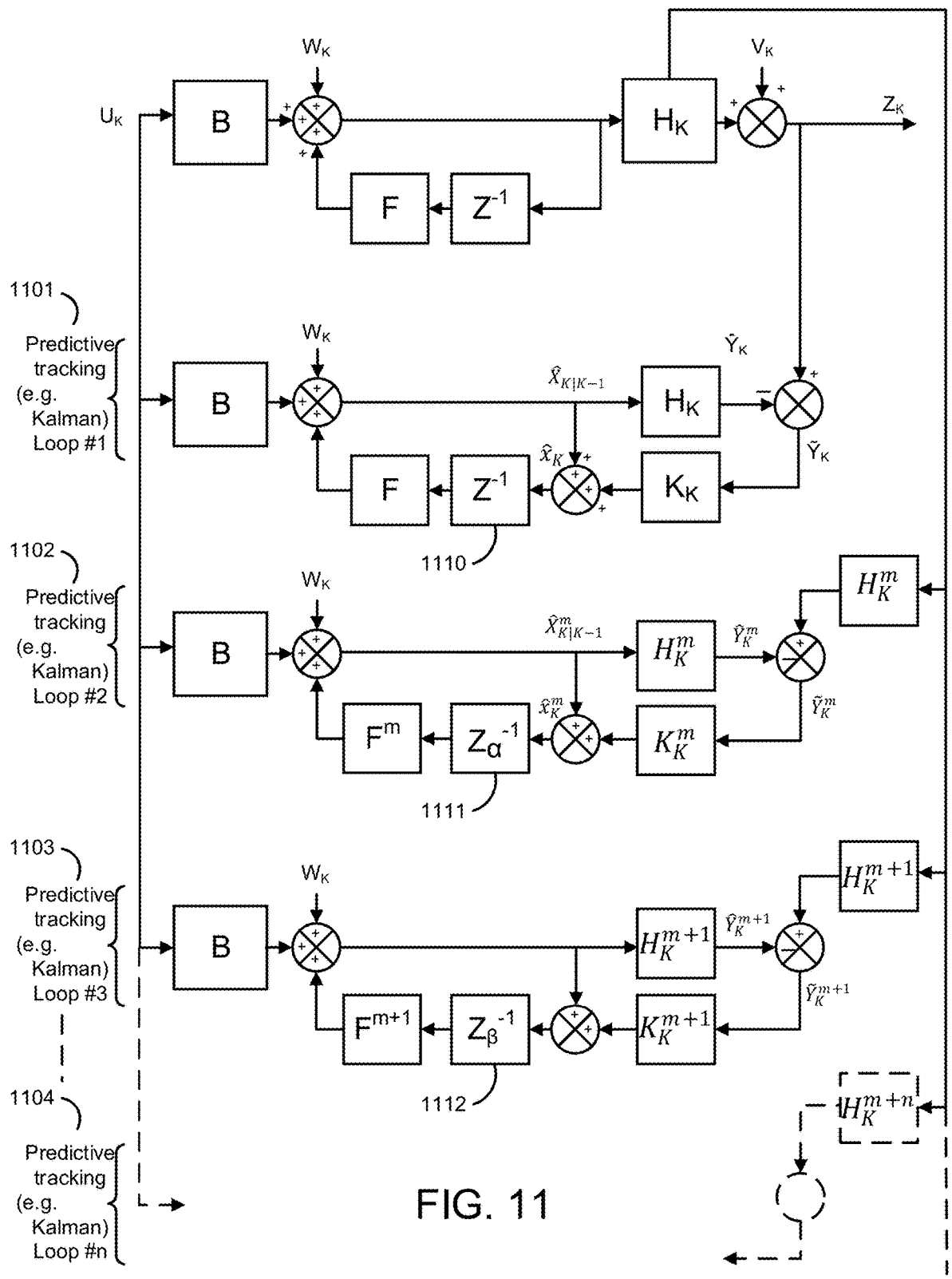
FIG. 11 depicts a block diagram of a Kalman filter enhanced to implement the monitoring and treatment process illustrated in FIG. 10.
Figure 12:
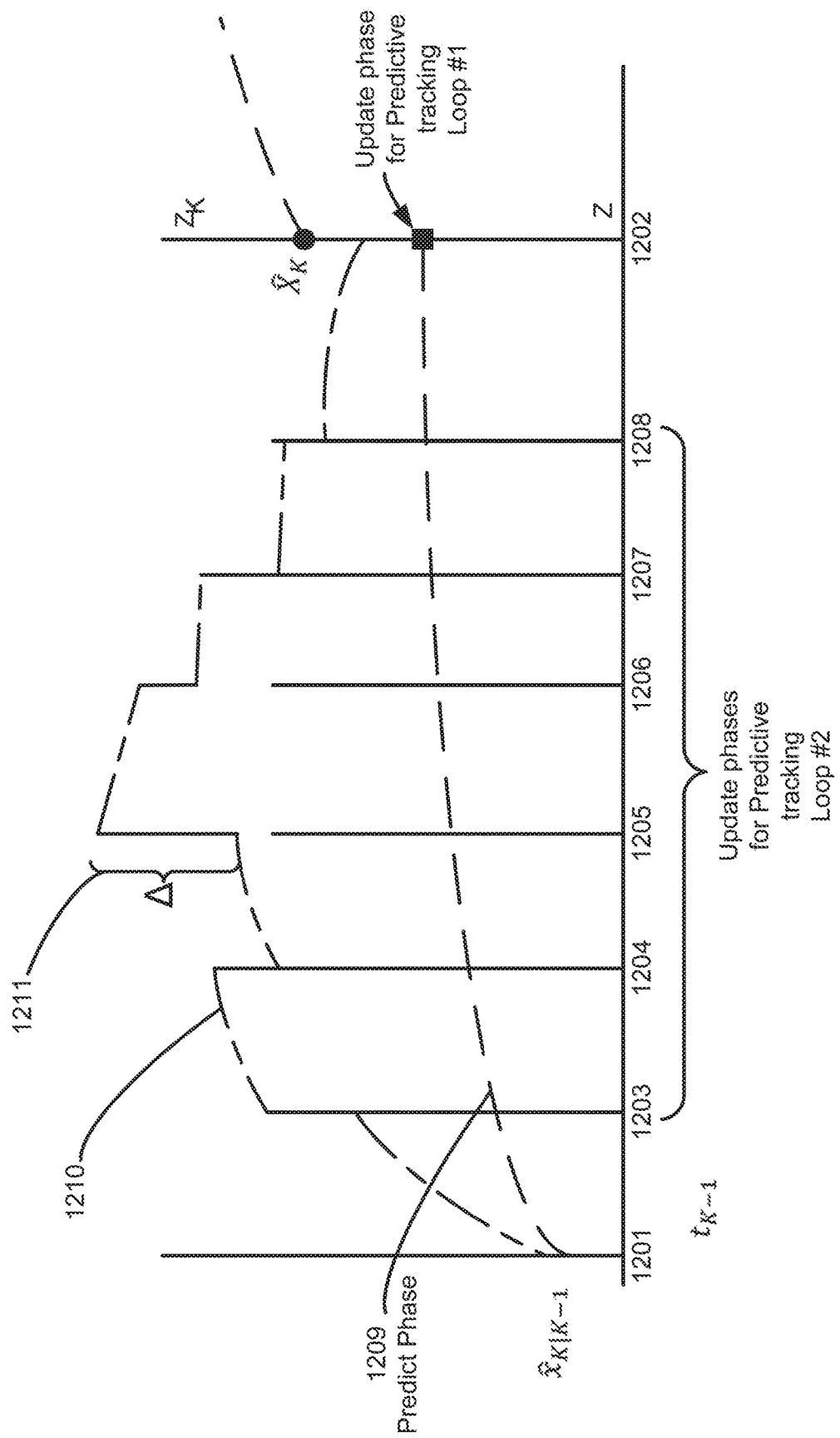
FIG. 12 graphically depicts results of execution of the enhanced Kalman filter illustrated in FIG. 11.

In act 1004, the deterioration risk assessor initiates a risk tracking and prediction engine (e.g., the risk tracking and prediction engine 900) and passes patient parameters generated from the initial patient assessment data, or from other data sources described herein as data becomes available, to the risk tracking and prediction engine. Also within the act 1004, the risk tracking and prediction engine executes a deterioration risk tracking and prediction process. The particular deterioration risk tracking and prediction processes executed by the risk assessment engine may vary between examples. Some examples of deterioration risk tracking and prediction processes executed by the risk tracking and prediction engine within the act 1004 are illustrated in FIGS. 11 and 12, which are described further below.

As described above, in some examples, there are patient parameters that are continuously monitored, such as T-wave measurements, heart rate, QRS width, pulse oximetry saturation, or other physiologic parameter measurements. These patient parameters may be contrasted with patient parameters of events that are of discrete occurrences, such as ectopic beats. Therefore, in some examples, patient parameters that are measured and monitored on a more continuous basis may be used to increase the accuracy of the risk estimate of patient deterioration. In these examples, the risk tracking and prediction engine models a multidimensional patient parameter space this is M-dimensional, where $M=J+K\pm L$, where J is a number of elements of subject history and demographics; K is a number of physiologic parameters, such as vital sign measures, ECG, SpO2, respiration rate, etc.; and L is a number of different event types. Within this model, a 1×M dimensional vector traces a trajectory in space, where the rate of update of the individual patient parameters may be: 1) regular and continuous, such as with a machine-sampled sensor input, e.g., ECG; 2) semi-regular and periodic, such as with a vital signs parameter measured and input manually by a nurse or other caregiver; or 3) irregular events.

Using the M-dimensional patient parameter space, a tracking process used for such applications as missile and satellite tracking, for example, a Kalman filter or a particle filter, may be used for estimation and prediction of the vector loop path. The location of the most recent event along with the estimate of the trajectory's direction and path are used to estimate the risk and degree of certainty (e.g. the confidence band) of deterioration of a patient's clinical condition occurring at some point in the future. As more events of various types occur, the trajectory path and the estimate of the trajectory path into the future may be better estimated, and the confidence band on the estimate may be narrowed for more certainty in the risk estimate.

A Kalman filter estimates a process by using a form of feedback control. The Kalman filter estimates the process state at some time and then obtains feedback in the form of (noisy) measurements. As such, the equations for the Kalman filter fall into two groups: time update equations and measurement update equations. The time update equations are responsible for projecting forward (in time) the current state and error covariance estimates to obtain the a priori estimates for the next time stage. The measurement update equations are responsible for the feedback, i.e., for incorporating a new measurement into the a priori estimate to obtain an improved a posteriori estimate. The time update equations may also be thought of as predictor equations, while the measurement update equations may be thought of as corrector equations. Indeed, the final estimation process resembles that of a predictor-corrector process for solving numerical problems.

In some examples, to use an enhanced Kalman filter to estimate the internal state of a process, the risk tracking and prediction engine maintains the following matrices: $F_k$, which is a state-transition model; $H_k$, which is an observation model; $Q_k$, which models covariance of process noise; $R_k$, which models covariance of observation noise; and sometimes $B_k$, which is a control-input model, for each time-step, k. The enhanced Kalman filter model assumes a true state at time k is derived from a state at time (k−1) according to Equation (1):

$$x_k = F_k x_{k-1} + B_k u_k + w_k \quad (1)$$

wherein $F_k$ is a state transition model applied to the previous state $x_{k-1}$; $B_k$ is the control-input model which is applied to the control vector $u_k$; $w_k$ is the process noise model which assumes a zero mean multivariate normal distribution with covariance $Q_k$, i.e., $w_k \sim N(0, Q_k)$.

At time k an observation value (or measurement) $z_k$ of the true state $x_k$ is made according to Equation (2):

$$z_k = H_k x_k + v_k \quad (2)$$

wherein $H_k$ is the observation model which maps the true state space into the observed space and $v_k$ is the observation noise model which assumes zero mean Gaussian white noise with covariance $R_k$, i.e., $v_k \sim N(0, R_k) v_k$. The initial state, and the noise vectors at each step $\{x_0, w_1, \ldots w_k, v_1 \ldots v_k\}$ are all assumed to be mutually independent.

Kalman filters are recursive in that the estimated state from the previous time step and the current measurement are used to compute an estimate of the current state. In contrast to other estimation processes, no historical data is required.

In some examples, states of the enhanced Kalman filter are represented by two variables. The first of these two variables is $\hat{x}_{k|k}$, which is a posteriori state estimate at time k given observations up to and including at time k. Please note that the notation $\hat{x}_{n|m}$ represents an estimate of x at time n given observations up to, and including at time m≤n. The second of these two variables is $P_{k|k}$, which is a posteriori error covariance matrix. The posteriori error covariance matrix is a measure of the estimated accuracy of the state estimate.

The enhanced Kalman filter can be understood as having two distinct phases: a predict phase and an update phase. The predict phase processes the state estimate from the previous time-step to generate an estimate of the state at the current time-step. This predicted state estimate is also known as the a priori state estimate. This is so because the a priori state estimate does not include observation information from the current time-step. In the update phase, the current a priori estimate is combined with current observation information to generate the a posteriori state estimate.

In some examples, the two phases alternate, with the prediction phase generating a state estimate until the next observation, and with the update phase incorporating the next observation to generate another state estimate. However, where an observation is unavailable, some examples omit the update phase and, instead, execute multiple consecutive prediction phases. Similarly, where multiple independent observations are available contemporaneously, some examples execute multiple update phases using different observation matrices.

The predicted (a priori) state estimate may be represented by the following Equation (3):

$$\hat{x}_{k|k-1} = F_k \hat{x}_{k-1|k-1} + B_k u_k \quad (3)$$

The predicted (a priori) estimate covariance may be represented by the following Equation (4):

$$P_{k|k-1} = F_k P_{k-1|k-1} F_k^T + Q_k \quad (4)$$

The innovation or measurement residual may be represented by the following Equation (5):

$$\tilde{y}_k = z_k - H_k \hat{x}_{k|k-1} \quad (5)$$

The innovation (or residual) covariance may be represented by the following Equation (6):

$$S_k = H_k P_{k|k-1} H_k^T + R_k \quad (6)$$

The optimal Kalman gain may be represented by the following Equation (7):

$$K_k = P_{k|k-1} H_k^T S_k^{-1} \quad (7)$$

The updated (a posteriori) state estimate may be represented by the following Equation (8):

$$\hat{x}_{k|k} = \hat{x}_{k|k-1} + K_k \tilde{y}_k \quad (8)$$

The updated (a posteriori) estimate covariance may be represented by the following Equation (9):

$$P_{k|k} = (I - K_k H_k) P_{k|k-1} \quad (9)$$

In some examples, an initial act during the update phase is to compute the enhanced Kalman gain $K_k$, and a next act is to actually measure the process to obtain and generate an a posteriori state estimate by incorporating the measurement $z_k$. A final act is to obtain an a posteriori error covariance estimate $P_k$. After each time and measurement update pair, the process is repeated with the previous a posteriori estimates used to project or predict the new a priori estimates. This recursive nature is one of the very appealing features of the enhanced Kalman filter, and it makes practical implementations much more feasible than, for example, an implementation of a Wiener filter which is designed to operate on all of the data directly for each estimate. The enhanced Kalman filter instead recursively conditions the current estimate on all of the past measurements. Equation (8) is thus termed the predictor equation.

Some examples of the risk tracking and prediction engine execute other risk tracking and prediction processes. One limitation of a Kalman filter is that it models a linear system with Gaussian distribution, which is not often encountered in the physiologic setting. Thus at least one example of the risk tracking and prediction engine executes an extended Kalman filter (EKF) to solve the problem of non-Gaussian, nonlinear filtering. The EKF is based upon the principle of linearizing the measurements and evolution models using Taylor series expansions. The series approximations in the EKF process may, however, lead to poor representations of the nonlinear functions and probability distributions of interest. As a result, the EKF may diverge.

Therefore, at least one example of the risk tracking and prediction engine executes an unscented Kalman filter (UKF) based on the hypothesis that it is easier to approximate a Gaussian distribution than it is to approximate arbitrary nonlinear functions. It has been shown that the UKF leads to more accurate results than the EKF and that it generates much better estimates of the covariance of the states (the EKF often seems to underestimate this quantity). The UKF, however, has a limitation in that it does not apply to general non-Gaussian distributions, as is often the case with ECG spectral distributions.

Consequently at least one example of the risk tracking and prediction engine executes Sequential Monte Carlo processes, also known as particle filters, overcome this limitation and allow for a complete representation of the posterior distribution of the states, so that any statistical estimates, such as the mean, modes, kurtosis and variance, may be easily computed. Particle filters may, therefore, deal with any nonlinearities or distributions. Particle filters rely on importance sampling and, as a result, require the design of proposal distributions that can approximate the posterior distribution reasonably well. In general, it is hard to design such proposals. The most common strategy is to sample from the probabilistic model of the state evolution (transition prior). This strategy, however, may fail if the new measurements appear in the tail of the prior or if the likelihood is too peaked in comparison to the prior.

Some other example risk tracking and prediction processes executed by the risk tracking and prediction engine include an estimator/predictor trajectory tracking technique known as the Unscented Particle Filter (UPF) which is disclosed by Wan, Eric A. and van der Merwe, Rudolph in "The Unscented Kalman Filter for Nonlinear Estimation" (2000). For example, the following Table 7 provides Unscented Kalman Filter (UKF) equations that may be used to track and predict patient parameters and/or risk estimates in some examples.

TABLE 7

Initialize with:
$\hat{x}_0 = E[x_0]$
$P_0 = E[(x_0 - \hat{x}_0)(x_0 - \hat{x}_0)^T]$
$\hat{x}_0^a = E[x^a] = [\hat{x}_0^T \, 0 \, 0]^T$ $$P_0^a = E[(x_0^a - \hat{x}_0^a)(x_0^a - \hat{x}_0^a)^T] = \begin{bmatrix} P_0 & 0 & 0 \\ 0 & P_v & 0 \\ 0 & 0 & P_n \end{bmatrix}$$

For $k \in \{1, \ldots, \infty\}$,
Calculate sigma points:

$$X_{k-1}^a = \left[\hat{x}_{k-1}^a \, \hat{x}_{k-1}^a \pm \sqrt{(L+\lambda)P_{k-1}^a}\right]$$

TABLE 7-continued

Time update:
$X_{k|k-1}^x = F[x_{k-1}^x, x_{k-1}^v]$
$\hat{x}_k^- = \sum_{i=0}^{2L} W_i^{(m)} X_{i,k|k-1}^x$
$P_k^- = \sum_{i=0}^{2L} W_i^{(c)} [X_{i,k|k-1}^x - \hat{x}_k^-][X_{i,k|k-1}^x - \hat{x}_k^-]^T$
$y_{k|k-1} = H[x_{k|k-1}^x, x_{k-1}^n]$
$\hat{y}_k^- = \sum_{i=0}^{2L} W_i^{(m)} y_{i,k|k-1}$ Measurement update equations:

$$P_{\tilde{y}_k \tilde{y}_k} = \sum_{i=0}^{2L} W_i^{(c)} [y_{i,k|k-1} - \hat{y}_k^-][y_{i,k|k-1} - \hat{y}_k^-]^T$$

$$P_{x_k y_k} = \sum_{i=0}^{2L} W_i^{(c)} [X_{i,k|k-1} - \hat{x}_k^-][y_{i,k|k-1} - \hat{y}_k^-]^T$$

$$K = P_{x_k y_k} P_{\tilde{y}_k \tilde{y}_k}^{-1}$$

$$\hat{x}_k = \hat{x}_k^- + K(y_k - \hat{y}_k^-)$$

$$P_k = P_k^- - K P_{\tilde{y}_k \tilde{y}_k} K^T$$

where, $x^a = [x^T \, v^T \, n^T]^T$, $x^a = [(x^x)^T (x^v)^T (x^n)^T]^T$,
$\lambda$ = composite scaling parameter, L = dimension of augmented state,
$P_v$ = process noise cov., $P_v$ = measurement noise cov.,
$W_i$ = weights as calculated by a weighting equation.

For example, for an initialization: t=0, and for i=1, ... N, draw states (particles) $x_0^{(i)}$ from the prior $p(x_0)$ and set, according to the following Equations (10), (11), (12), and (13):

$$\bar{x}_0^{(i)} = E[x_0^{(i)}] \tag{10}$$

$$P_0^{(i)} = E[(x_0^{(i)} - \bar{x}_0^{(i)})(x_0^{(i)} - \bar{x}_0^{(i)})_T] \tag{11}$$

$$\bar{x}_0^{(i)a} = E[x^{(i)a}] = [(\bar{x}_0^{(i)})_T \, 0 \, 0]^T \tag{12}$$

$$P_0^{(i)a} = E[(x_0^{(i)a} - \bar{x}_0^{(i)a})(x_0^{(i)a} - \bar{x}_0^{(i)a})_T] = \begin{bmatrix} P_0^{(i)} & 0 & 0 \\ 0 & Q & 0 \\ 0 & 0 & R \end{bmatrix} \tag{13}$$

For t=1, 2, ..., an importance sampling step: for i=1, ... N: updates particles with the UKF according to the following Equations (14), (15), (16), (17), (18), (19), (20), (21), (22), (23), and (24):

Calculate sigma points:

$$x_{t-1}^{(i)a} = [\bar{x}_{t-1}^{(i)a} \, \bar{x}_{t-1}^{(i)a} \pm \sqrt{(n_a + \lambda) P_{t-1}^{(i)a}}] \tag{14}$$

Predict Future Particle (Time Update)

$$x_{t|t-1}^{(i)x} = f(x_{t-1}^{(i)x}, x_{t-1}^{(i)v}) \quad \bar{x}_{t|t-1}^{(i)} = \sum_{j=0}^{2n_a} W_j^{(m)} X_{j,t|t-1}^{(i)x} \tag{15}$$

$$P_{t|t-1}^{(i)} = \sum_{j=0}^{2n_a} W_j^{(c)} [X_{j,t|t-1}^{(i)x} - \bar{x}_{t|t-1}^{(i)}][X_{j,t|t-1}^{(i)x} - \bar{x}_{t|t-1}^{(i)}]_T \tag{16}$$

$$\gamma_{t|t-1}^{(i)} = h(x_{t|t-1}^{(i)x}, x_{t-1}^{(i)n}) \quad \bar{y}_{t|t-1}^{(i)} = \sum_{j=0}^{2n_a} W_j^{(m)} \gamma_{j,t|t-1}^{(i)} \tag{17}$$

Incorporate New Observation (Measurement Update)

$$P_{\tilde{y}_t \tilde{y}_t} = \sum_{j=0}^{2n_a} W_j^{(c)} [y_{j,t|t-1}^{(i)} - \bar{y}_{t|t-1}^{(i)}][\gamma_{j,t|t-1}^{(i)} - \bar{y}_{t|t-1}^{(i)}]^T \tag{18}$$

-continued $$P_{x_t y_t} = \sum_{j=0}^{2n_a} W_j^{(c)} [x_{j:t|t-1}^{(i)} - \bar{x}_{t|t-1}^{(i)}][\gamma_{j:t|t-1}^{(i)} - \bar{y}_{t|t-1}^{(i)}]^T \quad (19)$$

$$K_t = P_{x_t y_t} P \frac{-1}{y_t y_t} \bar{x}_t^{(i)} = \bar{x}_{t|t-1}^{(i)} + K_t(y_{t-} \bar{y}_{t|t-1}^{(i)}) \quad (20)$$

$$\hat{P}_t^{(i)} = P_{t|t-1}^{(i)} - K_t P_{\bar{y}_t \bar{y}_t} K_t^T \quad (21)$$

Sample $\hat{x}_t^{(i)} \sim q(x_t^{(i)} | x_{0:t-1}^{(i)}, , y_{1:t}) = \mathcal{N}(\bar{x}_t^{(i)}, P_{(t)}^{(i)}) \quad (22)$ Set $\hat{x}_{0:t}^{(i)} \triangleq (x_{0:t-1}^{(i)}, \hat{x}_t^{(i)})$ and $\hat{P}_{0:t}^{(i)}(P_{0:t-1}^{(i)}, \hat{P}_t^{(i)}) \quad (23)$ For i=1, ... N, evaluate the importance weights up to a normalizing constant:

$$w_t^{(i)} \propto \frac{p(y_t | \hat{x}_t^{(i)}) p(\hat{x}_t^{(i)} | x_{t-1}^{(i)})}{q(\hat{x}_t^{(i)} | x_{0:t-1}^{(i)}, y_{1:t})} \quad (24)$$

For i=1, ... N, normalize the importance weights.
A selection step is performed according to the following Equations (25), (26), (27), and (28):
Multiply/Suppress particles, $$(\hat{x}_{0:t}^{(i)}, \hat{P}_{0:t}^{(i)}) \quad (25)$$

with high/low importance weights, $$\tilde{w}_t^{(i)} \quad (26)$$

respectively, to obtain N random particles.
Output: The output of the process is a set of samples that can be used to approximate the posterior distribution as follows:

$$p(x_{0:t} | y_{1:t}) \approx \hat{p}(x_{0:t} | y_{1:t}) = \frac{1}{N} \sum_{i=1}^{N} \delta_{(x_{0:t}^{(i)})}(dx_{0:t}) \quad (27)$$

Resulting in the estimate of, $$E(g_t(x_{0:t})) = \int g_{t(x_{0:t})} p(x_{0:t} | y_{1:t}) dx_{0:t} \approx \frac{1}{N} \sum_{i=1}^{N} g_{t(x_{0:t}^{(i)})} \quad (28)$$

for some function of interest, $g_t$, for instance the marginal conditional mean or the marginal conditional covariance or other moment.

After the occurrence of a lesser, but actionable deterioration of a patient's clinical condition, multiple deterioration events "lurk" out in the future multi-parameter space. Based on the estimated vector trajectory using one or more of the methods described herein, the likelihood or probability of occurrence of any one of those future deterioration events may be calculated. The deterioration events may be viewed as sequentially oriented "landmarks" or letters, and decoding methods such as Viterbi or Hidden Markov Modeling (HMM) methods may also be employed to enhance estimation and detection accuracy. The uncertainty of the vector trajectory estimate as well as deterioration event estimate may be refined using one or more refinement methods, for example, ensemble forecasting.

In some examples, a full, or as complete as possible, M-dimensional set of patient parameters may be gathered such as when a patient who is suffering from chest pain is first admitted into the hospital. Such patient parameters may include, but are not limited to: subject/patient medical history (e.g. ischemic heart disease, diabetes mellitus or chronic renal failure) and demographics (e.g. age, gender), physiologic parameters, such as vital sign measures, ECG, SpO2, respiration rate, blood pressure, body temperature, tissue fluid status, pulmonary-vibrational information, cardio-vibrational information, heart rate variability measures, Glasgow Coma Scale, patient activity via activity sensors such as accelerometer-based motion and vibration sensors etc., as well as clinical observations or diagnoses by the caregiver and any discrete events that may already have occurred prior to admission (e.g. angina, atrial or ventricular tachycardia, heart attack) along with relevant associated information such as the time of occurrence, duration and severity of the discrete events. As described above, some of the data elements are irregularly monitored, static, and/or unchanging patient parameters such as demographics, subject history or discrete events. Other patient parameters are periodically monitored and variable, such as the physiologic data and clinical observations and diagnoses by the caregiver. After admission to the hospital, it is not uncommon for the full set of periodically monitored and variable information (e.g. physiologic, clinical observations and diagnoses) to be updated by the physician, nurse, or other clinical personnel only on a one- or twice-per-shift basis, i.e. every 4-8 hours.

Based on the level of risk determined at time of patient admission, the patient may be fitted with a medical device (e.g., the medical device 100) that is a wearable defibrillator (WCD) to be worn continuously to protect the patient from lethal arrhythmias. If the level of risk is more moderate, but still too high to be of no concern, the patient may be fitted with a wearable monitoring-only (WMO) device to be worn throughout their stay at the hospital. The monitor-only portion may allow for plugging in a module containing the defibrillation functionality should the risk level increase of a lethal arrhythmia occurring at some point in the near future. The WCD or WMO will continuously monitor some subset of the K physiologic parameters or vital signs. For instance, in some versions, a single physiologic signal such as ECG may be monitored continuously, and the deterioration risk assessor may generate two or more patient parameters from the ECG signal: e.g. morphological features such as detection of ectopic beats, ventricular or atrial arrhythmias, T-wave disturbances, multiple heart rate variability measures, etc. In some examples, only one physiologic sensor and one patient parameter are measured and monitored continuously, for instance photoplethysmography that may only be able to measure the R-R interval but not able to measure the Sp02 value. Alternatively, two or more sensors may be used to generate a more complete subset of K physiologic parameters, for instance, ECG, accelerometer, respiration rate via either impedance pneumography or RF-based sensors and measures.

The initial set of patient parameters and the subsequent continuous set of patient parameters each have their limitations. In some examples, the initial set of M patient parameters is a comprehensive set of patient parameters collected at a single point in time. This initial set may be periodically updated at sporadic intervals of 4-8 hours. Thus, the comprehensive set is essentially a static set of patient parameters that cannot assess levels of deterioration risk in between observation times. On the other hand, a set of continuously monitored patient parameters can detect changes during the 4-8 hour period, but this set is a more limited view into the moment-to-moment state of the patient's physiologic system.

Referring to FIG. 11, in one example, the risk tracking and prediction engine executes a deterioration risk tracking and prediction process that includes predictive/tracking loop #1 1101. Predictive/tracking loop #1 1101 processes the initial set of M data points using an enhanced Kalman filter (or other predictive/tracking method such as EKF or particle filters). The deterioration risk tracking and prediction process further includes two or more predictive/tracking loops #2 1102, loop #3 1103, up to n tracking loops loop #n 1104, where each loop has its own update period, represented by z 1110, $z_\alpha$ 1111, $z_\beta$ 1112. Loop #2 1102, in one example may be observing heart rate variability or ECG ST depression measures that may be updated every e.g. 5, 10, 15 or 60 minutes. Loop #3 may be observing blood pressure, pulse oximetry, respiration and ECG detection of arrhythmias that may be updated at a faster rate, e.g. 1, 5, 10, 15, 30, 60 seconds. Loop #4 may be observing the acceleration or other motion sensor at a separate rate, e.g. 1, 3, 5, 25 seconds.

FIG. 12 shows an example of this, where loop #1 1101 is updated at times 1201 and 1202, and loop #2 1102 is updated at times 1201-1208. If just loop #1 1101 were present, the prediction phase would be depicted by the dashed line 1209, with updates at times 1201 and 1202. With two or more loops, estimates of the parameter that would normally observed and updated at a slower rate can now be updated at a faster rate based on the higher rate observations of one or more other parameters. This is depicted in FIG. 12 as the alternated dashed line 1210. Upon the update of parameter estimates at times 1203-1208, a new deterioration risk estimate can be calculated using the full set of M parameters—some of which are observed at that particular time and some of which are estimated via the predictive/tracking loops.

Referring to FIG. 12, at update point 1205, there is a significant change in the estimate that exceeds a threshold 1211. In this example, the significant change is due to a change in clinical observation or diagnosis (e.g., the clinical condition of the patient). The significant change may be due to the predictive/tracking loop estimating that the initial system state parameter for clinical diagnosis (as originally assessed by the admitting caregiver) was incorrect and that a higher probability for diagnosis has changed to a different estimated clinical diagnosis. Based on the new estimated clinical diagnosis, the system state matrix, F, and the input matrix, B, may be modified to result in a higher accuracy of tracking/estimating the patient's condition and risk of deterioration. The gradually decreasing sizes of the subsequent update corrections at 1205, 1206, 1207, and 1208 indicate that the tracking is converging to a stable and more accurate estimate of the actual system state and that the new clinical observation or diagnosis is more consistent with the patient's actual physiologic status. The determination of whether to change the estimated clinical observation or diagnosis may be executed at every update point 1205 or at intervals, e.g. every other, every third, or larger intervals etc., or at random update points. Alternatively, the new clinical observation or diagnosis may be input by a clinician manually, resulting in modifications to either the system state matrix, F or the input matrix, B.

In some examples, the risk tracking and prediction engine monitors acceleration or other motion signals acquired by motion sensors and adjusts estimates for the physiologic parameters for varying levels of activity. In another example, the risk tracking and prediction engine executes risk tracking and prediction process only when the risk tracking and prediction engine detects that the patient activity is low or that the patient is lying down or sitting, via the motion sensors.

Ensemble forecasting is a numerical prediction method that is used to attempt to generate a representative sample of the possible future states of a dynamical system. Ensemble forecasting is a form of Monte Carlo analysis: multiple numerical predictions are conducted using slightly different initial conditions that are all plausible given the past and current set of observations, or measurements. Sometimes the ensemble of forecasts may use different forecast models for different members, or different formulations of a forecast model. The multiple simulations are conducted to account for the two usual sources of uncertainty in forecast models: (1) the errors introduced by the use of imperfect initial conditions, amplified by the chaotic nature of the evolution equations of the dynamical system, which is often referred to as sensitive dependence on the initial conditions; and (2) errors introduced because of imperfections in the model formulation, such as the approximate mathematical methods to solve the equations. Ideally, the verified future dynamical system state should fall within the predicted ensemble spread, and the amount of spread should be related to the uncertainty (error) of the forecast. In some examples, based on the update phases, the deterioration risk assessor compares the trajectory of the observations and the risk estimates to all the trajectories and their associated path uncertainties, and culls an ensemble to more accurately align the ensemble forecast with the observations. For instance, in some examples, the risk tracking and prediction engine calculates the Mahalanobis distance between the observation trajectory and each of the trajectories from the ensemble trajectories. In these examples, the risk tracking and prediction engine sorts the ensemble trajectories from least distance to greatest distance and returns within the risk estimate of patient deterioration only those ensemble trajectories with the closest distance (e.g. the closest 20%).

Returning to FIG. 10, in act 1006 the deterioration risk assessor determines whether the risk estimate of patient deterioration and/or the trajectory of the patient's clinical condition returned by the risk assessment engine falls outside one or more clinical criterion associated with the clinical condition of the patient. For instance, in some examples of the act 1006, the deterioration risk assessor compares the trajectory of the patient's clinical condition to the one or more benchmark trajectories (e.g., the patient's previously determined trajectory) to determine a degree of similarity between trajectories. These benchmark trajectories may include trajectories having an unacceptable level of risk of patient deterioration. Where the degree of similarity (e.g., cosine similarity) is sufficient (e.g., transgresses a threshold value of 0.4, 0.5, 0.6, 0.7, or 0.8 in some examples), the deterioration risk assessor identifies the risk estimate as falling outside the one or more criterion. Similarity measures may vary between examples.

In some example cases, the deterioration risk assessor 320 determines that that current trajectory of the patient's clinical condition deviates significantly from the benchmark trajectories. For example, the degree of similarity based on cosine similarity between the current trajectory and a benchmark similarity may be below a threshold (e.g., 0.4). In such example cases, the current trajectory may be assessed to be closer to another, different benchmark trajectory associated with a different clinical condition. For example, in one scenario, the patient may be monitored with reference to a baseline trajectory associated with syncope. However, the current trajectory of the patient the trajectory may have a degree of similarity to a benchmark trajectory associated with respiratory distress. The deterioration risk assessor 320 can notify a caregiver and provide such information so the caregiver may take appropriate action. In some implementations, the assessor 320 can automatically begin monitoring the patient using the respiratory distress clinical condition and associated criteria.

In an example, while the device is monitoring the patient, a caregiver may use the device user interface to enter new information about the patient that can cause the trajectory of the patient to change. For example, the caregiver may directly input information that the patient has had a significant change in respiration rate (e.g., greater than 50% increase in respiration rate). On receiving such input, the assessor 320 can initiate monitoring the patient using the respiratory distress clinical condition and associated criteria.

In an example, while the device controller 120 is monitoring the patient, the device controller 120 may automatically determine that the patient has suffered a significant change in respiration rate (e.g., greater than 50% increase in respiration rate). An accelerometer and associated circuitry (e.g., vibrational sensors 324 as shown in FIG. 3) positioned on the patient's chest can be coupled to the device. The accelerometer, in certain channels, can provide signals to the assessor 320 indicating the respiration and/or chest wall movements of the patient. On receiving such signals indicating the significant change in respiration rate, the assessor 320 can initiate monitoring the patient using the respiratory distress clinical condition and associated criteria.

For instance, in some examples, the deterioration risk assessor uses semantic similarity to determine whether a trajectory, or ensemble of trajectories, indicates an unacceptable level of risk of patient deterioration. Semantic similarity is disclosed by You Wan, Chenghu Zhou, and Tao Pei in "Semantic-Geographic Trajectory Pattern Mining Based on a New Similarity Measurement" (2017), hereinafter "Wan." In these examples, spatial (e.g., geographic) dimensions disclosed in Wan are replaced with the n-dimensional patient parameters for each point in time. Further, in these examples, a semantic-geographic combined similarity measurement may be employed to calculate trajectory similarity using an intermediate value called semantic intensity, where semantic intensity is a combination of semantic similarity and geographic similarity. As stated in Wan, semantic intensity can be considered the average semantic similarity in a geographic unit distance.

Semantic intensity$(user_1, user_2) =$ $$\frac{\text{Semantic similarity}(STrace_1, STrace_2)}{2 - \text{Geographic similarity}(GTrace_1, GTrace_2)}$$

Where,

Geographic similarity$(CTrace_1, CTrace_2) =$ $$1 - \left(\frac{\sqrt{\sum_{ciCategory}(HausDistAtPoiCate_i)^2/n}}{r}\right)$$

-continued

And, $$\text{Semantic similarity}(STrace_1, STrace_2) = \frac{\sum_{i=1}^{n} W_{1i} * W_{2i}}{\sqrt{\sum_{i=1}^{n}(W_{1i})^2} * \sqrt{\sum_{i=1}^{n}(W_{2i})^2}}$$

Semantic intensity has a range between 0 and 1 with 0=no similarity. In one example, the degree of similarity is determined to be sufficient if the similarity is found to exceed e.g. 0.4, 0.5, 0.6, 0.7, 0.8, in which case the risk estimate is determined to be deviating from or falling outside one or more criterion. In some examples, other aspects of the risk estimate may be evaluated to determine whether the risk estimate falls outside the one or more criterion as described above with reference to FIGS. 5 and 8.

If the risk estimate does not fall outside the one or more clinical criterion, the deterioration risk assessor returns to the act 1002. If the risk estimate falls outside the one or more clinical criterion, the deterioration risk assessor executes act 1008.

In act 1008, the deterioration risk assessor executes a predefined, configurable action such as notifying a caregiver, prompting the patient for information and/or to conduct a neurologic test of the patient. The caregiver, in turn, may take additional action including noting the deviation in trajectory. Subsequent to the act 1008, the monitoring and treatment process 1000 ends.

The monitoring and treatment process 1000 enables medical devices to monitor in-hospital patients at risk for deterioration and, in at least some instances, take preventive measures when the risk becomes unacceptable according to an appropriate standard of care.

In one particular example, the systems and methods described herein assess and monitor a patient's risk for rapid deterioration where the patient is admitted to a hospital emergency room (ER). In this example, a patient presents at the ER complaining of shortness of breath. A nurse triages the patient. As part of this triage, the nurse collects the patient's medical history, demographics, and physiologic parameters using dedicated instruments. The nurse discovers that the patient's age is 72, that she has a heart rate of 124, that her heart rate variability deviates 30% from her baseline, and that she is having ectopic activation or contractions at a rate that deviate by 25% from her baseline. The nurse also collects additional parameters to work up a robust data set for the patient. The additional parameters include respiration rate, SpO2 oxygenation, blood pressure, neurological state, electromechanical parameters, SMo2, and cerebral oxygenation. The additional parameters have normal values.

A resident at the ER reviews the information collected by the nurse, orders that the patient be admitted for observation and orders an HWD, such as the HWD illustrated in FIG. 2, to monitor the patient for rapid deterioration. The nurse configures the HWD, using its user interface to enter some or all of the information previously collected. The nurse removes the various specialized instruments currently monitoring the patient and fits the patient with the configured HWD.

The HWD generates additional patient parameters (e.g., continuously monitored and/or periodically monitored patient parameters) and initiates execution of a deterioration risk assessor. The deterioration risk assessor executes a risk assessment engine. The risk assessment engine identifies the clinical condition of the patient. In this example, the risk assessment engine automatically identifies the clinical condition of the patient as being heart failure by identifying the patient's heart rate, heart rate variability, and ectopic activation or contractions as being abnormal and matching these abnormal parameters to the patient parameters weighted most heavily in the heart failure argument set. The HWD presents the heart failure clinical condition to the nurse for confirmation via its user interface. The nurse confirms the patient clinical condition as heart failure.

The risk assessment engine calculates a deterioration risk estimate by looping through each of the patient parameters in the heart rate argument set and calculating a total score weighted as indicated in the heart failure argument set. Given no changes in the values of the patient parameters initially determined during triage, this total weighted score equals 12, which is the sum of the weighted heart rate score (4*1), the weighted heart rate variability score (4*1), and the weighted ectopic activation or contractions score (4*1). The risk assessment engine further adjusts the total weighted score by a factor of 1.2 due to the patient's advanced age and presenting complaint (shortness of breath). Thus, the risk assessment engine returns a deterioration risk estimate of 13.2 to the deterioration risk assessor.

The deterioration risk assessor determines that the deterioration risk estimate does not fall outside its criteria by comparing the deterioration risk estimate to a threshold value of 14. The HWD continues to generate additional patent parameters and to provide those additional patent parameters to the deterioration risk assessor to protect the patient from an unanticipated or an unrecognized rapid deterioration in her health.

In another particular example, the systems and methods described herein assess and monitor a patient's risk for rapid deterioration where the patient is recovering from an MI. In this example, a physician configures an HWD, such as the HWD illustrated in FIG. 2, using its user interface to select the patient's clinical condition as post-MI.

The HWD generates additional patient parameters (e.g., continuously monitored and/or periodically monitored patient parameters) and initiates execution of a deterioration risk assessor. The deterioration risk assessor executes a risk tracking and prediction engine. The risk tracking and prediction engine identifies the clinical condition of the patient as post-MI based on the configuration data entered by the physician.

In this example, the risk tracking and prediction engine implements an enhanced Kalman filter to generate deterioration risk estimates. The risk tracking and prediction engine initializes the enhanced Kalman filter by populating several models with predetermined values. More specifically, the risk tracking and prediction engine populates the observation model (e.g., a matrix H) for each loop within the enhanced Kalman filter with values of historical patient parameters. The risk tracking and prediction engine populates the state-transition model (e.g., matrix F) for each loop with default values associated with the post-MI clinical condition. The risk tracking and prediction engine populates the control-input model (e.g., matrix B) for each loop with default values associated with the post-MI clinical condition. The risk tracking and prediction engine populates the process noise covariance model (e.g., matrix Q) for each loop with non-zero values. The risk tracking and prediction engine populates the observation noise covariance model (e.g., matrix R) for each loop with non-zero values.

The risk tracking and prediction engine next iterates between predict and update phases for each loop within the enhanced Kalman filter, and, with each iteration, returns an updated deterioration risk estimate to the deterioration risk assessor. Each updated deterioration risk estimate further defines a trajectory of the clinical condition of the patient. The deterioration risk assessor compares this patient trajectory to one or more benchmark trajectories using a similarity measure, such as cosine similarity and/or semantic similarity. These benchmark trajectories may include trajectories associated with rapid deterioration of patient health and/or trajectories associated with clinical conditions other than the currently recorded clinical condition of the patient. In this example, the deterioration risk assessor determines that the similarity measure between the patient trajectory and a benchmark trajectory associated with the heart failure clinical condition is 0.8. The deterioration risk assessor next compares the similarity measure of 0.8 to a threshold similarity of 0.6 and, in response to determining that the similarity measure exceeds the threshold similarity, executes a preconfigured action. Here, the preconfigured action is changing the recorded clinical condition of the patient from post-MI to heart failure and notifying a caregiver of this change.

In a subsequent iteration, the deterioration risk assessor determines that a similarity measure between the recorded clinical condition of the patient and a benchmark trajectory associated with rapid deterioration exceeds the threshold similarity. In response to making this determination, the deterioration risk assessor generates a notification to a caregiver that alerts the caregiver to the predicted rapid deterioration so that remedial treatment can be provided to the patient.

Although the subject matter contained herein has been described in detail for the purpose of illustration, it is to be understood that such detail is solely for that purpose and that the present disclosure is not limited to the disclosed examples, but, on the contrary, is intended to cover modifications and equivalent arrangements that are within the scope of the appended claims. For example, it is to be understood that the present disclosure contemplates that, to the extent possible, one or more features of any example can be combined with one or more features of any other example.

Other examples are within the scope of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A medical device for assessing risk of patient deterioration comprising:
   a memory storing data identifying
      a plurality of presentable clinical conditions,
      an indication, for each presentable clinical condition of the plurality of presentable clinical conditions, of whether the presentable clinical condition was presented to a healthcare provider,
      a plurality of predictive risk assessment processes associated with the plurality of presentable clinical conditions, and
      a corresponding plurality of clinical criteria associated with the plurality of predictive risk assessment processes;
   a plurality of sensing electrodes configured to couple externally to a skin of a patient and to acquire electrocardiogram (ECG) signals;

one or more physiologic sensors distinct from the plurality of sensing electrodes and configured to couple externally to the patient and configured to acquire one or more physiologic signals distinct from the ECG signals;
a user interface configured to display prompts to a user of the medical device; and
a housing comprising
the memory,
the user interface, and
at least one processor coupled to the memory, the plurality of sensing electrodes, the user interface, and the one or more physiologic sensors, the at least one processor being configured to
generate ECG data over a predetermined period of time based on the ECG signals,
generate physiologic data over the predetermined period of time based on the one or more physiologic signals,
receive at least one of medical history and demographic information of the patient,
store the ECG data, the physiologic data, and the at least one of medical history and demographic information in a vector,
update a first portion of the vector continuously, update a second portion of the vector periodically, and update a third portion of the vector in response to one or more of admission to a first healthcare facility, transfer between locations within the first healthcare facility, transfer from the first healthcare facility to a second healthcare facility, or transfer from a first location to a second location,
identify a first clinical condition from the plurality of presentable clinical conditions based on the ECG data, the physiologic data, and the at least one of medical history and demographic information of the patient, wherein the first clinical condition has associated therewith a first benchmark trajectory,
identify a first predictive risk assessment process from the plurality of predictive risk assessment processes, the first predictive risk assessment process being associated with the first clinical condition selected from the plurality of presentable clinical conditions,
execute the first predictive risk assessment process to prompt the user to respond, via the user interface, to a tactile or audio signal, and
generate a first risk estimate of rapid deterioration of the patient due to the first clinical condition within an upcoming time period based on data acquired from the plurality of sensing electrodes, data acquired from a user response to the tactile or audio signal, and data acquired from the one or more physiologic sensors,
determine an observed trajectory of the first clinical condition of the patient based on at least some of the ECG data and at least some of the physiologic data,
evaluate a first degree of similarity between the observed trajectory and the first benchmark trajectory associated with the first clinical condition,
evaluate a second degree of similarity between the observed trajectory and a second benchmark trajectory associated with a second clinical condition,
in response to determining that the second degree of similarity is greater than the first degree of similarity,
generate a notification identifying one or more of the first clinical condition or the second clinical condition,
display the notification on the user interface, and
transmit the notification to a remote device, the notification indicating that the patient will be monitored using criteria associated with the second clinical condition,
execute a second predictive risk assessment process from the plurality of predictive risk assessment processes, wherein executing the second predictive risk assessment process
includes executing a recursive process that comprises a plurality of loops, each loop of the plurality of loops tracking actual patient parameter values, and generating predicted patient parameter values, wherein each loop of the recursive process is associated with a distinct patient parameter and a corresponding distinct update period, and
generates a second risk estimate of rapid deterioration of the patient due to the second clinical condition based on data acquired from the plurality of sensing electrodes and data acquired from the one or more physiologic sensors, and
in response to determining that the second risk estimate is outside a clinical criterion associated with the second clinical condition and is thereby indicative of an increased risk of rapid deterioration of the patient, execute a neurological assessment of the patient, the neurological assessment comprising prompting the patient to provide a response via the user interface.

2. The medical device of claim 1, wherein the upcoming time period comprises at least one of within less than 1 hour, within 1-2 hours, within 2-4 hours, within 4-6 hours, within 6-8 hours, within 8-12 hours, or within 12-24 hours.

3. The medical device of claim 1, wherein the remote device is associated with at least one of an in-hospital medical emergency team (MET), a medical emergency response team (MERT), and an in-hospital rapid response team (RRT).

4. The medical device of claim 1, the least one processor being further configured to:
generate updated ECG data from ECG signals acquired subsequent to execution of the second predictive risk assessment process;
generate updated physiologic data from one or more physiologic signals acquired subsequent to execution of the second predictive risk assessment process;
determine a trajectory of the second clinical condition of the patient at least in part by analyzing the first clinical condition, the first risk estimate of rapid deterioration of the patient, the updated ECG data and the updated physiologic data; and
generate an updated notification in response to the trajectory of the second clinical condition of the patient indicating an updated risk of rapid deterioration of the second clinical condition of the patient.

5. The medical device of claim 1, the at least one processor being further configured to receive an initial patient assessment and identify the first clinical condition based on the initial patient assessment.

6. The medical device of claim 1, wherein the plurality of presentable clinical conditions comprises one or more of a heart failure condition, a post syncope condition, a post myocardial infarction condition, and a breathing disorder condition.

7. The medical device of claim 1, the at least one processor being configured to automatically identify the first clinical condition based on an initial patient assessment of the ECG data, the physiologic data, and the at least one of medical history and demographic information of the patient.

8. The medical device of claim 1, wherein the ECG data, the physiologic data, and the at least one of medical history and demographic information of the patient comprises a plurality of patient parameters that are input to the first predictive risk assessment process associated with the first clinical condition of the patient.

9. The medical device of claim 8, the at least one processor being further configured to execute the first predictive risk assessment process by:
    identifying one or more associations between the first clinical condition and one or more patient parameters of the plurality of patient parameters; and
    analyzing the one or more patient parameters of the plurality of patient parameters to generate the first risk estimate of rapid deterioration of the patient.

10. The medical device of claim 8, wherein the plurality of patient parameters comprises one or more of patient ECG metrics, patient lung fluid level parameters, patient heart rate parameters, patient heart rate variability parameters, parameters of one or more arrhythmias experienced by the patient, patient cardio-vibrational parameters, patient respiratory rate parameters, patient pulse oxygen parameters, patient motion parameters, patient pallor parameters, and patient neurological condition parameters.

11. The medical device of claim 1, the at least one processor being further configured to:
    re-execute the first predictive risk assessment process according to a schedule; and
    decrease a span of time between scheduled re-executions of the first predictive risk assessment process in response to the first risk estimate being outside a first clinical criterion and thereby indicating an increased risk of rapid deterioration of the patient.

12. The medical device of claim 1, wherein the first risk estimate of rapid deterioration of the patient comprises one or more of a continuous decline in patient health spanning the upcoming time period and a steep decline in patient health falling within the upcoming time period.

13. The medical device of claim 1, wherein the medical device is ambulatory and wearable.

14. A medical device for assessing patient deterioration comprising:
    a memory storing data identifying
        a plurality of presentable clinical conditions,
        an indication, for each presentable clinical condition of the plurality of presentable clinical conditions, of whether the presentable clinical condition was presented to a healthcare provider,
        a plurality of predictive risk assessment processes associated with the plurality of presentable clinical conditions, and
        a corresponding plurality of clinical criteria associated with the plurality of predictive risk assessment processes;
    a plurality of sensing electrodes configured to couple externally to a skin of a patient and to acquire electrocardiogram (ECG) signals;
    one or more physiologic sensors distinct from the plurality of sensing electrodes and configured to couple externally to the patient and configured to acquire one or more physiologic signals distinct from the ECG signals;
    a user interface configured to display prompts to a user of the medical device and receive initial patient assessment data from a caregiver; and
    a housing comprising
        the memory,
        the user interface, and
        at least one processor coupled to the memory, the plurality of sensing electrodes, the user interface, and the one or more physiologic sensors, the at least one processor being configured to
            generate ECG data over a predetermined period of time based on the ECG signals,
            generate physiologic data over the predetermined period of time based on the one or more physiologic signals,
            at least one of automatically determine and receive the initial patient assessment data identifying a first clinical condition of the patient from the plurality of presentable clinical conditions,
            store the ECG data, the physiologic data, and the initial patient assessment data in a vector,
            update a first portion of the vector continuously, update a second portion of the vector periodically, and update a third portion of the vector in response to one or more of admission to a first healthcare facility, transfer between locations within the first healthcare facility, transfer from the first healthcare facility to a second healthcare facility, or transfer from a first location to a second location,
            execute a first predictive risk assessment process associated with the first clinical condition at first predetermined intervals of time based on the ECG signals, the one or more physiologic signals, and the initial patient assessment data to generate a first plurality of risk estimates of the first clinical condition of the patient,
            determine an observed trajectory of the patient over a first upcoming time period based on all or a portion of the ECG signals, the one or more physiologic signals, and the initial patient assessment data, the observed trajectory comprising at least one first predictive value in accordance with the first predictive risk assessment process,
            evaluate a degree of similarity between the observed trajectory and each of a plurality of benchmark trajectories, wherein each of the benchmark trajectories is associated with one of the plurality of presentable clinical conditions other than the first clinical condition,
            identify a second clinical condition associated with a particular one of the plurality of benchmark trajectories, wherein the degree of similarity between the observed trajectory and the particular benchmark trajectory exceeds a threshold similarity,
            execute a second predictive risk assessment process associated with the second clinical condition of the patient at second predetermined intervals of time to generate a second plurality of risk estimates of the second clinical condition of the patient, wherein executing the second predictive risk assessment process includes executing a recursive process that comprises a plurality of loops, each loop of the plurality of loops tracking actual patient parameter values, and generating predicted patient parameter values, wherein each loop of the recursive process is associated with a distinct patient parameter and a corresponding distinct update period, make a determination that the patient is likely to require emergency medical intervention based on at least one of (a) the observed trajectory being outside clinical criteria associated with the first clinical condition and (b) the observed trajectory being outside clinical criteria associated with the second clinical condition, and after making the determination that the patient is likely to require emergency medical intervention execute a neurological assessment of the patient, the neurological assessment comprising prompting the patient to respond, via the user interface, to a tactile or audio signal, generate a notification indicating a likelihood that the patient will require emergency medical intervention, wherein the notification identifies one or more of the first clinical condition or the second clinical condition, display the notification on the user interface, and transmit the notification to a remote device.

15. The medical device of claim 14, wherein the remote device is associated with at least one of an in-hospital medical emergency team (MET), a medical emergency response team (MERT), and an in-hospital rapid response team (RRT).

16. The medical device of claim 14, the at least one processor being further configured to set a flag stored in the memory that indicates the patient is likely to require emergency medical intervention.

17. The medical device of claim 14, the at least one processor being configured to determine the observed trajectory of the patient based on the first plurality of risk estimates of the first clinical condition of the patient.

18. The medical device of claim 14, wherein the ECG signals, the one or more physiologic signals, and at least one of a medical history and demographic information of the patient comprise a plurality of patient parameters that are input to the first predictive risk assessment process associated with the first clinical condition of the patient.

19. The medical device of claim 18, the at least one processor being further configured to execute the first predictive risk assessment process by:

identifying one or more associations between the first clinical condition and one or more patient parameters of the plurality of patient parameters; and analyzing the one or more patient parameters of the plurality of patient parameters to generate a first risk estimate of the first plurality of risk estimates of the first clinical condition of the patient.

20. The medical device of claim 19, wherein the first predictive risk assessment process is configured to analyze the one or more patient parameters of the plurality of patient parameters at least in part by applying distinct weights to respective patient parameters of the one or more patient parameters.

21. The medical device of claim 19, wherein the plurality of patient parameters comprises one or more of patient ECG metrics, patient lung fluid level parameters, patient heart rate parameters, patient heart rate variability parameters, parameters of one or more arrhythmias experienced by the patient, patient cardio-vibrational parameters, patient respiratory rate parameters, patient pulse oxygen parameters, patient motion parameters, patient pallor parameters, and patient neurological condition parameters.

22. The medical device of claim 14, wherein the plurality of presentable clinical conditions comprises one or more of a heart failure condition, a post syncope condition, a post myocardial infarction condition, and a breathing disorder condition.

23. The medical device of claim 14, wherein the first upcoming time period comprises within less than 1 hour, within 1-2 hours, within 2-4 hours, within 4-6 hours, within 6-8 hours, within 8-12 hours, or within 12-24 hours.

24. A medical device for assessing patient deterioration comprising:

a memory storing data identifying
 a plurality of presentable clinical conditions,
 an indication, for each presentable clinical condition of the plurality of presentable clinical conditions, of whether the presentable clinical condition was presented to a healthcare provider,
 a plurality of predictive risk assessment processes associated with the plurality of presentable clinical conditions, and
 a corresponding plurality of clinical criteria associated with the plurality of predictive risk assessment processes; and at least one processor operably coupled to the memory, the at least one processor being configured to
 at least one of automatically determine and receive initial patient assessment data identifying a first clinical condition of a patient from the plurality of presentable clinical conditions, wherein the first clinical condition has associated therewith a first benchmark trajectory,
 receive electrocardiogram (ECG) signals from a plurality of sensing electrodes coupled to the patient,
 generate ECG data over a predetermined period of time based on the ECG signals,
 receive physiologic signals from one or more physiologic sensors coupled to the patient, wherein the physiologic signals are distinct from the ECG signals,
 generate physiologic data over the predetermined period of time based on the physiologic signals,
 store the ECG data, the physiologic data, and the initial patient assessment data in a vector,
 update a first portion of the vector continuously, update a second portion of the vector periodically, and update a third portion of the vector in response to one or more of admission to a first healthcare facility, transfer between locations within the first healthcare facility, transfer from the first healthcare facility to a second healthcare facility, or transfer from a first location to a second location,
 execute a first predictive risk assessment process associated with the first clinical condition based on data acquired from the plurality of sensing electrodes, data acquired from the one or more physiologic sensors, and the initial patient assessment data to generate a first plurality of risk estimates of the first clinical condition of the patient,
 determine a first observed trajectory of the first clinical condition of the patient over a first upcoming time period based on all or a portion of the ECG signals, the physiologic signals, and the initial patient assessment data, the first upcoming time period comprising at least one of within less than 1 hour, within 1-2 hours, within 2-4 hours, within 4-6 hours, within 6-8 hours, within 8-12 hours, or within 12-24 hours, evaluate a first degree of similarity between the first observed trajectory and the first benchmark trajectory associated with the first clinical condition, evaluate a second degree of similarity between the first observed trajectory and a second benchmark trajectory associated with a second clinical condition, make a determination that the second degree of similarity is greater than the first degree of similarity, execute a second predictive risk assessment process associated with the second clinical condition based on data acquired from the plurality of sensing electrodes and data acquired from the one or more physiologic sensors to generate a second plurality of risk estimates of the second clinical condition of the patient, wherein executing the second predictive risk assessment process includes executing a recursive process that comprises a plurality of loops, each loop of the plurality of loops tracking actual patient parameter values, and generating predicted patient parameter values, wherein each loop of the recursive process is associated with a distinct patient parameter and a corresponding distinct update period, determine a second observed trajectory of the second clinical condition of the patient over a second upcoming time period based on all or a portion of the ECG signals and the physiologic signals, the second observed trajectory comprising at least one predictive value in accordance with the second predictive risk assessment process, make a determination that the patient is likely to require emergency medical intervention within the first upcoming time period or the second upcoming time period based on one or more of (a) the first observed trajectory being outside clinical criteria associated with the first clinical condition and (b) the second observed trajectory being outside clinical criteria associated with the second clinical condition, and after making the determination that the patient is likely to require emergency medical intervention execute a neurological assessment of the patient, the neurological assessment comprising prompting the patient to respond, via a user interface, to a tactile or audio signal, generate a notification indicating a likelihood that the patient will require emergency medical intervention within the first upcoming time period or the second upcoming time period, wherein the notification identifies one or more of the first clinical condition or the second clinical condition, display the notification on the user interface, and transmit the notification to a remote device.

25. The medical device of claim 24, wherein the remote device is associated with at least one of an in-hospital medical emergency team (MET), a medical emergency response team (MERT), and an in-hospital rapid response team (RRT).

\* \* \* \* \*